United States Patent
Kato et al.

(10) Patent No.: US 8,101,621 B2
(45) Date of Patent: Jan. 24, 2012

(54) AMINOPYRIDINE DERIVATIVES HAVING AURORA A SELECTIVE INHIBITORY ACTION

(75) Inventors: Tetsuya Kato, Tsukuba (JP); Nobuhiko Kawanishi, Moriya (JP); Takashi Mita, Tsukuba (JP); Keita Nagai, Tsukuba (JP); Katsumasa Nonoshita, Tsukuba (JP); Mitsuru Ohkubo, Ushiku (JP)

(73) Assignee: MSD K.K., Chiyoda-ku, Tokyo (JP)

( * ) Notice: Subject to any disclaimer, the term of this patent is extended or adjusted under 35 U.S.C. 154(b) by 646 days.

(21) Appl. No.: 12/226,639

(22) PCT Filed: Apr. 25, 2007

(86) PCT No.: PCT/JP2007/059413
§ 371 (c)(1),
(2), (4) Date: Oct. 24, 2008

(87) PCT Pub. No.: WO2007/126126
PCT Pub. Date: Nov. 8, 2007

(65) Prior Publication Data
US 2009/0192174 A1   Jul. 30, 2009

(30) Foreign Application Priority Data
Apr. 27, 2006   (JP) .................. 2006-124475

(51) Int. Cl.
C07D 239/42   (2006.01)
C07D 239/02   (2006.01)
C07D 403/14   (2006.01)

(52) U.S. Cl. .............. 514/256; 544/326; 544/328

(58) Field of Classification Search .......... None
See application file for complete search history.

(56) References Cited

U.S. PATENT DOCUMENTS
2006/0106029 A1   5/2006 Ohkubo et al.

FOREIGN PATENT DOCUMENTS
| WO | WO02/57259 | 7/2002 |
|---|---|---|
| WO | WO03/031606 | 4/2003 |
| WO | WO2004/058782 | 7/2004 |
| WO | WO 2005040159 | * 5/2005 |

* cited by examiner

Primary Examiner — Noble Jarrell
(74) Attorney, Agent, or Firm — Matthew A. Leff; David A. Muthard

(57) ABSTRACT

The present invention relates to a compound of general formula I:

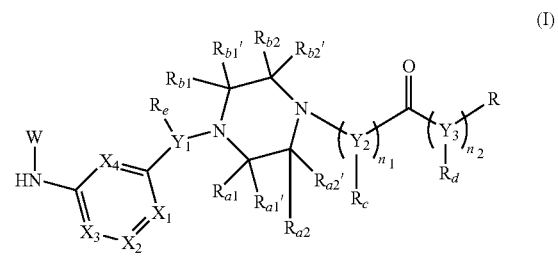

wherein:

$n_1$ and $n_2$ are the same or different, and are 0 or 1; R is aryl, heteroaryl, etc.; $R_e$ is hydrogen atom or lower alkyl; two groups selected from four groups consisting of (i) either one of $R_{a1}$ and $R_{a1}'$, (ii) either one of $R_{a2}$ and $R_{a2}'$, (iii) either one of $R_{b1}$ and $R_{b1}'$, and (iv) either one of $R_{b2}$ and $R_{b2}'$, are combined to form —$(CH_2)_n$— where n is 1, 2 or 3; and among $R_{a1}$, $R_{a1}'$, $R_{a2}$, $R_{a2}'$, $R_{b1}$, $R_{b1}'$, $R_{b2}$ and $R_{b2}'$, the groups which do not form —$(CH_2)_n$— are each independently hydrogen atom, etc.; $X_1$, $X_2$, $X_3$ and $X_4$ are each independently CH, N, etc.; $Y_1$, $Y_2$, $Y_3$ and $Y_4$ are the same or different and are CH or N, etc.; W is a 5-membered aromatic heterocyclic group, or a pharmaceutically acceptable salt or ester thereof.

7 Claims, No Drawings

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Completely Synthetic Amino Acid Sequence

<400> SEQUENCE: 1

Leu Arg Arg Ala Ser Leu Gly
 1               5
```

AMINOPYRIDINE DERIVATIVES HAVING AURORA A SELECTIVE INHIBITORY ACTION

PRIORITY CLAIM

This application is a §371 application of PCT/JP2007/059413 that was filed on Apr. 25, 2007, which claims priority from Japanese Application No. 2006-124475, filed on Apr. 27, 2006, now expired.

TECHNICAL FIELD

The present invention relates to novel aminopyridine derivatives which are useful in the pharmaceutical field, and more particularly, to those which inhibit the growth of tumor cells based on an Aurora A selective inhibitory action and exhibit an antitumor effect, and also to an Aurora A selective inhibitor and an antitumor agent containing them.

BACKGROUND ART

Aurora kinase is a serine/threonine kinase involved in cell division. With regard to the Aurora kinase, three subtypes of A, B and C are known at present, and they have very high homology to each other. Aurora A participates in the maturation and distribution of centrosome or in the formation of spindle body. On the other hand, it is believed that Aurora B participates in the aggregation and pairing of chromosome, a spindle checkpoint and cytoplasm division [*Nat. Rev. Mol. Cell. Biol.*, No. 4, pp. 842-854]. Also, it is believed that Aurora C acts similarly as a result of interaction with Aurora B [*J. Biol. Chem.*, Epub ahead (2004)]. From the fact that high expression of Aurora A has been hitherto confirmed in many cancer cells; that high expression of Aurora A in normal cells leads to transformation of normal cell strains of rodent; and the like, Aurora A, being one of oncogenes, is recognized to be an adequate target for an antitumor agent [*EMBO J.*, No. 17, pp. 3052-3065 (1998)].

There is another report that cancer cells in which Aurora A is highly expressed have a resistance to paclitaxel [*Cancer Cell*, Vol. 3, pp. 51-62 (2003)]. Meanwhile, with regard to the Aurora kinase inhibitor, development of subtype-selective drugs has been thought to be difficult in view of high homology among subtypes, protein structure analysis and the like; and although there have been known reports on drugs such as ZM447439 which inhibit both Aurora A and Aurora B at the same time [*J. Cell Biol.*, No. 161, pp. 267-280 (2003); *J. Cell Biol.*, No. 161, pp. 281-294, (2003); *Nat. Med.*, No. 10, pp. 262-267, (2004)], no report concerning Aurora A selective drugs have been known. Thus, in those reports, disclosed is the antitumor effect only for the case where a drug which inhibits both Aurora A and Aurora B at the same time is solely administered. In addition, there has been also reported a result that in a drug which inhibits both Aurora A and Aurora B at the same time, the Aurora kinase inhibiting action attenuates the action of paclitaxel [*J. Cell Biol.*, No. 161, pp. 281-294, (2003)].

Now, patent applications concerning compounds having an Aurora kinase inhibiting action have been previously filed (WO 02/057259, U.S. Pat. No. 6,664,247, etc.), and patent applications concerning aminopyridine derivatives has been filed as well (U.S. Pat. No. 6,586,424, etc.). However, there has been no report on an aminopyridine derivative having an excellent Aurora A selective inhibitory action thus far.

DISCLOSURE OF THE INVENTION

The problems that the present invention should solve are to create novel aminopyridine derivatives which show an excellent Aurora A selective inhibitory action and cell-growth inhibitory action based on the foregoing, as well as achieve a synergistic action by a combined use with other antitumor agent(s).

In order to solve the above problems, the present inventors have synthesized a variety of novel aminopyridine derivatives and found that the compound represented by the following Formula (I) shows an excellent Aurora A selective inhibitory action and cell-growth inhibitory action based on the foregoing, and also achieves a synergistic action by a combined use with other antitumor agents, thus completing the invention. With regard to those cancers which have been unable to be completely treated with known antitumor agents such as paclitaxel —whose sufficient amount of the agents could not be used due to the side effects or drug resistance—the administration of the compound according to the invention or the combined administration of the compound according to the invention with other antitumor agent is a expected to exhibit an excellent antitumor effect (including potentiation of action due to the other antitumor agent) and an effect of attenuating side-effects.

Thus, the invention relates to a compound of general formula I:

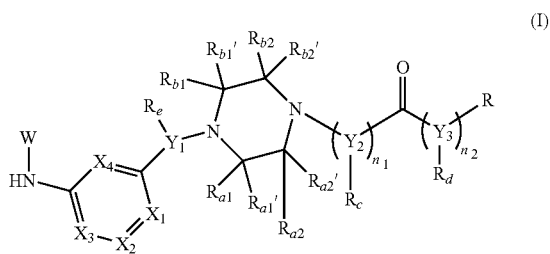

wherein:
$n_1$ is 0 or 1;
$n_2$ is 0 or 2;
R is aryl, heteroaryl, or cycloalkyl any of which may be substituted;
$R_e$ is hydrogen atom or lower alkyl which may be substituted;
with regard to $R_{a1}$, $R_{a1}'$, $R_{a2}$, $R_{a2}'$, $R_{b1}$, $R_{b1}'$, $R_{b2}$ and $R_{b2}'$, two groups selected from four groups consisting of (i) either one of $R_{a1}$ and $R_{a1}'$, (ii) either one of $R_{a2}$ and $R_{a2}'$, (iii) either one of $R_{b1}$ and $R_{b1}'$, and (iv) either one of $R_{b2}$ and $R_{b2}'$, are combined to form —$(CH_2)_n$— where n is 1, 2 or 3; and among $R_{a1}$, $R_{a1}'$, $R_{a2}$, $R_{a2}'$, $R_{b1}$, $R_{b1}'$, $R_{b2}$ and $R_{b2}'$, the groups which do not form —$(CH_2)_n$— are each independently hydrogen atom or lower alkyl which may be substituted;
$X_1$ is CH, $CX_{1a}$, or N wherein $X_{1a}$ is lower alkyl which may be substituted;
$X_2$ is CH $CX_{2a}$, or N wherein:
  $X_{2a}$ is lower alkyl; or
  $X_{2a}$ is a substituent selected from <substituent group $A_1$>, or lower alkyl which is substituted with one or more of the same or different substituents selected from <substituent group $A_1$>, wherein <substituent group $A_1$> is halogen atom; cyano; hydroxyl; lower alkylamino; di-lower alkylamino; lower alkoxy which may be substituted with one or more hydroxyl groups; lower alkylthio; and lower alkylsulfonyl; or
  $X_{2a}$ is $COOR_1$ or $CONR_2R_3$ wherein:
    $R_1$ is hydrogen atom or lower alkyl which may be substituted;

$R_2$ and $R_3$, which may be the same or different, are each hydrogen atom, lower alkyl which may be substituted, or cycloalkyl which may be substituted; or alternatively $R_2$ and $R_3$, together with the nitrogen atom to which they bond, form a 5- or 6-membered aliphatic heterocyclic group which contains at least one atom selected from N, O and S and which may be substituted; or $X_{2a}$ is a 3- to 6-membered cycloalkyl which may be substituted, wherein two hydrogen atoms that are bonded to the same carbon atom of the cycloalkyl may be substituted with oxo and neighboring two carbon atoms constituting the cycloalkyl ring may form a double-bond; or lower alkyl which is substituted with the cycloalkyl; or $X_3$ is CH, $CX_{3a}$, or N wherein $X_{3a}$ is lower alkyl which may be substituted;

$X_4$ is CH or N;

the number of nitrogen atoms among $X_1$, $X_2$, and $X_3$, and $X_4$ is one or two;

$Y_1$, $Y_2$, and $Y_3$ are each independently CH or N; however, if $Y_1$ is CH and $R_e$ is hydrogen atom, then the two hydrogen atoms may be substituted with oxo;

W is the following residue:

wherein:

$W_1$ is CH, N, NH, O, or S;

$W_2$ is CH, $CW_{2a}$, N, $NW_{2b}$, O or S, wherein $W_{2a}$ and $W_{2b}$ are each independently hydrogen atom, halogen atom, cyano, lower alkyl having one to two carbon atoms, cycloalkyl having three to five carbon atoms, or lower alkyl having one to two carbon atoms, which may be substituted with one or more halogen atoms;

$W_3$ is C or N; and at least one of $W_1$, $W_2$, and $W_3$ is carbon atom; however two of $W_1$, $W_2$, and $W_3$ are not simultaneously O and S, or a pharmaceutically acceptable salt or ester thereof.

Also, another embodiment of the present invention is represented by a compound of general general formula $I_0$:

(I₀)

wherein:

$n_1$ is 0 or 1;

$n_2$ is 0 or 1;

R is aryl, heteroaryl, or cycloalkyl any of which may be substituted;

$R_e$ is hydrogen atom or lower alkyl; or $X_1$ is CH, $CX_{1a}$, or N wherein $X_{1a}$ is lower alkyl which may be substituted;

$X_2$ is CH $CX_{2a}$, or N wherein:

$X_{2a}$ is lower alkyl;

$X_{2a}$ is a substituent selected from <substituent group $A_1$>, or lower alkyl which is substituted with one or more of the same or different substituents selected from <substituent group $A_1$>, wherein <substituent group $A_1$> is halogen atom; cyano; hydroxyl; lower alkylamino; di-lower alkylamino; lower alkoxy which may be substituted with one or more hydroxyl groups; lower alkylthio; and lower alkylsulfonyl; or $X_{2a}$ is $COOR_1$ or $CONR_2R_3$ wherein:

$R_1$ is hydrogen atom or lower alkyl which may be substituted;

$R_2$ and $R_3$, which may be the same or different, are each hydrogen atom, lower alkyl which may be substituted, or cycloalkyl which may be substituted; or alternatively $R_2$ and $R_3$, together with the nitrogen atom to which they bond, form a 5- or 6-membered aliphatic heterocyclic group which contains at least one atom selected from N, O and S and which may be substituted; or $X_{2a}$ is a 3- to 6-membered cycloalkyl which may be substituted, wherein two hydrogen atoms that are bonded to the same carbon atom of the cycloalkyl may be substituted with oxo and neighboring two carbon atoms constituting the cycloalkyl ring may form a double-bond; or lower alkyl which is substituted with the cycloalkyl; or $X_3$ is CH, $CX_{3a}$, or N wherein $X_{3a}$ is lower alkyl which may be substituted;

$X_4$ is CH or N;

the number of nitrogen atoms among $X_1$, $X_2$, and $X_3$, and $X_4$ is one or two;

$Y_1$, $Y_2$, and $Y_3$ are each independently CH or N; however, if $Y_1$ is CH and $R_e$ is hydrogen atom, then the two hydrogen atoms may be substituted with oxo;

W is the following residue:

wherein:

$W_1$ is CH, N, NH, O, or S;

$W_2$ is CH, $CW_{2a}$, N, $NW_{2b}$, O or S, wherein $W_{2a}$ and $W_{2b}$ are each independently hydrogen atom, halogen atom, cyano, lower alkyl having one to two carbon atoms, cycloalkyl having three to five carbon atoms, or lower alkyl having one to two carbon atoms, which may be substituted with one or more halogen atoms;

$W_3$ is C or N; and at least one of $W_1$, $W_2$, and $W_3$ is carbon atom; however two of $W_1$, $W_2$, and $W_3$ are not simultaneously O and S, or a pharmaceutically acceptable salt or ester thereof.

The invention also relates to a combined preparation for simultaneous, separate or sequential administration in the treatment of cancer, comprising two separate preparations which are:

(i) a preparation comprising, together with a pharmaceutically acceptable carrier or diluent, a compound represented by the above-described Formula (I) or a pharmaceutically acceptable salt or ester thereof; and (ii) a preparation comprising, together with a pharmaceutically acceptable carrier or diluent, one antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, interferons, biological response modifiers and other antitumor agents as well as pharmaceutically acceptable salt(s) or ester(s) thereof, wherein:

the antitumor alkylating agent is nitrogen mustard N-oxide, cyclophosphamide, ifosfamide, melphalan, busulfan, mitobronitol, carboquone, thiotepa, ranimustine, nimustine, temozolomide or carmustin;

the antitumor antimetabolite is methotrexate, 6-mercaptopurine riboside, mercaptopurine, 5-fluorouracil, tegafur, doxyfluridine, carmofur, cytarabine, cytarabine ocfosfate, enocitabine, S-1, gemcitabine, fludarabine or pemetrexed disodium;

the antitumor antibiotic is actinomycin D, doxorubicin, daunorubicin, neocarzinostatin, bleomycin, peplomycine, mitomycin C, aclarubicin, pirarubicin, epirubicin, zinostatin stimalamer, idarubicin, sirolimus or valrubicin;

the plant-derived antitumor agent is vincristine, vinblastine, vindesine, etoposide, sobuzoxane, docetaxel, paclitaxel or vinorelbine;

the antitumor platinum coordination compound is cisplatin, carboplatin, nedaplatin or oxaliplatin;

the antitumor camptothecin derivative is irinotecan, topotecan or camptothecin;

the antitumor tyrosine kinase inhibitor is gefitinib, imatinib, sorafenib, sunitinib, dasatinib, or erlotinib;

the monoclonal antibody is cetuximab, bevacizumab, rituximab, bevacizumab, alemtuzumab or trastuzumab;

the interferon is interferon α, interferon α-2a, interferon α-2b, interferon β, interferon γ-1a or interferon γ-n1;

the biological response modifier is krestin, lentinan, sizofuran, picibanil or ubenimex; and the other antitumor agent is mitoxantrone, L-asparaginase, procarbazine, dacarbazine, hydroxycarbamide, pentostatin, tretinoin, alefacept, darbepoetin alfa, anastrozole, exemestane, bicalutamide, leuprolelin, flutamide, fulvestrant, pegaptanib octasodium, denileukin diftitox, aldesleukin, thyrotropin alfa, arsenic trioxide, bortezomib, capecitabine or goserelin.

The invention further relates to a pharmaceutical composition comprising, together with a pharmaceutically acceptable carrier or diluent, a compound represented by the above-described Formula (I) or a pharmaceutically acceptable salt or ester thereof, and an antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, biological response modifiers and other antitumor agents (here, the definition of each antitumor agent is the same as that defined hereinabove) or a pharmaceutically acceptable salt or ester thereof.

The invention still further relates to a method for the treatment of cancer, comprising administering simultaneously, separately or sequentially a therapeutically effective amount of a compound represented by the above-described Formula (I) or a pharmaceutically acceptable salt or ester thereof in combination with a therapeutically effective amount of an antitumor agent selected from the group consisting of antitumor alkylating agents, antitumor antimetabolites, antitumor antibiotics, plant-derived antitumor agents, antitumor platinum coordination compounds, antitumor camptothecin derivates, antitumor tyrosine kinase inhibitors, monoclonal antibodies, interferons, biological response modifiers and other antitumor agents (here, definition of each antitumor agent is the same as that defined hereinabove) or a pharmaceutically acceptable salt or ester thereof.

Furthermore, the invention relates to the use of an Aurora selective A inhibitor for the manufacture of a medicament for the treatment of cancer; and the use of an Aurora selective A inhibitor in combination with an antitumor agent for the manufacture of a medicament for the treatment of cancer; and also relates to a method of treating cancer to a mammal (particularly a human) which comprises administering to said mammal a therapeutically effective amount of an Aurora selective A inhibitor; and a method of treating cancer in a mammal (particularly a human) which comprises administering to said mammal a therapeutically effective amount of an Aurora selective A inhibitor in combination with a therapeutically effective amount of an antitumor agent.

The invention relates to a pharmaceutical composition comprising as active ingredient an Aurora selective A inhibitor; and a pharmaceutical composition comprising as active ingredient an Aurora selective A inhibitor, together with an antitumor agent.

Next, symbols and terms used in the present specification will be explained.

The term "lower alkyl" in the above Formula (I) and Formula ($I_0$) denotes a linear or branched alkyl group having 1 to 6 carbon atoms, and examples thereof include, for example, methyl, ethyl, propyl, isopropyl, butyl, isobutyl, sec-butyl, tert-butyl, pentyl and hexyl, among these methyl being preferred.

The term "aryl" in the above Formula (I) and Formula ($I_0$) denotes a monocyclic, bicycle or tricyclic aromatic hydrocarbon group having 6 to 14 carbon atoms, and specifical examples thereof include phenyl, naphthyl, indenyl and anthranyl, among these phenyl being particularly preferred.

The term "heteroaryl" in the above Formula (I) and Formula ($I_0$) denotes an aromatic heterocyclic group containing at least one atom selected from nitrogen atom, oxygen atom and sulfur atom in addition to carbon atoms, and examples thereof include 5- to 7-membered monocyclic heterocyclic groups, and condensed heterocyclic groups in which a 3- to 8-membered ring is condensed with the foregoing monocyclic heterocyclic group, specifically such as thienyl, pyrrolyl, furyl, thiazolyl, imidazolyl, pyrazolyl, oxazolyl, pyridyl, pyrazinyl, pyrimidinyl, pyridazinyl, isoxazolyl, isoquinolyl, isoindolyl, indazolyl, indolyl, quinoxalinyl, quinolyl, benzimidazolyl and benzofuranyl.

The term "5- or 6-membered aromatic heterocyclic group" in the above Formula (I) and Formula ($I_0$) denotes a 5- or 6-membered aromatic cyclic group containing at least one atom selected from nitrogen atom, oxygen atom and sulfur atom in addition to carbon atoms, and examples thereof include thienyl, pyrrolyl, furyl, thiazolyl, imidazolyl, oxazolyl.

The term "5- or 6-membered aliphatic heterocyclic group" in the above Formula (I) and Formula ($I_0$) denotes a 5- or 6-membered aliphatic cyclic group containing at least one atom selected from nitrogen atom, oxygen atom and sulfur atom in addition to carbon atoms, and examples thereof include pyrrolidinyl, piperidinyl, piperazinyl, morpholino, tetrahydrofuranyl, imidazolidinyl, thiomorpholino. Also, in the aliphatic heterocyclic group, the two hydrogen atoms attached to the same carbon atom may be replaced with oxo, and the neighboring carbon atoms forming the aliphatic heterocyclic ring may be a double bond.

The term "cycloalkyl" in the above Formula (I) and Formula ($I_0$) denotes a 3- to 8-membered aliphatic cyclic group such as, for example, cyclopropyl, cyclobutyl, cyclopentyl, cyclohexyl, cycloheptyl and cyclooctyl.

The term "halogen atom" in the above Formula (I) and Formula ($I_O$) is, for example, fluorine atom, chlorine atom, bromine atom or iodine atom. Among them, for example, fluorine atom, chlorine atom or bromine atom is preferred.

The term "lower alkoxy" in the above Formula (I) and Formula ($I_O$) denotes a group in which "lower alkyl" is bonded to oxygen atom, and examples thereof include methoxy, ethoxy, propoxy, isopropoxy, butoxy, isobutoxy, sec-butoxy, tert-butoxy, pentyloxy, neopentyloxy, hexyloxy and isohexyloxy.

The term "lower alkylthio" in the above Formula (I) and Formula ($I_O$) denotes a substituent in which the above-described "lower alkyl" is bonded to sulfur atom, and examples thereof include methylthio, ethylthio and butylthio.

The term "lower alkylsulfonyl" in the above Formula (I) and Formula ($I_O$) denotes a substituent in which the above-described "lower alkyl" is bonded to sulfonyl, and examples thereof include methylsulfonyl, ethylsulfonyl and butylsulfonyl.

The term "lower alkylamino" in the above Formula (I) and Formula ($I_O$) denotes a substituent in which amino is N-substituted with the above-described "lower alkyl", and examples thereof include N-methylamino, N-ethylamino, N-propylamino, N-isopropylamino, N-butylamino, N-isobutylamino, N-tert-butylamino, N-pentylamino and N-hexylamino.

The term "di-lower alkylamino" in the above Formula (I) and Formula ($I_O$) denotes a substituent in which amino is N,N-disubstituted with the above-described "lower alkyl", and examples thereof include N,N-dimethylamino, N,N-diethylamino, N,N-dipropylamino, N,N-diisopropylamino, N,N-dibutylamino, N,N-diisobutylamino, N,N-di-tert-butylamino, N,N-dipentylamino, N,N-dihexylamino, N-ethyl-N-methylamino and N-methyl-N-propylamino.

The term "lower alkanoyl" in the above Formula (I) and Formula ($I_O$) denotes a group in which the above-described "lower alkyl" is bonded to carbonyl, and examples thereof include acetyl, propionyl, butyryl, isobutyryl, valeryl, isovaleryl, pivaloyl and pentanoyl.

The term "lower alkanoylamino" in the above-described Formula (I) and Formula ($I_O$) denotes a group in which the above-described "lower alkanoyl" is bonded to amino, and examples thereof include acetylamino, propionylamino, butyrylamino, isobutyrylamino, valerylamino, isovalerylamino, pivaloylamino and pentanoylamino.

The term "lower alkylcarbamoyl" in the above Formula (I) and Formula ($I_O$) denotes a substituent in which carbamoyl is N-substituted with the above-described "lower alkyl", and examples thereof include N-methylcarbamoyl, N-ethylcarbamoyl, N-propylcarbamoyl, N-isopropylcarbamoyl, N-butylcarbamoyl, N-isobutylcarbamoyl, N-tert-butylcarbamoyl, N-pentylcarbamoyl and N-hexylcarbamoyl.

The term "selective inhibitor of Aurora A" used in the present specification is a compound or a drug which selectively inhibits Aurora A as compared with Aurora B. The "selective inhibitor of Aurora A" is preferably a compound or a drug of which inhibitory activities against Aurora A are at least ten times the activities against Aurora B; and more preferably a compound or a drug of which inhibitory activities against Aurora A are at least hundred times the activities against Aurora B.

Explanation for the term "pharmaceutically acceptable salt of ester thereof" or the term "pharmaceutically acceptable carrier or diluent" used in the specification still will be given later.

The term "treatment of cancer" as used in the specification means inhibition of cancer cell growth by administering an antitumor agent to a cancer patient. Preferably, this treatment enables retrogression of cancer growth, that is, reduction in the measurable cancer size. More preferably, such treatment completely eliminates cancer.

The term "cancer" as used in the specification refers to solid cancer and hematopoietic cancer. Here, examples of solid cancer include cerebral tumor, head and neck cancer, esophageal cancer, thyroid cancer, small cell lung cancer, non-small cell lung cancer, breast cancer, stomach cancer, gallbladder and bile duct cancer, liver cancer, pancreas cancer, colon cancer, rectal cancer, ovarian cancer, chorioepithelioma, uterine cancer, cervical cancer, renal pelvic and ureteral cancer, bladder cancer, prostate cancer, penile cancer, testicular cancer, embryonal cancer, wilms tumor, skin cancer, malignant melanoma, neuroblastoma, osteosarcoma, Ewing's tumor and soft tissue sarcoma. On the other hand, examples of hematopoietic cancer include acute leukemia, chronic lymphatic leukemia, chronic myelocytic leukemia, polycythemia vera, malignant lymphoma, multiple myeloma and non-Hodgkins' lymphoma.

The term "preparation" as used in the specification includes oral preparations and parenteral preparations. Examples of oral preparations include tablets, capsules, powders and granules, while examples of parenteral preparations include sterilized liquid preparations such as solutions or suspensions, specifically injections or drip infusions. Preferably, they are intravenous injections or intravenous drip infusions, and more preferably intravenous drip infusions.

The term "combined preparation" as used in the specification refers to those comprising two or more preparations for simultaneous, separate or sequential administration in the treatment, and such preparation may be a so-called kit type preparation or pharmaceutical composition. The term "combined preparation" also includes those having one or more preparations further combined with the combined preparation comprising two separate preparations used in the treatment of cancer.

The two separate preparations described above can be further combined with, in combination with a pharmaceutically acceptable carrier or diluent, at least one preparation comprising at least one antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, interferons, biological response modifiers and other antitumor agents (here, definition of each antitumor agent is the same as that defined above), or a pharmaceutically acceptable salt or ester thereof. In this case, the above-mentioned at least one preparation that has been further combined can be administered simultaneously, separately or sequentially with respect to the two separate preparations. For example, a combined preparation comprising three preparations may include that is comprised of a preparation including a preparation containing the compound represented by the above Formula (I), a preparation containing 5-fluorouracil and a preparation containing leucovorin.

Here, in the above-mentioned combined preparation, either or both of the two separate preparations may be parenteral preparations, preferably injections or drip infusions, and more preferably intravenous drip infusions.

The term "preparation" according to the invention may usually comprise a therapeutically effective amount of a compound according to the invention, together with a pharmaceutically acceptable carrier or diluent. This technique of formulation is considered to be a technical common knowledge to those having ordinary skill in the pertinent art and is well known. Preferably, intravenous drip infusions or injections can be prepared in combination with a pharmaceutically acceptable carrier or diluent, by various methods that are well known in the art.

In the case of using the combined preparation according to the invention, the term "administration" as used in the present specification refers to parenteral administration and/or oral administration, and preferably parenteral administration. Thus, when a combined preparation is administered, both administrations may be parenteral; one administration may be parenteral while the other may be oral; or both administrations may be oral. Preferably, both preparations in the combined preparation are administered parenterally. Here, the term "parenteral administration" is, for example, intravenous administration, subcutaneous administration or intramuscular administration, and preferably it is intravenous administration. Even when three or more preparations are combined and administered, at least one preparation may be parenterally administered, preferably intravenously administered, and more preferably intravenously infused or intravenously injected.

In the embodiment of the present invention, a compound represented by the above Formula (I) may be administered simultaneously with other antitumor agent(s). Further, it is possible to administer the compound represented by the above Formula (I) first and then another antitumor agent consecutively, or alternatively it is possible to administer another antitumor agent first and then the compound represented by the above Formula (I) consecutively. It is also possible to administer the compound represented by the above Formula (I) first and then separately administer another antitumor agent after a while, or alternatively it is possible to administer another antitumor agent first and then separately administer the compound represented by the above Formula (I) after a while. The order and the time interval for the administration may be appropriately selected by a person skilled in the art in accordance with, for example, a preparation containing the compound represented by the above Formula (I) used and a preparation containing an antitumor agent that is used in combination therewith, the type of the cancer cells to be treated and the condition of the patient. For example, in the case of administering the compound represented by the above Formula (I) and paclitaxel, preferably paclitaxel is administered first, and then the compound represented by the above Formula (I) is administered sequentially or separately after a while.

The term "simultaneously" as used in the specification refers to the use of preparations for the treatment substantially at the same time, whereas the term "separately" refers to the separate use of preparations for the treatment at different times such that, for example, one agent is used on the first day and another agent is used on the second day for the treatment. The term "sequentially" refers to the use of preparations in such an order that, for example, one agent is first used and another agent is used after a predetermined period of time for the treatment.

The term "antitumor alkylating agent" as used in the present specification refers to an alkylating agent having antitumor activity, and the term "alkylating agent" herein generally refers to an agent giving an alkyl group in the alkylation reaction in which a hydrogen atom of an organic compound is substituted with an alkyl group. The term "antitumor alkylating agent" may be exemplified by nitrogen mustard N-oxide, cyclophosphamide, ifosfamide, melphalan, busulfan, mitobronitol, carboquone, thiotepa, ranimustine, nimustine, temozolomide or carmustine.

The term "antitumor antimetabolite" as used in the specification refers to an antimetabolite having antitumor activity, and the term "antimetabolite" herein includes, in a broad sense, substances which disturb normal metabolism and substances which inhibit the electron transfer system to prevent the production of energy-rich intermediates, due to their structural or functional similarities to metabolites that are important for living organisms (such as vitamins, coenzymes, amino acids and saccharides). The term "antitumor antimetabolites" may be exemplified methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine or pemetrexed disodium, and preferred are 5-fluorouracil, S-1, gemcitabine and the like.

The term "antitumor antibiotic" as used in the specification refers to an antibiotic having antitumor activity, and the "antibiotic" herein includes substances that are produced by microorganisms and inhibit cell growth and other functions of microorganisms and of other living organisms. The term "antitumor antibiotic" may be exemplified by actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus or valrubicin.

The term "plant-derived antitumor agent" as used in the specification includes compounds having antitumor activities which originate from plants, or compounds prepared by applying chemical modification to the foregoing compounds. The term "plant-derived antitumor agent" may be exemplified by vincristine, vinblastine, vindesine, etoposide, sobuzoxane, docetaxel, paclitaxel and vinorelbine, and preferred and docetaxel and paclitaxel.

The term "antitumor camptothecin derivative" as used in the specification refers to compounds that are structurally related to camptothecin and inhibit cancer cell growth, including camptothecin per se. The term "antitumor camptothecin derivative" is not particularly limited to, but may be exemplified by, camptothecin, 10-hydroxycamptothecin, topotecan, irinotecan or 9-aminocamptothecin, with camptothecin, topotecan and irinotecan being preferred. Further, irinotecan is metabolized in vivo and exhibits antitumor effect as SN-38. The action mechanism and the activity of the camptothecin derivatives are believed to be virtually the same as those of camptothecin (e.g., Nitta, et al., *Gan to Kagaku Ryoho*, 14, 850-857 (1987)).

The term "antitumor platinum coordination compound" as used in the specification refers to a platinum coordination compound having antitumor activity, and the term "platinum coordination compound" herein refers to a platinum coordination compound which provides platinum in ion form. Preferred platinum compounds include cisplatin; cis-diamminediaquoplatinum (II)-ion; chloro(diethylenetriamine)-platinum (II) chloride; dichloro(ethylenediamine)-platinum (II); diammine(1,1-cyclobutanedicarboxylato) platinum (II) (carboplatin); spiroplatin; iproplatin; diammine(2-ethylmalonato)platinum (II); ethylenediaminemalonatoplatinum (II); aqua(1,2-diaminodicyclohexane)sulfatoplatinum (II); aqua (1,2-diaminodicyclohexane)malonatoplatinum (II); (1,2-diaminocyclohexane)malonatoplatinum (II); (4-carboxyphthalato)(1,2-diaminocyclohexane) platinum (II); (1,2-diaminocyclohexane)-(isocitrato)platinum (II); (1,2-diaminocyclohexane)oxalatoplatinum (II); ormaplatin; tetraplatin; carboplatin, nedaplatin and oxaliplatin, and preferred is carboplatin or oxaliplatin. Further, other antitumor platinum coordination compounds mentioned in the specification are known and are commercially available and/or producible by a person having ordinary skill in the art by conventional techniques.

The term "antitumor tyrosine kinase inhibitor" as used in the specification refers to a tyrosine kinase inhibitor having antitumor activity, and the term "tyrosine kinase inhibitor" herein refers to a chemical substance inhibiting "tyrosine kinase" which transfers a γ-phosphate group of ATP to a hydroxyl group of a specific tyrosine in protein. The term "antitumor tyrosine kinase inhibitor" may be exemplified by gefitinib, imatinib, sorafenib, sunitinib, dasatinib, or erlotinib.

The term "monoclonal antibody" as used in the specification, which is also known as single clonal antibody, refers to an antibody produced by a monoclonal antibody-producing cell, and examples thereof include cetuximab, bevacizumab, rituximab, alemtuzumab and trastuzumab.

The term "interferon" as used in the specification refers to an interferon having antitumor activity, and it is a glycoprotein having a molecular weight of about 20,000 which is produced and secreted by most animal cells upon viral infection. It has not only the effect of inhibiting viral growth but also various immune effector mechanisms including inhibition of growth of cells (in particular, tumor cells) and enhancement of the natural killer cell activity, thus being designated as one type of cytokine. Examples of "interferon" include interferon α, interferon α-2a, interferon α-2b, interferon β, interferon γ-1a and interferon γ-n1.

The term "biological response modifier" as used in the specification is the so-called biological response modifier or BRM and is generally the generic term for substances or drugs for modifying the defense mechanisms of living organisms or biological responses such as survival, growth or differentiation of tissue cells in order to direct them to be useful for an individual against tumor, infection or other diseases. Examples of the "biological response modifier" include krestin, lentinan, sizofuran, picibanil and ubenimex.

The term "other antitumor agent" as used in the specification refers to an antitumor agent which does not belong to any of the above-described agents having antitumor activities. Examples of the "other antitumor agent" include mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, and goserelin.

The above-described terms "antitumor alkylating agent", "antitumor antimetabolite", "antitumor antibiotic", "plant-derived antitumor agent", "antitumor platinum coordination compound", "antitumor camptothecin derivative", "antitumor tyrosine kinase inhibitor", "monoclonal antibody", "interferon", "biological response modifier" and "other antitumor agent" are all known and are either commercially available or producible by a person skilled in the art by methods known per se or by well-known or conventional methods. The process for preparation of gefitinib is described, for example, in U.S. Pat. No. 5,770,599; the process for preparation of cetuximab is described, for example, in WO 96/40210; the process for preparation of bevacizumab is described, for example, in WO 94/10202; the process for preparation of oxaliplatin is described, for example, in U.S. Pat. Nos. 5,420,319 and 5,959,133; the process for preparation of gemcitabine is described, for example, in U.S. Pat. Nos. 5,434,254 and 5,223,608; and the process for preparation of camptothecin is described in U.S. Pat. Nos. 5,162,532, 5,247,089, 5,191,082, 5,200,524, 5,243,050 and 5,321,140; the process for preparation of irinotecan is described, for example, in U.S. Pat. No. 4,604,463; the process for preparation of topotecan is described, for example, in U.S. Pat. No. 5,734,056; the process for preparation of temozolomide is described, for example, in JP-B No. 4-5029; and the process for preparation of rituximab is described, for example, in JP-W No. 2-503143.

The above-mentioned antitumor alkylating agents are commercially available, as exemplified by the following: nitrogen mustard N-oxide from Mitsubishi Pharma Corp. as Nitromin (tradename); cyclophosphamide from Shionogi & Co., Ltd. as Endoxan (tradename); ifosfamide from Shionogi & Co., Ltd. as Ifomide (tradename); melphalan from GlaxoSmithKline Corp. as Alkeran (tradename); busulfan from Takeda Pharmaceutical Co., Ltd. as Mablin (tradename); mitobronitol from Kyorin Pharmaceutical Co., Ltd. as Myebrol (tradename); carboquone from Sankyo Co., Ltd. as Esquinon (tradename); thiotepa from Sumitomo Pharmaceutical Co., Ltd. as Tespamin (tradename); ranimustine from Mitsubishi Pharma Corp. as Cymerin (tradename); nimustine from Sankyo Co., Ltd. as Nidran (tradename); temozolomide from Schering Corp. as Temodar (tradename); and carmustine from Guilford Pharmaceuticals Inc. as Gliadel Wafer (tradename).

The above-mentioned antitumor antimetabolites are commercially available, as exemplified by the following: methotrexate from Takeda Pharmaceutical Co., Ltd. as Methotrexate (tradename); 6-mercaptopurine riboside from Aventis Corp. as Thioinosine (tradename); mercaptopurine from Takeda Pharmaceutical Co., Ltd. as Leukerin (tradename); 5-fluorouracil from Kyowa Hakko Kogyo Co., Ltd. as 5-FU (tradename); tegafur from Taiho Pharmaceutical Co., Ltd. as Futraful (tradename); doxyfluridine from Nippon Roche Co., Ltd. as Furutulon (tradename); carmofur from Yamanouchi Pharmaceutical Co., Ltd. as Yamafur (tradename); cytarabine from Nippon Shinyaku Co., Ltd. as Cylocide (tradename); cytarabine ocfosfate from Nippon Kayaku Co., Ltd. as Strasid (tradename); enocitabine from Asahi Kasei Corp. as Sanrabin (tradename); S-1 from Taiho Pharmaceutical Co., Ltd. as TS-1 (tradename); gemcitabine from Eli Lilly & Co. as Gemzar (tradename); fludarabine from Nippon Schering Co., Ltd. as Fludara (tradename); and pemetrexed disodium from Eli Lilly & Co. as Alimta (tradename).

The above-mentioned antitumor antibiotics are commercially available, as exemplified by the following: actinomycin D from Banyu Pharmaceutical Co., Ltd. as Cosmegen (tradename); doxorubicin from Kyowa Hakko Kogyo Co., Ltd. as adriacin (tradename); daunorubicin from Meiji Seika Kaisha Ltd. as Daunomycin; neocarzinostatin from Yamanouchi Pharmaceutical Co., Ltd. as Neocarzinostatin (tradename); bleomycin from Nippon Kayaku Co., Ltd. as Bleo (tradename); pepromycin from Nippon Kayaku Co, Ltd. as Pepro (tradename); mitomycin C from Kyowa Hakko Kogyo Co., Ltd. as Mitomycin (tradename); aclarubicin from Yamanouchi Pharmaceutical Co., Ltd. as Aclacinon (tradename); pirarubicin from Nippon Kayaku Co., Ltd. as Pinorubicin (tradename); epirubicin from Pharmacia Corp. as Pharmorubicin (tradename); zinostatin stimalamer from Yamanouchi Pharmaceutical Co., Ltd. as Smancs (tradename); idarubicin from Pharmacia Corp. as Idamycin (tradename); sirolimus from Wyeth Corp. as Rapamune (tradename); and valrubicin from Anthra Pharmaceuticals Inc. as Valstar (tradename).

The above-mentioned plant-derived antitumor agents are commercially available, as exemplified by the following: vincristine from Shionogi & Co., Ltd. as Oncovin (tradename); vinblastine from Kyorin Pharmaceutical Co., Ltd. as Vinblastine (tradename); vindesine from Shionogi & Co., Ltd. as Fildesin (tradename); etoposide from Nippon Kayaku Co., Ltd. as Lastet (tradename); sobuzoxane from Zenyaku Kogyo Co., Ltd. as Perazolin (tradename); docetaxel from Aventis Corp. as Taxsotere (tadename); paclitaxel from Bristol-Myers Squibb Co. as Taxol (tradename); and vinorelbine from Kyowa Hakko Kogyo Co., Ltd. as Navelbine (tradename).

The above-mentioned antitumor platinum coordination compounds are commercially available, as exemplified by the following: cisplatin from Nippon Kayaku Co., Ltd. as Randa (tradename); carboplatin from Bristol-Myers Squibb Co. as Paraplatin (tradename); nedaplatin from Shionogi & Co., Ltd. as Aqupla (tradename); and oxaliplatin from Sanofi-Synthelabo Co. as Eloxatin (tradename).

The above-mentioned antitumor camptothecin derivatives are commercially available, as exemplified by the following: irinotecan from Yakult Honsha Co., Ltd. as Campto (tradename); topotecan from GlaxoSmithKline Corp. as Hycamtin (tradename); and camptothecin from Aldrich Chemical Co., Inc., U.S.A.

The above-mentioned antitumor tyrosine kinase inhibitors are commercially available, as exemplified by the following: gefitinib from AstraZeneca Corp. as Iressa (tradename); imatinib from Novartis AG as Gleevec (tradename); sorafenib from Bayer as Nexavar (tradename); sunitinib from Pfizer as Sutent (tradename); dasatinib from Bristol Myers Squibb as Sprycel (tradename); and erlotinib from OSI Pharmaceuticals Inc. as Tarceva (tradename).

The above-mentioned monoclonal antibodies are commercially available, as exemplified by the following: cetuximab from Bristol-Myers Squibb Co. as Erbitux (tradename); bevacizumab from Genentech, Inc. as Avastin (tradename); rituximab from Biogen Idec Inc. as Rituxan (tradename); alemtuzumab from Berlex Inc. as Campath (tradename); and trastuzumab from Chugai Pharmaceutical Co., Ltd. as Herceptin (tradename).

The above-mentioned interferons are commercially available, as exemplified by the following: interferon α from Sumitomo Pharmaceutical Co., Ltd. as Sumiferon (tradename); interferon α-2a from Takeda Pharmaceutical Co., Ltd. as Canferon-A (tradename); interferon α-2b from Schering-Plough Corp. as Intron A (tradename); interferon β from Mochida Pharmaceutical Co., Ltd. as IFNβ (tradename); interferon γ-1a from Shionogi & Co., Ltd. as Immunomax-γ (tradename); and interferon γ-n1 from Otsuka Pharmaceutical Co., Ltd. as Ogamma (tradename).

The above-mentioned biological response modifiers are commercially available, as exemplified by the following: krestin from Sankyo Co., Ltd. as krestin (tradename); lentinan from Aventis Corp. as Lentinan (tradename); sizofuran from Kaken Seiyaku Co., Ltd. as Sonifuran (tradename); picibanil from Chugai Pharmaceutical Co., Ltd. as Picibanil (tradename); and ubenimex from Nippon Kayaku Co., Ltd. as Bestatin (tradename).

The above-mentioned other antitumor agents are commercially available, as exemplified by the following: mitoxantrone from Wyeth Lederle Japan, Ltd. as Novantrone (tradename); L-asparaginase from Kyowa Hakko Kogyo Co., Ltd. as Leunase (tradename); procarbazine from Nippon Roche Co., Ltd. as Natulan (tradename); dacarbazine from Kyowa Hakko Kogyo Co., Ltd. as Dacarbazine (tradename); hydroxycarbamide from Bristol-Myers Squibb Co. as Hydrea (tradename); pentostatin from Kagaku Oyobi Kessei Ryoho Kenkyusho as Coforin (tradename); tretinoin from Nippon Roche Co., Ltd. As Vesanoid (tradename); alefacept from Biogen Idec Inc.; as Amevive (tradename); darbepoetin alfa from Amgen Inc. as Aranesp (tradename); anastrozole from AstraZeneca Corp. as Arimidex (tradename); exemestane from Pfizer Inc. as Aromasin (tradename); bicalutamide from AstraZeneca Corp. as Casodex (tradename); leuprorelin from Takeda Pharmaceutical Co., Ltd. as Leuplin (tradename); flutamide from Schering-Plough Corp. as Eulexin (tradename); fulvestrant from AstraZeneca Corp. as Faslodex (tradename); pegaptanib octasodium from Gilead Sciences, Inc. as Macugen (tradename); denileukin diftitox from Ligand Pharmaceuticals Inc. as Ontak (tradename); aldesleukin from Chiron Corp. as Proleukin (tradename); thyrotropin alfa from Genzyme Corp. as Thyrogen (tradename); arsenic trioxide from Cell Therapeutics, Inc. as Trisenox (tradename); bortezomib from Millennium Pharmaceuticals, Inc. as Velcade (tradename); capecitabine from Hoffmann-La Roche, Ltd. as Xeloda (tradename); and goserelin from AstraZeneca Corp. as Zoladex (tradename).

The term "antitumor agent" as used in the specification includes the above-described "antitumor alkylating agent", "antitumor antimetabolite", "antitumor antibiotic", "plant-derived antitumor agent", "antitumor platinum coordination compound", "antitumor camptothecin derivative", "antitumor tyrosine kinase inhibitor", "monoclonal antibody", "interferon", "biological response modifier" and "other antitumor agent".

The term "aminopyridine derivative" as used in the specification includes, but is not limited to, any compound having a pyridyl group or a pyridine analogue group, any of which is substituted with an amino group. It is exemplified by a compound of the above General Formula (I), preferably a compound of the above General Formula ($I_0$), and more preferably any one compound of the below-mentioned (a) to (e): a compound which is:

(a) 2-(((1S,4S)-5-(2-fluoro-3-(trifluoromethyl)benzoyl)-2,5-diazabicyclo[2.2.1]hept-2-yl)methyl)-N-1H-pyrazol-3-ylpyrimidine-4-amine (Example 6);

(b) 2-(((1S,4S)-5-(3-chloro-2-fluorobenzoyl)-2,5-diazabicyclo[2.2.1]hept-2-yl)methyl)-N-(5-methyl-1H-pyrazol-3-yl)pyrimidine-4-amine (Example 9);

(c) 2-(((1S,4S)-5-(3-chloro-2-fluorobenzoyl)-2,5-diazabicyclo[2.2.1]hept-2-yl)methyl) -6-methyl-N-1H-pyrazol-3-ylpyrimidine-4-amine (Example 1);

(d) 2-(((1S,4S)-5-(3-chloro-2-fluorobenzoyl)-2,5-diazabicyclo[2.2.1]hept-2-yl)methyl)-N,N-dimethyl-6-(1,3-thiazol-2-ylamino)isonicotinamide (Example 21); or (e) 6-(((1S,4S)-5-(2,3-dichlorobenzoyl)-2,5-diazabicyclo[2.2.1]hept-2-yl)methyl) -N-1H-pyrazol-3-ylpyrazin-2-amine (Example 10), or a pharmaceutically acceptable salt or ester thereof.

Embodiments of the compound represented by the above General Formula (I) will be illustrated in more detail.

$n_1$ is 0 or 1; and preferably $n_1$ is 0.

$n_2$ is 0 or 1; and preferably $n_2$ is 0.

R is aryl, heteroaryl or cycloaryl, any of which may be substituted.

R is preferably phenyl, or a 5- or 6-membered aromatic heterocyclic group containing at least one atom selected from N, O and S (wherein the phenyl or aromatic heterocyclic group may be substituted with one or more of identical or different substituents selected from:

1) lower alkyl, 2) a substituent selected from <Substituent group $A_2$>, and 3) lower alkyl which is substituted with one or more of identical or different substituents selected from <Substituent group $A_2$>), wherein:

<Substituent group $A_2$> consists of halogen atom, cyano, hydroxyl, amino, lower alkylamino, di-lower alkylamino, lower alkanoyl, lower alkanoylamino, carbamoyl, lower alkylcarbamoyl and lower alkylsulfonyl. Here, when R is a 5-membered aromatic heterocyclic group, preferred are, for example, pyrrolyl, furyl, thienyl, thiazolyl, pyrazolyl, pyridyl and pyrazinyl, any of which may be appropriately substituted.

R is more preferably phenyl of which $2^{nd}$ and $3^{rd}$ positions are substituted with two substituents, which are the same or different, selected from halogen atom, methyl that may be substituted with one to three halogen atoms, and cyano.

R is particularly preferably phenyl which is substituted with identical or different halogen atoms at the 2- and 3-positions, or alternatively phenyl which is substituted with halogen atom, and methyl substituted with one to three of identical or different halogen atoms at the 2- and 3-positions, respectively.

$R_e$ are hydrogen atom or lower alkyl which may be substituted; $R_e$ is preferably hydrogen atom.

With regard to $R_{a1}$, $R_{a1}'$, $R_{a2}$, $R_{a2}'$, $R_{b1}$, $R_{b1}'$, $R_{b2}$ and $R_{b2}'$, two groups selected from four groups consisting of (i) either one of $R_{a1}$ and $R_{a1}'$, (ii) either one of $R_{a2}$ and $R_{a2}'$, (iii) either one of $R_{b1}$ and $R_{b1}'$, and (iv) either one of $R_{b2}$ and $R_{b2}'$, are combined to form $-(CH_2)_n-$ where n is 1, 2 or 3; and among $R_{a1}$ and $R_{a1}'$, $R_{a2}$, $R_{a2}'$, $R_{b1}$, $R_{b1}'$, $R_{b2}$ and $R_{b2}'$, the groups which do not form $-(CH_2)_n-$ are each independently hydrogen atom or lower alkyl which may be substituted.

Preferably, with regard to $R_{a1}$, $R_{a1}'$, $R_{a2}$, $R_{a2}'$, $R_{b1}$, $R_{b1}'$, $R_{b2}$ and $R_{b2}'$, (i) either one of $R_{a1}$ and $R_{a1}'$, and (ii) either one of $R_{b2}$ and $R_{b2}'$, are combined to form $-(CH_2)_n-$ where n is 1, 2 or 3; and among $R_{a1}$, $R_{a1}'$, $R_{a2}$, $R_{a2}'$, $R_{b1}$, $R_{b1}'$, $R_{b2}$ and $R_{b2}'$, the groups which do not form $-(CH_2)_n-$ are each independently hydrogen atom or lower alkyl which may be substituted; or (i) either one of $R_{a2}$ and $R_{a2}'$, and (ii) either one of $R_{b1}$ and $R_{b1}'$, are combined to form $-(CH_2)_n-$ where n is 1, 2 or 3; and among $R_{a1}$ and $R_{a1}'$, $R_{a2}$, $R_{a2}'$, $R_{b1}$, $R_{b1}'$, $R_{b2}$ and $R_{b2}'$, the groups which do not form $-(CH_2)_n-$ are each independently hydrogen atom or lower alkyl which may be substituted.

More preferably, with regard to $R_{a1}$, $R_{a1}'$, $R_{a2}$, $R_{a2}'$, $R_{b1}$, $R_{b1}'$, $R_{b2}$ and $R_{b2}'$, (i) either one of $R_{a1}$ and $R_{a1}'$, and (ii) either one of $R_{b2}$ and $R_{b2}'$, are combined to form $-CH_2-$; and among $R_{a1}$, $R_{a1}'$, $R_{a2}$, $R_{a2}'$, $R_{b1}$, $R_{b1}'$, $R_{b2}$ and $R_{b2}'$, the groups which do not form $-CH_2-$ are each independently hydrogen atom or lower alkyl which may be substituted; or (i) either one of $R_{a2}$ and $R_{a2}'$, and (ii) either one of $R_{b1}$ and $R_{b1}'$, are combined to form $-CH_2-$; and among $R_{a1}$, $R_{a1}'$, $R_{a2}$, $R_{a2}'$, $R_{b1}$, $R_{b1}'$, $R_{b2}$ and $R_{b2}'$, the groups which do not form $-CH_2-$ are each independently hydrogen atom or lower alkyl which may be substituted.

With regard to $R_{a1}$, $R_{a1}'$, $R_{a2}$, $R_{a2}'$, $R_{b1}$, $R_{b1}'$, $R_{b2}$ and $R_{b2}'$, a preferred embodiment is illustrated as follows:

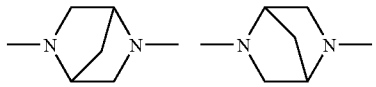

Please note that the diazabicyclo ring in the above Formula (I) and Formula ($I_0$) includes all possible stereoisomers.

$X_1$ is CH, $CX_{1a}$ or N, wherein $X_{1a}$ is lower alkyl which may be substituted. $X_1$ is preferably CH or N.

$X_2$ is CH, $CX_{2a}$ or N (wherein:

$X_{2a}$ is lower alkyl; or $X_{2a}$ is a substituent selected from <Substituent group $A_1$>, or lower alkyl which is substituted with one or more of identical or different substituents selected from <Substituent group $A_1$> (wherein <Substituent group $A_1$> consists of halogen atom; cyano; hydroxyl; lower alkylamino; di-lower alkylamino; lower alkoxy which may be substituted with one or more hydroxyl groups; lower alkylthio; and lower alkylsulfonyl); or $X_{2a}$ is $COOR_1$, or $CONR_2R_3$ (wherein:

$R_1$ is hydrogen atom or lower alkyl which may be substituted; and $R_2$ and $R_3$, which may be identical or different, are each hydrogen atom, lower alkyl which may be substituted, or cycloalkyl, which may be substituted, or alternatively $R_2$ and $R_3$ together with the nitrogen atom to which they bond, form a 5- or 6-membered aliphatic heterocyclic group which contains at least one atom selected from N, O and S and which may be substituted); or $X_{2a}$ is a 3- to 6-membered cycloalkyl group which may be substituted (wherein two hydrogen atoms that are bonded to the same carbon atom of the cycloalkyl group may be substituted with oxo and neighboring two carbon atoms constituting the cycloalkyl ring may be double-bonded), or lower alkyl which is substituted with the cycloalkyl group.

$X_2$ is preferably CH, $CX_{2a}$ or N (wherein:

$X_{2a}$ is lower alkyl, halogen atom, $CONR_2R_3$ (wherein $R_2$ and $R_3$, which may be identical or different, are each hydrogen, atom or lower alkyl which may be substituted) or 3- to 6-membered cycloalkyl group which may be substituted.

$X_3$ is CH, $CX_{3a}$ or N (wherein $X_{3a}$ is lower alkyl which may be substituted); $X_3$ is preferably CH.

$X_4$ is CH or N, and preferably N.

The number of nitrogen atoms among $X_1$, $X_2$ and $X_3$ and $X_4$ is one or two; preferably $X_4$ is N, while the number of N among $X_1$ to $X_3$ is at most 1.

Preferable combinations of $X_1$, $X_2$ and $X_3$ and $X_4$ are: $X_4$ is N; and $X_1$ is CH, $X_2$ is CH or $CX_{2a}$, and $X_3$ is CH; or
$X_1$ is N, $X_2$ is CH or $CX_{2a}$, and $X_3$ is CH; or
$X_1$ is CH, $X_2$ is N, and $X_3$ is CH.

$Y_1$, $Y_2$ and $Y_3$, which may be identical or different, are each CH or N, provided that if $Y_1$ is CH and $R_e$ is hydrogen atom, then the two hydrogen atoms may be substituted with oxo.

$Y_1$ is preferably CH.

W is the following group:

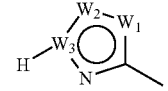

wherein:

$W_1$ is CH, N, NH, O or S;

$W_2$ is CH, $CW_{2a}$, N, $NW_{2b}$, O or S (wherein $W_{2a}$ and $W_{2b}$, which may be identical or different, are each hydrogen atom, halogen atom, cyano, lower alkyl having one to two carbon atoms, cycloalkyl having three to five carbon atoms, or lower alkyl having one to two carbon atoms, which may be substituted with one or more halogen atoms);

$W_3$ is C or N; and

At least one of $W_1$, $W_2$ and $W_3$ is carbon atom; however, two of $W_1$, $W_2$ and $W_3$ are not simultaneously O and S.

W is preferably selected from the following:

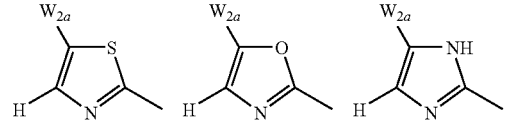

-continued

W is more preferably selected from the following:

wherein W$_{2a}$ is hydrogen atom, halogen atom, cyano, or methyl which may be substituted with one to three fluorine atoms.

W is particularly preferably selected from the following:

As mentioned above, a preferred embodiment of a compound of the above Formula (I) is a compound of the above Formula (I$_0$). A preferred embodiment of the compound of the above Formula (I$_0$) can be also expressed as follows:

(1) The compound of the above Formula (I$_0$) or a pharmaceutically acceptable salt or ester thereof, wherein W is selected from:

-continued (2) The compound as described in the above (1) or a pharmaceutically acceptable salt or ester thereof, wherein:
  n$_1$ is 0;
  n$_2$ is 0; and
  R is phenyl or a 5- or 6-membered aromatic heterocyclic group which contains at least one atom selected from N, O, and S, wherein the phenyl or aromatic heterocyclic group may be substituted with one or more of the same or different substituents selected from the following:
  1) lower alkyl;
  2) a substituent selected from <substituent group A$_2$>; and
  3) lower alkyl which is substituted with one or more of the same or different substituents selected from <substituent group A$_2$>, wherein:
    <substituent group A$_2$> is halogen atom, cyano, hydroxyl, amino, lower alkyl amino, di-lower alkyl amino, lower alkanoyl, lower alkanoylamino, carbamoyl, lower alkyl carbamoyl, and lower alkyl sulfonyl; or (3) The compound as described in the above (2) or a pharmaceutically acceptable salt or ester thereof, wherein Y$_1$ is CH and R$_e$ is hydrogen atom; or (4) The compound as described in the above (3) or a pharmaceutically acceptable salt or ester thereof, wherein:
  X$_4$ is N and the number of nitrogen atom among X$_1$, X$_2$, and X$_3$ is at most one; and
  R is phenyl of which 2$^{nd}$ and 3$^{rd}$ positions are substituted with two substituents, which are the same or different, selected from halogen atom, methyl that may be substituted with one to three halogen atoms, and cyano; or (5) The compound as described in the above (4) or a pharmaceutically acceptable salt or ester thereof, wherein:
  W is selected from:

wherein W$_{2a}$ is hydrogen atom, halogen atom, cyano, or methyl which may be substituted with one to three fluorine atoms; or (6) The compound as described in the above (5) or a pharmaceutically acceptable salt or ester thereof, wherein:
  X$_1$ is CH, X$_2$ is CH or CX$_{2a}$, and X$_3$ is CH; or
  X$_1$ is N, X$_2$ is CH or CX$_{2a}$, and X$_3$ is CH; or
  X$_1$ is CH, X$_2$ is N, and X$_3$ is CH; and
  X$_{2a}$ is lower alkyl; halogen atom; CONR$_2$R$_3$ wherein R$_2$ and R$_3$ are each independently hydrogen atom or lower alkyl that may be substituted; or 3- to 6-membered cycloalkyl that may be substituted; or (7) The compound as described in the above (6) or a pharmaceutically acceptable salt or ester thereof, wherein R is phenyl of which 2nd and 3 positions are substituted with the same or different halogen atoms, or alternatively R is phenyl of which $2^{nd}$ and $3^{rd}$ positions are substituted with halogen atom and methyl substituted with one to three halogen atoms, respectively; or (8) A compound which is:
  (a) 2-(((1S,4S)-5-(2-fluoro-3-(trifluoromethyl)benzoyl)-2,5-diazabicyclo[2.2.1]hept-2-yl)methyl)-N-1H-pyrazol-3-ylpyrimidine-4-amine;
  (b) 2-(((1S,4S)-5-(3-chloro-2-fluorobenzoyl)-2,5-diazabicyclo[2.2.1]hept-2-yl)methyl)-N-(5-methyl-1H-pyrazol-3-yl)pyrimidine-4-amine;
  (c) 2-(((1S,4S)-5-(3-chloro-2-fluorobenzoyl)-2,5-diazabicyclo[2.2.1]hept-2-yl)methyl) -6-methyl-N-1H-pyrazol-3-ylpyrimidine-4-amine;
  (d) 2-(((1S,4S)-5-(3-chloro-2-fluorobenzoyl)-2,5-diazabicyclo[2.2.1]hept-2-yl)methyl)-N,N-dimethyl-6-(1,3-thiazol-2-ylamino)isonicotinamide; or
  (e) 6-(((1S,4S)-5-(2,3-dichlorobenzoyl)-2,5-diazabicyclo[2.2.1]hept-2-yl)methyl) -N-1H-pyrazol-3-ylpyrazin-2-amine, or a pharmaceutically acceptable salt or ester thereof.

Further, in the combined preparation comprising two separate preparations according to the invention, preferably either or both of the two separate preparations are parenteral preparations, and more preferably either or both of the two separate preparations are injections or drip infusions.

The combined preparation comprising two separate preparations according to the invention is preferably such that one of the preparations is a preparation containing the following:
  (a) 2-(((1S,4S)-5-(2-fluoro-3-(trifluoromethyl)benzoyl)-2,5-diazabicyclo[2.2.1]hept-2-yl)methyl)-N-1H-pyrazol-3-ylpyrimidine-4-amine;
  (b) 2-(((1S,4S)-5-(3-chloro-2-fluorobenzoyl)-2,5-diazabicyclo[2.2.1]hept-2-yl)methyl)-N-(5-methyl-1H-pyrazol-3-yl)pyrimidine-4-amine;
  (c) 2-(((1S,4S)-5-(3-chloro-2-fluorobenzoyl)-2,5-diazabicyclo[2.2.1]hept-2-yl)methyl) -6-methyl-N-1H-pyrazol-3-ylpyrimidine-4-amine;
  (d) 2-(((1S,4S)-5-(3-chloro-2-fluorobenzoyl)-2,5-diazabicyclo[2.2.1]hept-2-yl)methyl)-N,N-dimethyl-6-(1,3-thiazol-2-ylamino)isonicotinamide; or
  (e) 6-(((1S,4S)-5-(2,3-dichlorobenzoyl)-2,5-diazabicyclo[2.2.1]hept-2-yl)methyl) -N-1H-pyrazol-3-ylpyrazin-2-amine, or a pharmaceutically acceptable salt or ester thereof; and the other preparation is a preparation containing paclitaxel or docetaxel, or a pharmaceutically acceptable salt or ester thereof, together with a pharmaceutically acceptable carrier or diluent.

In another embodiment, the combined preparation comprising two separate preparations according to the invention is more preferably such that one of the preparations is a preparation containing the following:
  (a) 2-(((1S,4S)-5-(2-fluoro-3-(trifluoromethyl)benzoyl)-2,5-diazabicyclo[2.2.1]hept-2-yl)methyl)-N-1H-pyrazol-3-ylpyrimidine-4-amine;
  (b) 2-(((1S,4S)-5-(3-chloro-2-fluorobenzoyl)-2,5-diazabicyclo[2.2.1]hept-2-yl)methyl)-N-(5-methyl-1H-pyrazol-3-yl)pyrimidine-4-amine;
  (c) 2-(((1S,4S)-5-(3-chloro-2-fluorobenzoyl)-2,5-diazabicyclo[2.2.1]hept-2-yl)methyl) -6-methyl-N-1H-pyrazol-3-ylpyrimidine-4-amine;
  (d) 2-(((1S,4S)-5-(3-chloro-2-fluorobenzoyl)-2,5-diazabicyclo[2.2.1]hept-2-yl)methyl)-N,N-dimethyl-6-(1,3-thiazol-2-ylamino)isonicotinamide; or
  (e) 6-(((1S,4S)-5-(2,3-dichlorobenzoyl)-2,5-diazabicyclo[2.2.1]hept-2-yl)methyl) -N-1H-pyrazol-3-ylpyrazin-2-amine, or a pharmaceutically acceptable salt or ester thereof; and the other preparation is a preparation containing paclitaxel or docetaxel, or a pharmaceutically acceptable salt or ester thereof, together with a pharmaceutically acceptable carrier or diluent.

Moreover, the combined preparation comprising, together with a pharmaceutically acceptable carrier or diluent, two separate preparations according to the invention may be further combined with at least one preparation containing an antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, interferons, biological response modifiers and other antitumor agents (here, definition of each antitumor agent is the same as that defined above), or a pharmaceutically acceptable salt or ester thereof.

Also, the pharmaceutical composition according to the invention preferably contains the following:
  (a) 2-(((1S,4S)-5-(2-fluoro-3-(trifluoromethyl)benzoyl)-2,5-diazabicyclo[2.2.1]hept-2-yl)methyl)-N-1H-pyrazol-3-ylpyrimidine-4-amine;
  (b) 2-(((1S,4S)-5-(3-chloro-2-fluorobenzoyl)-2,5-diazabicyclo[2.2.1]hept-2-yl)methyl)-N-(5-methyl-1H-pyrazol-3-yl)pyrimidine-4-amine;
  (c) 2-(((1S,4S)-5-(3-chloro-2-fluorobenzoyl)-2,5-diazabicyclo[2.2.1]hept-2-yl)methyl) -6-methyl-N-1H-pyrazol-3-ylpyrimidine-4-amine;
  (d) 2-(((1S,4S)-5-(3-chloro-2-fluorobenzoyl)-2,5-diazabicyclo[2.2.1]hept-2-yl)methyl)-N,N-dimethyl-6-(thiazol-2-ylamino)isonicotinamide; or
  (e) 6-(((1S,4S)-5-(2,3-dichlorobenzoyl)-2,5-diazabicyclo[2.2.1]hept-2-yl)methyl) -N-1H-pyrazol-3-ylpyrazin-2-amine, or a pharmaceutically acceptable salt or ester thereof; and paclitaxel or docetaxel, or a pharmaceutically acceptable salt or ester thereof, together with a pharmaceutically acceptable carrier or diluent.

Description of the process for preparation of compound of General Formula ($I_0$)

Among the compounds represented by the General Formula ($I_0$):

($I_0$)

(wherein $n_1$, $n_2$, R, $R_c$, $R_d$, $R_e$, $X_1$, $X_2$, $X_3$, $X_4$, $Y_1$, $Y_2$, $Y_3$ and W have the same meaning as defined in the above) according to the invention, the compound of Formula ($I_0$-1) in which $Y_1$ is CH:

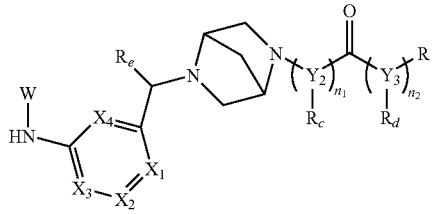

(wherein the symbols have the same meaning as the symbols for the above Formula ($I_0$)) can be prepared by, for example, the following method. Hereinafter, the term "symbols for the above Formula ($I_0$)" in the phrase "same meaning as the symbols for the above Formula ($I_0$)" means "the respective symbols as described for General Formula ($I_0$) initially described in the present specification."

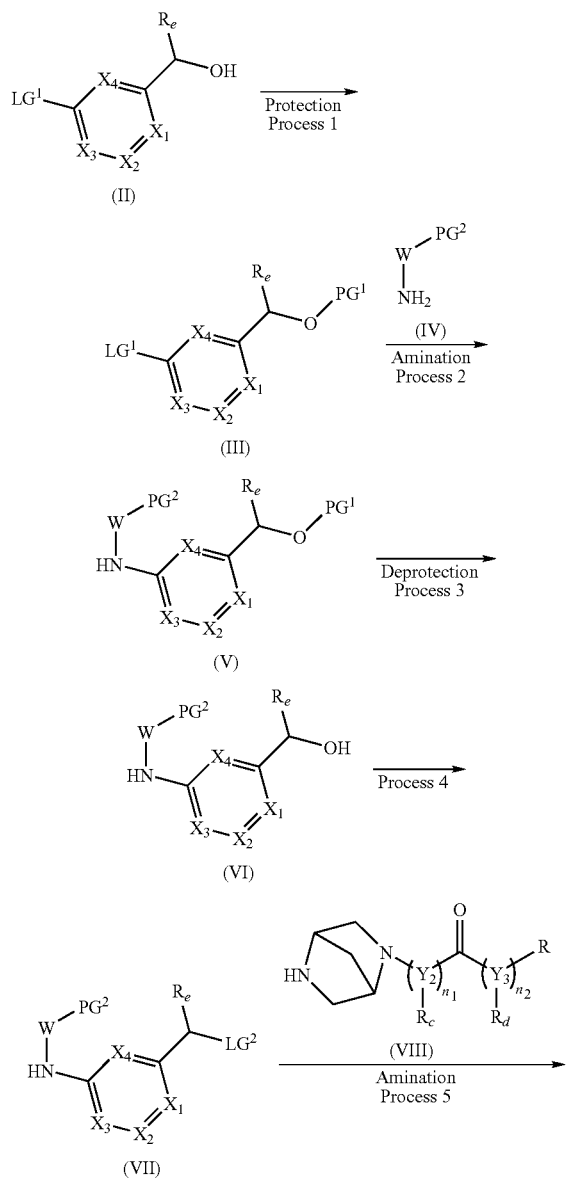

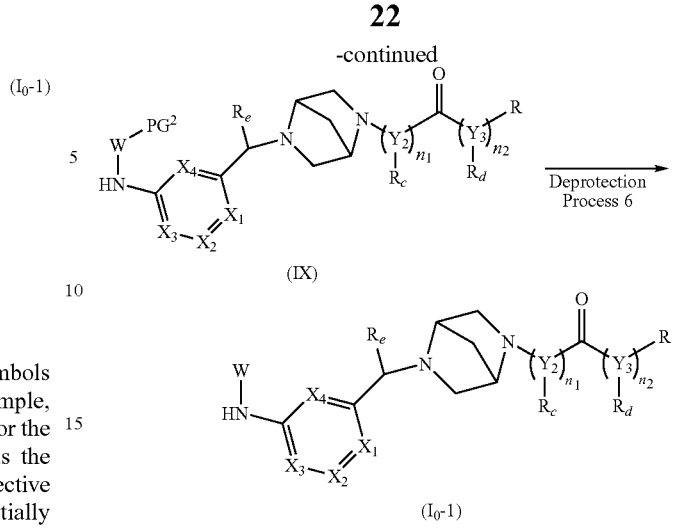

(Process 1) The present process is a method of introducing a protective group $PG^1$ such as a tert-butyldimethylsilyl group to Compound (II) (wherein $LG^1$ represents a leaving group such as halogen, and $X_1$, $X_2$, $X_3$, $X_4$ and $R_e$ have the same meaning as the symbols for the above Formula ($I_0$)), to produce Compound (III) (wherein $LG^1$ and $PG^1$ have the same meaning as defined above, and $X_1$, $X_2$, $X_3$, $X_4$ and $R_e$ have the same meaning as the symbols for the above Formula ($I_0$)).

The above-mentioned Compound (II) used in this process may be exemplified by (6-bromopyridin-2-yl)methanol, 1-(6-bromopyridin-2-yl)ethanol or (3-iodophenyl)methanol. The above-mentioned Compound (II) is commercially available or can be prepared by known methods.

As to the protective group $PG^1$, a method of protection may vary depending on the type of the protective group, but methods described in the literature [See T. W. Greene, *Protective Groups in Organic Synthesis*, John Wiley & Sons (1981)] or methods equivalent thereto can be utilized. For example, the Compound (II) can be synthesized by using tert-butyldimethylsilyl chloride in a solvent such as N,N-dimethylformamide in the presence of a base such as imidazole. When tert-butyldimethylsilyl chloride is used in a protection reaction, tert-butyldimethylsilyl chloride is used in an amount of from 1 to 10 mol, preferably from 1 to 3 mol, and the base is used in an amount of from 1 to 20 mol, preferably from 1 to 5 mol, relative to 1 mol of Compound (II). In this case, the reaction temperature may be appropriately selected by a person skilled in the art in accordance with the starting compound or reaction solvent used, but it is typically from 0° C. to the boiling point of the solvent. Also, the reaction is typically completed within 1 hour to 24 hours, but the reaction time can be appropriately extended or reduced.

Thus obtained Compound (III) is subjected to isolation and purification by known separation and purification means such as, for example, concentration, concentration under reduced pressure, crystallization, solvent extraction, reprecipitation or chromatography, or is subjected to the next process without isolation and purification.

(Process 2) The present process is a method of subjecting Compound (III) obtained by the above-described Process 1 (wherein $LG^1$ and $PG^1$ have the same meaning as defined above, and $X_1$, $X_2$, $X_3$, $X_4$ and $R_e$ have the same meaning as the symbols for the above Formula ($I_0$)) and Compound (IV) (wherein $PG^2$ may be absent, or if present, it is a protective group such as 4-methoxybenzyl, 2,4-dimethoxybenzyl, benzyl, methoxymethyl, (2-(trimethylsilyl)ethoxy)methyl or tert-butyl, preferably (2-(trimethylsilyl)ethoxy)methyl, methoxymethyl or tert-butyl, and W has the same meaning as the symbol for the above Formula ($I_0$)) to an amination reaction to produce Compound (V) (wherein $PG^1$ and $PG^2$ have the same meaning as defined above, and $X_1, X_2, X_3, X_4$ and $R_e$ have the same meaning as the symbols for the above Formula ($I_0$)).

The above-mentioned Compound (IV) used in this process may be exemplified by 2-aminothiazol-5-carbonitrile, 2-aminothiazole, 2-amino-5-methylthiazole, 5-amino-1,2,4-thiadiazole, 5-methyl-1-((2-(trimethylsilyl)ethoxy)methyl)-1H-pyrazol-3-amine, 1-((2-(trimethylsilyl)ethoxy)methyl)-1H-pyrazol-3-amine, or 1-tert-butyl-3-methyl-1H-pyrazol-5-amine. The Compound (IV) is commercially available or can be prepared by known methods (e.g., *Phosphorus, Sulfur and Silicon and the Related Elements*, Vol. 177, No. 1, pages 2651-2659 (2002), and *Journal of Chemical Research, Synopses*, Vol. 6, page 198 (1979)).

The amination reaction used in this process employs methods well known to those skilled in the art. In the amination reaction used in the process, specifically, for example, synthesis can be performed by reacting the above-mentioned Compound (III) and Compound (IV) in a solvent such as 1,4-dioxane, 1,2-dimethoxyethane, tetrahydrofuran, methylene chloride, chloroform or toluene, using a palladium catalyst such as trisdibenzylideneacetone dipalladium (0) or palladium acetate, a ligand such as 2,2'-bisdiphenylphosphino-1,1'-binaphthyl or 4,5-bis(diphenylphosphino)-9,9-dimethylxanthene, and a base such as cesium carbonate or sodium t-butoxide. In the reaction, with respect to 1 mol of compound (III), 0.5 to 3 mol, preferably 1 mol, of Compound (IV) is used; 0.001 to 1 mol, preferably 0.05 to 0.5 mol, of palladium catalyst is used; 0.002 to 2 mol, preferably 0.1 to 1.0 mol, of ligand is used; and 1 to 10 mol, preferably 1 to 3 mol, of base is used. The reaction temperature is appropriately selected by a person skilled in the art in accordance with the starting compound or reaction solvent used, but it is typically from 50° C. to the boiling point of the solvent used in the reaction. Also, the reaction is typically completed within 1 hour to 24 hours, but the reaction time can be appropriately extended or reduced. Thus obtained Compound (V) is subjected to isolation and purification by known separation and purification means such as, for example, concentration, concentration under reduced pressure, crystallization, solvent extraction, reprecipitation or chromatography, or subjected to the next process without isolation and purification.

(Process 3) The present process is a method of deprotecting Compound (V) obtained in the above-described Process 2 (wherein $PG^1$ and $PG^2$ have the same meaning as defined above, and $X_1, X_2, X_3, X_4, R_e$ and W have the same meaning as the symbols for the above Formula ($I_0$)) by removing protective group $PG^1$ to produce Compound (VI) (wherein $PG^2$ has the same meaning as defined above, and $X_1, X_2, X_3, X_4, R_e$ and W have the same meaning as the symbols for the above Formula ($I_0$)).

For removal of the protective group $PG^1$ used in this process, the method of removal may vary depending on the type of the protective group and stability of the compound, but methods described in the literature [See T. W. Greene, *Protective Groups in Organic Synthesis*, John Wiley & Sons (1981)] or methods equivalent thereto can be carried out. For example, Compound (V) in which $PG^1$ is tert-butyldimethylsilyl can be deprotected in a solvent such as tetrahydrofuran using tetrabutylammonium fluoride. When tetrabutylammonium fluoride is used in the deprotection reaction, tetrabutylammonium fluoride is used in an amount of from 1 to 10 mol, preferably from 1 to 3 mol, relative to 1 mol of Compound (V). The reaction temperature can be appropriately selected by a person having ordinary skill in the art in accordance with the starting compound or reaction solvent used, but it is typically from 0° C. to the boiling point of the solvent. Also, the reaction is typically completed within 1 hour to 24 hours, but the reaction time can be appropriately extended or reduced.

Thus obtained Compound (VI) is subjected to isolation and purification by known separation and purification means such as, for example, concentration, concentration under reduced pressure, crystallization, solvent extraction, reprecipitation or chromatography, or subjected to the next process without isolation and purification.

(Process 4) The present process is a method of converting a hydroxyl group of Compound (VI) obtained in the above-described Process 3 (wherein $PG^2$ has the same meaning as defined above, and $X_1, X_2, X_3, X_4, R_e$ and W have the same meaning as the symbols for the above Formula ($I_0$)) to a leaving group such as methylsulfonyloxy or chloro to produce Compound (VII) (wherein $LG^2$ represents a leaving group such as methylsulfonyloxy, or halogen atom, $PG^2$ has the same meaning as defined above, and $X_1, X_2, X_3, X_4, R_e$ and W have the same meaning as the symbols for the above Formula ($I_0$)).

The reaction used in this process employs methods well known to those skilled in the art. In the reaction used in this process, specifically, for example, Compound (VII) in which, $LG^2$ is methylsulfonyloxy can be obtained by reacting Compound (VI) with methanesulfonyl chloride in a solvent such as chloroform, methylene chloride, tetrahydrofuran, N,N-dimethylformamide, diethyl ether or ethyl acetate, in the presence of a base such as triethylamine or diisopropylethylamine. In this case, with respect to 1 mol of Compound (VI), methanesulfonyl chloride is used in an amount of from 1 to 10 mol, preferably from 1 to 3 mol; and the base is used in an amount of from 1 to 20 mol, preferably from 1 to 6 mol. The reaction temperature can be appropriately selected by a person having ordinary skill in the art in accordance with the starting compound or reaction solvent used, but it is typically from 0° C. to room temperature. Also, the reaction is typically completed within 10 minutes to 2 hours, but the reaction time can be appropriately extended or reduced.

Thus obtained Compound (VII) is subjected to isolation and purification by known separation and purification means such as, for example, concentration, concentration under reduced pressure, crystallization, solvent extraction, reprecipitation or chromatography, or subjected to the next process without isolation and purification.

(Process 5) The present process is a method of subjecting Compound (VII) obtained in the above-described Process 4 (wherein $LG^2$ and $PG^2$ have the same meaning as defined above, and $X_1, X_2, X_3, X_4, R_e$ and W have the same meaning as the symbols for the above Formula ($I_0$)) and Compound (VIII) (wherein $n_1, n_2, R, R_c, R_d, Y_2,$ and $Y_3$ have the same meaning as the symbols for the above Formula ($I_0$)) to an amination reaction to produce Compound (IX) (wherein $PG^2$ has the same meaning as defined above, and $X_1, X_2, X_3, X_4, R_e$ and W, and $n_1, n_2, R, R_c, R_d, Y_2,$ and $Y_3$ have the same meaning as the symbols for the above Formula ($I_0$)).

The aforementioned Compound (VIII) used in this process may be exemplified by 2-(3-chloro-2-fluorobenzoyl)-2,5-diazabicyclo[2.2.1]heptane, 2-(3-(trifluoromethyl)-2-fluorobenzoyl)-2,5-diazabicyclo[2.2.1]heptane, 2-(2,3-dichlorobenzoyl)-2,5-diazabicyclo[2.2.1]heptane. The synthesis of Compound (VIII) will be described later.

The amination reaction used in this process employs methods well known to those skilled in the art. In the amination reaction used in this process, specifically, for example, synthesis can be performed by reacting Compound (VII) and Compound (VIII) in a solvent such as tetrahydrofuran, dimethylsulfoxide, N,N-dimethylformamide, 1,4-dioxane, methylene chloride or chloroform, using a base such as sodium hydrogen carbonate, triethylamine, diisopropylethylamine or sodium hydroxide. In this case, with respect to 1 mol of Compound (VII), Compound (VIII) is used in an amount of from 1 to 10 mol, preferably from 1 to 3 mol; and the base is used in an amount of from 1 to 20 mol, preferably from 1 to 5 mol. The reaction temperature can be appropriately selected by a person having ordinary skill in the art in accordance with the starting compound or reaction solvent used, but it is typically from room temperature to the boiling point of the solvent. Also, the reaction is typically completed within 1 hour to 24 hours, but the reaction time can be appropriately extended or reduced.

Thus obtained Compound (IX) is subjected to isolation and purification by known separation and purification means such as, for example, concentration, concentration under reduced pressure, crystallization, solvent extraction, reprecipitation or chromatography, or subjected to the next process without isolation and purification.

In addition, if Compound (IX) does not necessitate deprotection, this Compound (IX) is used as the compound according to the invention without further performing the following Process 6.

(Process 6) The present process is a method of subjecting Compound (IX) obtained in the above-described Process 5 (wherein $PG^2$ has the same meaning as defined above, and $X_1$, $X_2$, $X_3$, $X_4$, $R_e$ and W, and $n_1$, $n_2$, R, $R_c$, $R_d$, $Y_2$, and $Y_3$ have the same meaning as the symbols for the above Formula $(I_0)$) to a deprotection reaction to produce Compound $(I_0\text{-}1)$ (wherein $X_1$, $X_2$, $X_3$, $X_4$, $R_e$ and W, and $n_1$, $n_2$, R, $R_c$, $R_d$, $Y_2$, and $Y_3$ have the same meaning as the symbols for the above Formula $(I_0)$).

For the deprotection reaction of $PG^2$, the method may vary depending on the type of the protective group or stability of the compound, but methods described in the literature [See T. W. Greene, Protective Groups in Organic Synthesis, John Wiley & Sons (1981)] or methods equivalent thereto can be carried out, for example, by solvolysis using acid.

For example, specifically, synthesis can be performed by subjecting Compound (IX) (wherein W is 1H-pyrazol-3-yl, $PG^2$ is (2-(trimethylsilyl)ethoxy)methyl or tert-butyl, the pyrazole of W is substituted with $PG^2$ at the 1-position or 2-position, and $X_1$, $X_2$, $X_3$, $X_4$, and $R_e$, and $n_1$, $n_2$, R, $R_c$, $R_d$, $Y_2$, and $Y_3$ have the same meaning as the symbols for the above Formula $(I_0)$) to deprotection reaction by solvolysis using a solvent mixture of trifluoroacetic acid and water or formic acid and water, to produce the corresponding Compound $(I_0\text{-}1)$ (wherein W has the same meaning as defined above, and $X_1$, $X_2$, $X_3$, $X_4$, and $R_e$, and $n_1$, $n_2$, R, $R_c$, $R_d$, $Y_2$, and $Y_3$ have the same meaning as the symbols for the above Formula $(I_0)$). In this case, the reaction temperature can be appropriately selected by a person having ordinary skill in the art in accordance with the starting compound or reaction solvent used, but it is typically from 0° C. to the boiling point of the solvent. Also, the reaction is typically completed within 1 hour to 24 hours, but the reaction time can be appropriately extended or reduced.

Thus obtained Compound $(I_0\text{-}1)$ is subjected to isolation and purification by known separation and purification means such as, for example, concentration, concentration under reduced pressure, crystallization, solvent extraction, reprecipitation or chromatography, or subjected to the next process without isolation and purification.

Among the Compounds (VIII) (wherein $n_1$, $n_2$, R, $R_c$, $R_d$, $Y_2$, and $Y_3$ have the same meaning as the symbols for the above Formula $(I_0)$) according to the invention, Compound (VIII-1) (wherein $n_1$ is 0, and $n_2$, R, $R_d$ and $Y_3$ have the same meaning as the symbols for the above Formula $(I_0)$) can be prepared, for example, by the following method.

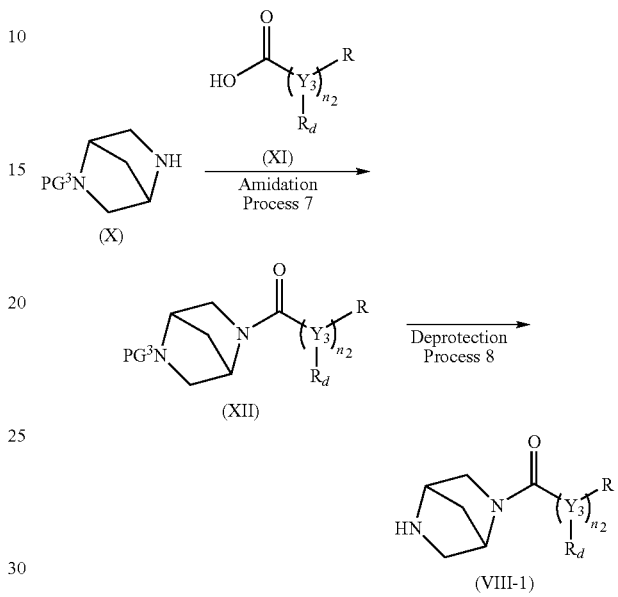

(Process 7) The present process is a method of subjecting Compound (X) (wherein $PG^3$ is a protective group such as tert-butyloxycarbonyl) and Compound (XI) (wherein $n_2$, R, $R_d$ and $Y_3$ have the same meaning as the symbols for the above Formula $(I_0)$) to an amidation reaction to produce Compound (XII) (wherein $PG^3$ has the same meaning as defined above, and $n_2$, R, $R_d$ and $Y_3$ have the same meaning as the symbols for the above Formula $(I_0)$).

The aforementioned Compound (X) used in this process may be exemplified by tert-butyl-2,5-diazabicyclo[2.2.1]heptane-2-carboxylic acid ester, benzyl-2,5-diazabicyclo[2.2.1]heptane-2-carboxylic acid ester or 2-(trifluoromethylacetyl)-2,5-diazabicyclo[2.2.1]heptane. This Compound (X) is commercially available or can be prepared by known methods (e.g., Synthesis, Vol. 10, pages 920-930 (1990)).

The aforementioned Compound (XI) used in this process may be exemplified by 2,3-dichlorobenzoic acid, 3-chloro-2-fluorobenzoic acid, 3-(trifluoromethyl)-2-fluorobenzoic acid, etc. This Compound (XI) is commercially available or can be produced by known methods.

The amidation reaction used in this process can be carried out by using a carboxylic acid represented by the above-described Compound (XI) or its reactive derivatives and the above-described Compound (X). Examples of the "reactive derivatives" of Compound (XI) may include mixed acid anhydrides, active esters and active amides, and these can be obtained according to the method described in, for example, WO 98/05641. Specifically, for example, synthesis can be performed by condensing the above Compound (X) and Compound (XI) in a solvent such as tetrahydrofuran, dimethylsulfoxide, N,N-dimethylformamide, 1,4-dioxane, methylene chloride or chloroform, using a condensing agent such as 1-(3-dimethylaminopropyl)-3-ethylcarbodiimide, and 1-hydroxybenzotriazole. In this case, with respect to 1 mol of Compound (X), Compound (XI) is used in an amount of from 1 to 3 mol, preferably 1 mol, and the condensing agent is used in an amount from 1 to 10 mol, preferably from 1 to 3 mol. The reaction temperature is appropriately selected by a person skilled in the art in accordance with the starting compound or reaction solvent used, but it is typically from room temperature to the boiling point of the solvent used in the reaction. Also, the reaction is typically completed within 1 hour to 24 hours, but the reaction time can be appropriately extended or reduced.

Thus obtained Compound (XII) is subjected to isolation and purification by known separation and purification means such as, for example, concentration, concentration under reduced pressure, crystallization, solvent extraction, reprecipitation or chromatography, or subjected to the next process without isolation and purification.

(Process 8) The present process is a method of deprotecting Compound (XII) obtained in the above-described Process 7 (wherein $PG^3$ has the same meaning as defined above, and $n_2$, R, $R_d$ and $Y_3$ have the same meaning as the symbols for the above Formula ($I_0$)) by removing protective group $PG^3$ to produce a compound represented by Formula (VIII-1) (wherein $n_2$, R, $R_d$ and $Y_3$ have the same meaning as the symbols for the above Formula ($I_0$)).

The deprotection reaction used in this process employs methods well known to those skilled in the art. For removal of the protective group of the above-mentioned Compound (XII) in this process, the method of removal may vary depending on the type of the protective group and stability of the compound, but methods described in the literature [See T. W. Greene, *Protective Groups in Organic Synthesis*, John Wiley & Sons (1981)] or methods equivalent thereto can be carried out. For example, the deprotection reaction for the compound represented by Formula (XII) (wherein $PG^3$ is tert-butyloxycarbonyl) can be carried out by solvolysis using acid.

Thus obtained Compound (VIII-1) is subjected to isolation and purification by known separation and purification means such as, for example, concentration, concentration under reduced pressure, crystallization, solvent extraction, reprecipitation or chromatography, or subjected to the next process without isolation and purification.

Among the Compounds (VI) (wherein $PG^2$ has the same meaning as defined above, and $R_e$, $X_1$, $X_2$, $X_3$, $X_4$ and W have the same meaning as the symbols for the above Formula ($I_0$)) according to the invention, Compound (VI-1) (wherein $R_e$ is hydrogen atom, $PG^2$ has the same meaning as defined above, and $X_1$, $X_2$, $X_3$, $X_4$ and W have the same meaning as the symbols for the above Formula ($I_0$)) can be also prepared, for example, by the following method.

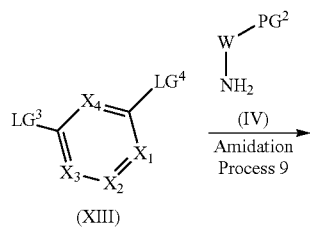

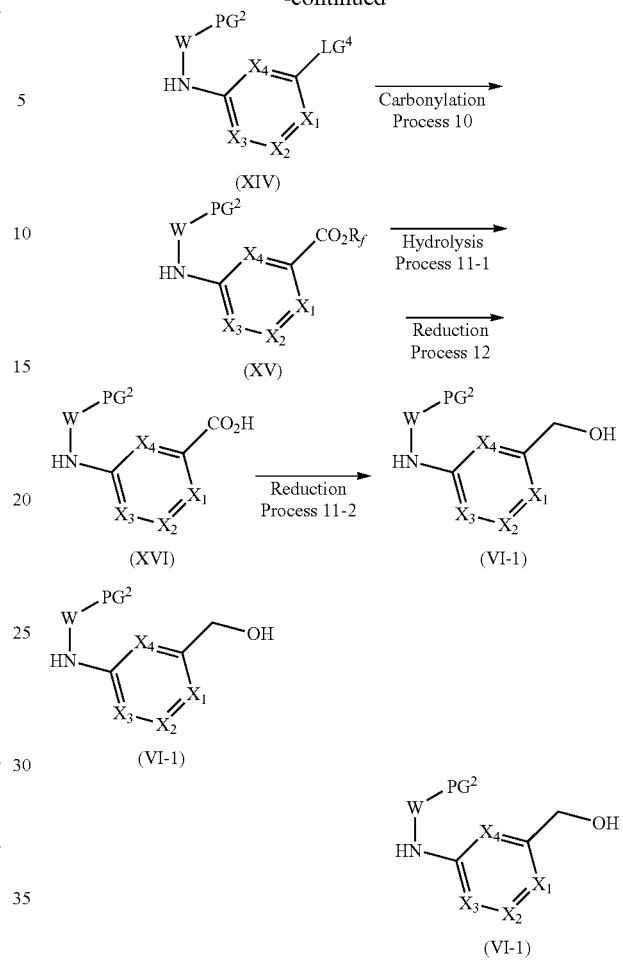

(Process 9) The present process is a method of subjecting Compound (XIII) (wherein $LG^3$ and $LG^4$ each represent a leaving group such as halogen atom, and $X_1$, $X_2$, $X_3$ and $X_4$ have the same meaning as the symbols for the above Formula ($I_0$)) and Compound (IV) (wherein $PG^2$ have the same meaning as defined above, and W has the same meaning as the symbol for the above Formula ($I_0$)) to an amination reaction to produce Compound (XIV) (wherein $PG^2$ and $LG^4$ have the same meaning as defined above, and $X_1$, $X_2$, $X_3$, $X_4$ and W have the same meaning as the symbols for the above Formula ($I_0$)).

The above-described Compound (IV) used in this process may be exemplified by 2-aminothiazole, 5-amino-1,2,4-thiadiazole, 5-methyl-1-((2-(trimethylsilyl)ethoxy)methyl)-1H-pyrazol-3-amine, 1-((2-(trimethylsilyl)ethoxy)methyl)-1H-pyrazol-3-amine, or 1-tert-butyl-3-methyl-1H-pyrazol-5-amine. The Compound (IV) is commercially available or can be prepared by known methods (e.g., *Phosphorus, Sulfur and Silicon and the Related Elements*, Vol. 177, No. 11, pages 2651-2659 (2002), and *Journal of Chemical Research, Synopses*, Vol. 6, page 198 (1979)).

The above-described Compound (XIII) used in this process may be exemplified by 2,6-dichloropyridine, 2,4-dichloropyrimidine or 2,6-dichloropyrazine. Compound (XIII) is commercially available or can be prepared by known methods.

This process can be carried out according to a method similar to the aforementioned Process 2, a method equivalent to that, or a combination of these methods with conventional methods.

Thus obtained Compound (XIV) (wherein $PG^2$ and $LG^4$ have the same meaning as defined above, and $X_1, X_2, X_3, X_4$ and W have the same meaning as the symbols for the above Formula $(I_0)$) is subjected to isolation and purification by known separation and purification means such as, for example, concentration, concentration under reduced pressure, crystallization, solvent extraction, reprecipitation or chromatography, or subjected to the next process without isolation and purification.

(Process 10) The present process is a method of subjecting Compound (XIV) obtained in the above-described Process 9 (wherein $PG^2$ and $LG^4$ have the same meaning as defined above, and $X_1, X_2, X_3, X_4$ and W have the same meaning as the symbols for the above Formula $(I_0)$) to a carbonylation reaction to produce Compound (XV) (wherein $R_f$ is lower alkyl, $PG^2$ has the same meaning as defined above, and $X_1, X_2, X_3, X_4$ and W have the same meaning as the symbols for the above Formula $(I_0)$).

The carbonylation reaction used in this process employs methods well known to those skilled in the art. In the carbonylation reaction used in this process, specifically, for example, Compound (XV) can be synthesized by reacting Compound (XIV) with carbon monoxide in a solvent mixture in which alcohol such as methanol or ethanol is added to a solvent such as N,N-dimethylacetamide, N-methylpyrrolidone or N,N-dimethylformamide, in the presence of a ligand such as 1,1'-bis(diphenylphosphino)ferrocene, a palladium catalyst such as palladium (II) acetate, and a base such as sodium hydrogen carbonate or triethylamine. In this case, with respect to 1 mol of Compound (XIV), the palladium catalyst is used in an amount of from 0.01 to 1 mol, preferably from 0.05 to 0.5 mol; the ligand is used in an amount of from 0.02 to 1 mol, preferably from 0.1 to 1 mol; and the base is used in an amount of from 1 to 10 mol, preferably from 1 to 3 mol. The reaction temperature can be appropriately selected by a person skilled in the art in accordance with the starting compound and reaction solvent used, but it is typically from 50° C. to the boiling point of the solvent used in the reaction. Also, the reaction is typically completed within 1 hour to 24 hours, but the reaction time can be appropriately extended or reduced.

Thus obtained Compound (XV) is subjected to isolation and purification by known separation and purification means such as, for example, concentration, concentration under reduced pressure, crystallization, solvent extraction, reprecipitation or chromatography, or subjected to the next process without isolation and purification.

(Process 11-1) The present process is a method of subjecting Compound (XV) obtained in the above-described Process 10 (wherein $R_f$ and $PG^2$ have the same meaning as defined above, and $X_1, X_2, X_3, X_4$ and W have the same meaning as the symbols for the above Formula $(I_0)$) to a hydrolysis reaction to produce Compound (XVI) (wherein $PG^2$ has the same meaning as defined above and $X_1, X_2, X_3, X_4$ and W have the same meaning as the symbols for the above Formula $(I_0)$).

The hydrolysis reaction used in this process employs methods well known to those skilled in the art. In the hydrolysis reaction used in this process, specifically, for example, Compound (XVI) can be synthesized by hydrolyzing Compound (XV) in a solvent such as methanol, ethanol or tetrahydrofuran, using an aqueous solution of sodium hydroxide as the base. In this case, with respect to 1 mol of Compound (XV), the base is used in an amount of from 1 to 1000 mol, preferably from 1 to 100 mol. The reaction temperature can be appropriately selected by a person skilled in the art in accordance with the starting compound and reaction solvent used, but it is typically from room temperature to the boiling point of the solvent. Also, the reaction is typically completed within 1 hour to 24 hours, but the reaction time can be appropriately extended or reduced.

Thus obtained Compound (XVI) is subjected to isolation and purification by known separation and purification means such as, for example, concentration, concentration under reduced pressure, crystallization, solvent extraction, reprecipitation or chromatography, or subjected to the next process without isolation and purification.

(Process 11-2) The present process is a method of subjecting Compound (XVI) obtained in the above-described Process 11-1 (wherein $PG^2$ has the same meaning as defined above, and $X_1, X_2, X_3, X_4$ and W have the same meaning as the symbols for the above Formula $(I_0)$) to a reduction reaction to produce Compound (VI-1) (wherein $PG^2$ has the same meaning as defined above, and $X_1, X_2, X_3, X_4$ and W have the same meaning as the symbols for the above Formula $(I_0)$).

The reduction reaction used in this process employs methods well known to those skilled in the art. In the reduction reaction used in this process, specifically, for example, Compound (VI-1) can be synthesized by reacting Compound (XVI) with N,N'-carbonyldiimidazole in a solvent such as N,N-dimethylformamide or tetrahydrofuran at room temperature for 12 to 24 hours, and then reacting again with a reducing agent such as sodium borohydride. In this case, with respect to 1 mol of Compound (XVI), N,N'-carbonyldiimidazole is used in an amount of from 1 to 10 mol, preferably from 1 to 3 mol; and the reducing agent is used in an amount of from 1 to 20 mol, preferably from 1 to 5 mol. The reaction temperature can be appropriately selected by a person skilled in the art in accordance with the starting compound and reaction solvent used, but it is typically from 0° C. to room temperature. Also, the reaction is typically completed within 10 minutes to 24 hours, but the reaction time can be appropriately extended or reduced.

Thus obtained Compound (VI-1) is subjected to isolation and purification by known separation and purification means such as, for example, concentration, concentration under reduced pressure, crystallization, solvent extraction, reprecipitation or chromatography, or subjected to the next process without isolation and purification.

(Process 12) The present process is a method of subjecting Compound (XV) obtained in the above-described Process 10 (wherein $R_f$ and $PG^2$ have the same meaning as defined above, and $X_1, X_2, X_3, X_4$ and W have the same meaning as the symbols for the above, Formula $(I_0)$) to a reduction reaction to produce Compound (VI-1) (wherein $PG^2$ has the same meaning as defined above, and $X_1, X_2, X_3, X_4$ and W have the same meaning as the symbols for the above Formula $(I_0)$).

The reduction reaction used in this process employs methods well known to those skilled in the art. In the reduction reaction used in this process, specifically, for example, Compound (VI-1) can be synthesized by reacting Compound (XV) with a reducing agent such as lithium borohydride or lithium aluminum hydride in a solvent such as tetrahydrofuran or 1,4-dioxane. In this case, with respect to 1 mol of Compound (XV), the reducing agent is used in an amount of from 1 to 20 mol, preferably from 1 to 5 mol. The reaction temperature can be appropriately selected by a person skilled in the art in accordance with the starting compound and reaction solvent used, but it is typically from 0° C. to the boiling point of the solvent used in the reaction. Also, the reaction is typically completed within 10 minutes to 24 hours, but the reaction time can be appropriately extended or reduced.

Thus obtained Compound (VI-1) is subjected to isolation and purification by known separation and purification means such as, for example, concentration, concentration under reduced pressure, crystallization, solvent extraction, reprecipitation or chromatography, or subjected to the next process without isolation and purification.

Compound (XV) (wherein $R_f$ is a lower alkyl group, $PG^2$ has the same meaning as defined above, and $X_1$, $X_2$, $X_3$, $X_4$ and W have the same meanings as the symbols for the above Formula ($I_0$)) according to the invention can be also prepared by, for example, the following method.

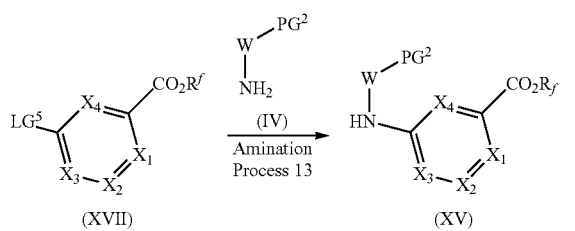

(Process 13) The present process is a method of subjecting Compound (XVII) (wherein $R_f$ is a lower alkyl group, $LG^5$ is a leaving group such as halogen atom, and $X_1$, $X_2$, $X_3$ and $X_4$ have the same meanings as the symbols for the above Formula ($I_0$)) and Compound (IV) (wherein $PG^2$ has the same meaning as defined above, and W has the same meaning as the symbol for the above Formula ($I_0$)) to an amination reaction to produce Compound (XV) (wherein $R_f$ is a lower alkyl group, $PG^2$ has the same meaning as defined above, and $X_1$, $X_2$, $X_3$, $X_4$ and W have the same meanings as the symbols for the above Formula ($I_0$)).

The above-described Compound (IV) that is used in this process may be exemplified by 2-aminothiazole, 5-amino-1,2,4-thiadiazole, 5-methyl-1-((2-(trimethylsilyl)ethoxy)methyl)-1H-pyrazol-3-amine, 1-((2-(trimethylsilyl)ethoxy)methyl)-1H-pyrazol-3-amine, 1-tert-butyl-3-methyl-1H-pyrazol-5-amine and the like. The above-described Compound (IV) is commercially available or can be produced by known methods (for example, Phosphorus, Sulfur and Silicon and the Related Elements, Vol. 177 (11) pp. 2651-2659 (2002); and Journal of Chemical Research, Synopses, Vol. 6, p. 198 (1979)).

The above-mentioned Compound (XVII) that is used in the present process may be exemplified by 6-chloro-2-pyridinecarboxylic acid methyl ester, 6-chloro-4-methoxy-2-pyridinecarboxylic acid methyl ester or the like. Compound (XVII) is commercially available or can be produced by known methods.

This process can be carried out by a method similar to the above-described Process 2, a method equivalent to this, or a combination of these methods and conventional methods.

Thus obtained, aforementioned Compound (XV) (wherein $R_f$ is a lower alkyl group, $PG^2$ has the same meaning as defined above, and $X_1$, $X_2$, $X_3$, $X_4$ and W have the same meanings as the symbols for the above Formula ($I_0$)) can be either subjected to isolation and purification by known separation and purification means such as, for example, concentration, concentration under reduced pressure, crystallization, solvent extraction, reprecipitation or chromatography, or subjected to the next process without isolation and purification.

The aforementioned introduction of a protective group into a compound can be carried out in any one of the stages for producing the above-described synthetic intermediates as needed. In obtaining the protection product, reaction can be carried out in a manner similar to the corresponding process as described above. Further, such compound can be deprotected by removing the introduced protective group according to a method similar to the aforementioned Process 6, a method equivalent to that, or a combination of these methods and conventional methods.

Hereinunder, examples of introducing protective groups to Compound (IV) and to Compound (XV) will be illustrated. In addition, a person having ordinary skill in the art can perform introduction of protective groups into the above-mentioned synthetic intermediates by using commercially available, known compounds and using any appropriate, known method, and/or the below-described methods or methods equivalent to these.

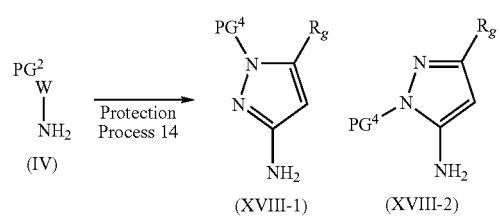

(Process 14) The present process is a method of producing Compound (XVIII-1) or Compound (XVIII-2) (wherein $PG^4$ is a protective group such as methoxymethyl or (2-(trimethylsilyl)ethoxy)methyl, and $R_9$ is a substituent such as hydrogen atom, methyl or cyclopropyl) by introducing a protective group into Compound (IV) (wherein $-W-PG^2$ is 5-methyl-1H-pyrazol-3-yl, 5-cyclopropyl-1H-pyrazol-3-yl or 1H-pyrazol-3-yl).

In the protection reaction used in this process, for example, Compound (IV) is protected in a solvent such as tetrahydrofuran, N,N-dimethylformamide, 1,4-dioxane, toluene, dichloromethane or chloroform, using a base such as sodium hydride together with chloromethyl methyl ether, chloromethyl 2-(trimethylsilyl)ethyl ether or the like, to synthesize the corresponding Compound (XVIII-1) or Compound (XVIII-2). In this case, with respect to 1 mol of Compound (IV), the base is used in an amount of from 1 to 20 mol, preferably from 1 to 5 mol; and the protective reagent is used in an amount of from 1 to 10 mol, preferably from 1 to 3 mol. The reaction temperature can be appropriately selected by a person skilled in the art in accordance with the starting compound or reaction solvent used, but it is typically from 0° C. to room temperature. Also, the reaction is typically completed within 10 minutes to 24 hours, but the reaction time can be appropriately extended or reduced.

Thus obtained Compound (XVIII-1) or Compound (XVIII-2) is subjected to isolation and purification by known separation and purification means such as, for example, concentration, concentration under reduced pressure, crystallization, solvent extraction, reprecipitation or chromatography, or subjected to the next process without isolation and purification.

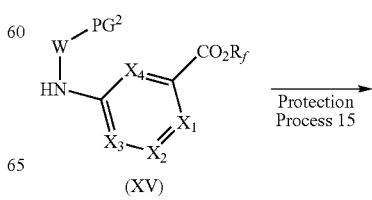

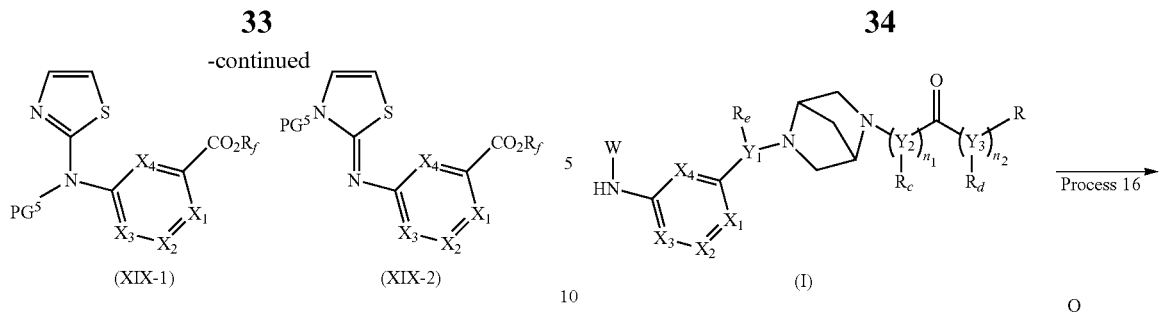

(XIX-1)　　　(XIX-2)　　　(I)

(Process 15) The present process is a method of producing Compound (XIX-1) or Compound (XIX-2) (wherein $R_f$ and $PG^5$ have the same meaning as defined above, and $X_1, X_2, X_3, X_4$ and W have the same meaning as the symbols for the above Formula ($I_0$)) by introducing a protective group $PG^5$ such as methoxymethyl or (2-(trimethylsilyl)ethoxy)methyl into Compound (XV) (wherein $R_f$ and $PG^2$ have the same meaning as defined above, and $X_1, X_2, X_3, X_4$ and W have the same meaning as the symbols for the above Formula ($I_0$)).

The protection reaction used in this process can be carried out, for example, by protecting Compound (XV) in a solvent such as tetrahydrofuran, N,N-dimethylformamide, 1,4-dioxane, toluene, dichloromethane or chloroform, using a base such as sodium hydride or diisopropylethylamine together with chloromethyl methyl ether, chloromethyl 2-(trimethylsilyl)ethyl ether or the like. In this case, with respect to 1 mol of Compound (XV), the base is used in an amount of from 1 to 20 mol, preferably from 1 to 5 mol, and the protective reagent is used in an amount of from 1 to 10 mol, preferably from 1 to 3 mol. The reaction temperature can be appropriately selected by a person skilled in the art in accordance with the starting compound or reaction solvent used, but it is typically from 0° C. to room temperature. Also, the reaction is typically completed within 10 minutes to 24 hours, but the reaction time can be appropriately extended or reduced.

Thus obtained Compound (XIX-1) or Compound (XIX-2) is subjected to isolation and purification by known separation and purification means such as, for example, concentration, concentration under reduced pressure, crystallization, solvent extraction, reprecipitation or chromatography, or subjected to the next process without isolation and purification.

Furthermore, introduction or conversion Of $X_{1a}$, $X_{2a}$ or $X_{3a}$ can be carried out at any step for producing the above-mentioned synthetic intermediates which may have appropriate protective groups. Hereinafter, examples of introduction or conversion of a substituent for $X_{2a}$ in the compound represented by Formula ($I_0$) (wherein $X_1$ is CH, $X_2$ is $CX_{2a}$, $X_3$ is CH, $X_4$ is N, and $n_1$, $n_2$, R, $R_c$, $R_d$, $R_e$, $Y_1$, $Y_2$, $Y_3$, and W have the same meanings as the symbols for the above Formula ($I_0$)), the above-mentioned Compound (XV) (wherein $R_f$, $PG^2$, $X_1$, $X_2$, $X_3$, $X_4$ and W have the same meanings as defined above) and the above-mentioned Compound (V) (wherein $PG^1$, $PG^2$, $X_1$, $X_2$, $X_3$, $X_4$, $R_e$ and W have the same meanings as defined above) will be illustrated. Here, the compound of Formula ($I_0$) mentioned in the description of the following Processes (16-1) to (16-3), the compound of Formula (XV) mentioned in the description of Process (17), and the compound of Formula (V) mentioned in the description of Processes (18-1) and (18-2) may have an appropriate protective group at a substitutable position to which a protective group can be introduced. Further, a person skilled in the art can perform introduction or conversion of a substituent for $X_{1a}$, $X_{2a}$ or $X_{3a}$ by using commercially available, known compounds and using any appropriate, known method, and/or the below-described methods or methods equivalent to these.

(XX)

Process 16 relates to a method of synthesizing Compound (XX) from Compound ($I_0$). Hereafter, it is exemplified in Processes 16-1 to 16-3.

(Process 16-1) The present process is a method of subjecting Compound ($I_0$) (wherein $X_1$ is CH, $X_2$ is $CX_{2a}$, $X_{2a}$ is bromine atom, $X_3$ is CH, $X_4$ is N and $n_1$, $n_2$, R, $R_c$, $R_d$, $R_e$, $Y_1$, $Y_2$, $Y_3$, and W have the same meaning as the symbols for the above Formula ($I_0$)) to a carbonylation reaction to produce Compound (XX) (wherein $X_1$ is CH, $X_2$ is $CX_{2a}$, $X_{2a}$ is alkoxycarbonyl, $X_3$ is CH, $X_4$ is N, and $n_1$, $n_2$, R, $R_c$, $R_d$, $R_e$, $Y_1$, $Y_2$, $Y_3$, and W have the same meaning as the symbols for the above Formula ($I_0$)).

This process can be carried out by a method similar to the above-described Process 10, a method equivalent to this, or a combination of these methods and conventional methods.

Thus obtained Compound (XX) according to the invention can be subjected to isolation and purification by known separation and purification means such as, for example, concentration, concentration under reduced pressure, crystallization, solvent extraction, reprecipitation or chromatography.

(Process 16-2) The present process is a method of subjecting Compound ($I_0$) (wherein $X_1$ is CH, $X_2$ is $CX_{2a}$, $X_{2a}$ is alkoxycarbonyl, $X_3$ is CH, $X_4$ is N, and $n_1$, $n_2$, R, $R_c$, $R_d$, $R_e$, $Y_1$, $Y_2$, $Y_3$, and W have the same meaning as the symbols for the above Formula ($I_0$)) to a hydrolysis reaction to produce Compound (XX) (wherein $X_1$ is CH, $X_2$ is $CX_{2a}$, $X_{2a}$ is carboxy, $X_3$ is CH, $X_4$ is N, and $n_1$, $n_2$, R, $R_c$, $R_d$, $R_e$, $Y_1$, $Y_2$, $Y_3$, and W have the same meaning as the symbols for the above Formula ($I_0$)).

This process can be carried out by a method similar to the above-described Process 11, a method equivalent to this, or a combination of these methods and conventional methods.

Thus obtained Compound (XX) according to the invention can be subjected to isolation and purification by known separation and purification means such as, for example, concentration, concentration under reduced pressure, crystallization, solvent extraction, reprecipitation or chromatography.

(Process 16-3) The present process is a method of subjecting Compound ($I_0$) (wherein $X_1$ is CH, $X_2$ is $CX_{2a}$, $X_{2a}$ is carboxyl, $X_3$ is CH, $X_4$ is N, and $n_1$, $n_2$, R, $R_c$, $R_d$, $R_e$, $Y_1$, $Y_2$, $Y_3$, and W have the same meaning as the symbols for the above Formula ($I_0$)) to an amidation reaction to produce Compound (XX) (wherein $X_{2a}$ is carbamoyl, and $n_1$, $n_2$, R, $R_c$, $R_d$, $R_e$, $Y_1$, $Y_2$, $Y_3$, and W have the same meaning as the symbols for the above Formula ($I_0$)).

This process can be carried out by a method similar to the above-described Process 7, a method equivalent to this, or a combination of these methods and conventional methods. The amine used in this process may be exemplified by dimethylamine, methylamine, pyrrolidine and 2-hydroxyethylamine.

Thus obtained Compound (XX) according to the invention can be subjected to isolation and purification by known separation and purification means such as, for example, concentration, concentration under reduced pressure, crystallization, solvent extraction, reprecipitation or chromatography.

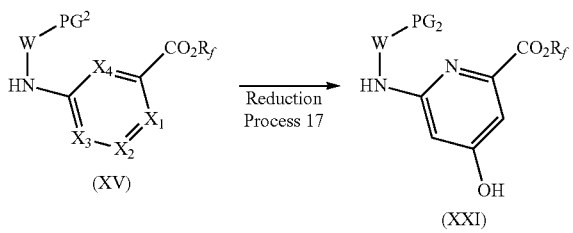

(Process 17) The present process is a method of removing a benzyl group that is a protective group of the hydroxyl group of Compound (XV) (wherein $R_f$ is a lower alkyl group, $PG^2$ has the same meaning as defined above, $X_1$ is CH, $X_2$ is $CX_{2a}$, $X_{2a}$ is a benzyloxy group, $X_3$ is CH, $X_4$ is N, and W has the same meaning as the symbol for the above Formula $(I_0)$) to produce Compound (XXI) (wherein $R_f$, $PG^2$ and W have the same meanings as defined above).

Removal of a protective group in this process can be carried out by methods described in the literature (for example, T. W. Green, Protective Groups in Organic Synthesis, $2^{nd}$ Ed., John Wiley & Sons (1991), etc.), methods equivalent to these or combinations of these methods and conventional methods, for example, by catalytic hydrogenation using a palladium hydroxide-carbon catalyst, or the like.

In the case of using a palladium hydroxide-carbon catalyst in removal of the benzyl group, the amount of the catalyst is usually 0.01 to 1000 equivalents, and preferably 0.1 to 10 equivalents.

The reaction solvent used in the present process is not particularly limited as long as it does not affect the reaction, and may be exemplified by methanol, ethanol or the like.

Thus obtained, above-described Compound (XXI) according to the invention can be subjected to isolation and purification by known separation and purification means such as, for example, concentration, concentration under reduced pressure, crystallization, solvent extraction, reprecipitation or chromatography.

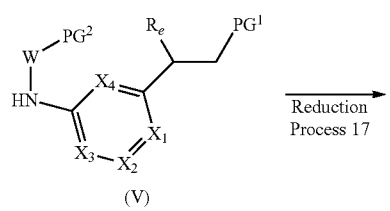

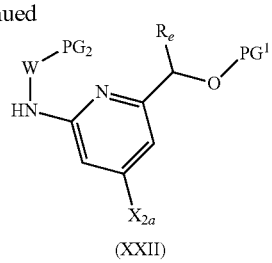

Process 18 relates to a method of synthesizing Compound (XXII) from Compound (V). Hereafter, it is exemplified in Processes 18-1 and 18-2.

(Process 18-1) The present process is a method of producing Compound (XXII) (wherein $R_e$, W, $PG^1$ and $PG^2$ have the same meanings as defined above, and $X_{2a}$ is a trifluoromethylsulfonyloxy group) from Compound (V) (wherein $R_e$, W, $PG^1$ and $PG^2$ have the same meanings as defined above, $X_1$ is CH, $X_2$ is $CX_{2a}$, $X_{2a}$ is a hydroxyl group, $X_3$ is CH, and $X_4$ is N).

The reaction used in this process employs a method well-known to a person skilled in the art. In the reaction used in this process, specifically, for example, the above-described Compound (V) can be reacted with anhydrous trifluoromethanesulfonic acid in a solvent such as chloroform, methylene chloride, tetrahydrofuran, N,N-dimethylformamide, diethyl ether and ethyl acetate, in the presence of a base such as 4-dimethylaminopyridine, triethylamine and diisopropylethylamine, to obtain Compound (XXII) (wherein $R_e$, W, $PG^1$ and $PG^2$ have the same meanings as defined above, and $X_{2a}$ is a trifluoromethylsulfonyloxy group). In this case, with respect to 1 mole of Compound (V), anhydrous trifluoromethanesulfonic acid is used in an amount of 1 to 10 moles, and preferably 1 to 3 moles, and the base is used in an amount of 1 to 20 moles, and preferably 1 to 6 moles. The reaction temperature can be appropriately selected by a person skilled in the art in accordance with the starting compound used, and it is usually 0° C. to room temperature. Also, the reaction is typically completed in 10 minutes to 2 hours, but the reaction time can be appropriately extended or reduced.

Thus obtained, above-mentioned Compound (XXII) can be either subjected to isolation and purification by known separation and purification means such as, for example, concentration, concentration under reduced pressure, crystallization, solvent extraction, reprecipitation and chromatography, or subjected to the next process without isolation and purification.

(Process 18-2) The present process is a method of subjecting Compound (V) (wherein $R_e$, W, $PG^1$ and $PG^2$ have the same meanings as defined above, $X_1$ is CH, $X_2$ is $CX_{2a}$, $X_{2a}$ is a trifluoromethylsulfonyloxy group, $X_3$ is CH, and $X_4$ is N) to a carbonylation reaction to produce Compound (XXII) (wherein $R_e$, W, $PG^1$ and $PG^2$ have the same meanings as defined above, and $X_{2a}$ is an alkoxycarbonyl group).

The present process can be carried out by a method similar to the above-described Process 10, a method equivalent to this, or a combination of these methods and conventional methods.

Thus obtained, above-described Compound (XXII) according to the invention can be subjected to isolation and purification by known separation and purification means such as, for example, concentration, concentration under reduced pressure, crystallization, solvent extraction, reprecipitation and chromatography.

Descriptions of Manufacturing Methods of a Compound of Formula (I)

A compound of General Formula (I) can be synthesized using tert-butyl 3,6-diazabicyclo[3.1.1]heptane-6-carboxylate, 3-benzyl-3,6-diazabicyclo[3.1.1]heptane, tert-butyl 3,8-diazabicyclo[3.2.1]octane-8-carboxylate, tert-butyl 3,8-diazabicyclo[3.2.1]octane-3-carboxylate, 3-benzyl-3,9-diazabicyclo[3.3.1]nonane as Compound (X) used in Process 7 in accordance with a manufacturing method for a compound of Formula ($I_0$). The Compound (X) is commercially available or can be prepared by a known method (for example, Bioorgainic & Medicinal Chemistry, 2006, Vol. 14 (3), Pages 676-691, WO2005/108402, Journal of Medicinal Chemistry 1998, Vol. 41 (5), Pages 674-681, Farmaco 2000, Vol. 55 (8), Pages 553-562, etc.

Next, the Aurora A and Aurora B inhibitory actions of the compound of General Formula (I) according to the invention will be explained below.

Aurora A Inhibitory Action (1) Purification of Aurora A cDNA of Aurora A having histidine tag fused at the amino terminal was integrated into an expression vector, which was then highly expressed in *Escherichia coli* BL21-CodonPlus (DE3)-RIL cells. The *Escherichia coli* cells were recovered and solubilized, and then the histidine-tagged Aurora A protein was adsorbed onto a nickel chelate column and eluted from the column with imidazole. The active fraction was desalted with a desalting column to give a pure enzyme.

(2) Measurement of Activity of Aurora A

For measurement of the activity of Aurora A, the substrate used was Kemptide (Leu-Arg-Arg-Ala-Ser-Leu-Gly) (SEQ.ID.NO.: 1), a synthetic peptide purchased from Sigma-Aldrich, Inc. [Certificate of analysis (Upstate, Inc.)].

Reaction was conducted by a partial modification of a method by Upstate, Inc. [Kinase Profiler™ Assay Protocols]. The amount of the reaction liquid was 21.1 µL, and the composition of the reaction buffer (R2 buffer) was 50 mM Tris-hydrochloride buffer (pH 7.4)/15 mM magnesium acetate/0.2 mM ethylenediamine-N,N,N',N'-tetraacetate (EDTA). To this, purified Aurora A, 100 µM of a substrate peptide, 20 µM of unlabeled adenosine triphosphate (ATP) and 0.5 µCi of [γ-$^{33}$P] labeled ATP (2,500 Ci/mmole or more) were added, and the mixture was reacted at 30° C. for 20 minutes. Then, 10 µL of 350 mM phosphate buffer was added to the reaction system to stop the reaction. The substrate peptide was adsorbed on a P81 paper filter 96-well plate and then washed with 130 mM phosphate buffer for several times. The radiation activity of the peptide was measured with a liquid scintillation counter. The [γ-$^{33}$P] labeled ATP was purchased from Amersham Biosciences Co., Ltd.

The compound to be tested was added to the reaction system such that a dilution series of the compound in dimethylsulfoxide was first prepared, and 1.1 µL of this solution was added. A control was provided by adding 1.1 µL of DMSO to the reaction system.

Aurora B Inhibitory Action (1) Purification of Aurora B cDNA of Aurora B having histidine tag fused at the amino terminal was integrated into an expression vector, which was then highly expressed in *Escherichia coli* BL21-CodonPlus (DE3)-RIL cells. The *Escherichia coli* cells were recovered and solubilized, and then the histidine-tagged Aurora A protein was adsorbed onto a nickel chelate column and eluted from the column with imidazole. The active fraction was desalted with a desalting column to give a pure enzyme.

(2) Measurement of Activity of Aurora B

For measurement of the activity of Aurora B, the substrate used was Kemptide (Leu-Arg-Arg-Ala-Ser-Leu-Gly) (SEQ.ID.NO.: 1), a synthetic peptide purchased from Sigma-Aldrich, Inc. [Certificate of analysis (Upstate, Inc.)].

Reaction was conducted by a partial modification of the method of activity measurement for Aurora A. The amount of the reaction liquid was 21.1 µL, and the composition of the reaction buffer (R2 buffer) was 50 mM Tris-hydrochloride buffer (pH 7.4)/15 mM magnesium acetate/0.2 mM ethylenediamine-N,N,N',N'-tetraacetate (EDTA). To this, purified Aurora B, 100 µM of a substrate peptide, 100 µM of unlabeled adenosine triphosphate (ATP) and 1 µCi of [γ-$^{33}$P] labeled ATP (2,500 Ci/mmole or more) were added, and the mixture was reacted at 30° C. for 20 minutes. Then, 10 µL of 350 mM phosphate buffer was added to the reaction system to stop the reaction. The substrate peptide was adsorbed on a P81 paper filter 96-well plate and then washed with 130 mM phosphate buffer for several times. The radiation activity of the peptide was measured with a liquid scintillation counter. The [γ-$^{33}$P] labeled ATP was purchased from Amersham Biosciences Co., Ltd.

The compound to be tested was added to the reaction system such that a dilution series of the compound in dimethylsulfoxide was first prepared, and 1.1 µL of this solution was added. A control was provided by adding 1.1 µL of DMSO to the reaction system.

The compound according to the invention exhibits excellent Aurora A selective inhibitory activity, as shown in Table 1.

TABLE 1

| Example | Aurora A inhibitory action ($IC_{50}$, nM) | Aurora B inhibitory action ($IC_{50}$, nM) |
|---|---|---|
| Example 1 | 3 | 640 |
| Example 6 | 6.1 | 2800 |
| Example 7 | 5.7 | 300 |
| Example 9 | 9.8 | 690 |
| Example 10 | 7.1 | 2100 |
| Example 12 | 4.8 | 2300 |
| Example 21 | 1.3 | 260 |
| Example 22 | 1.4 | 590 |
| Example 23 | 1.4 | 330 |
| Example 24 | 1.1 | 190 |

Next, the cell growth suppressive action of the compound of the General Formula (I) according to the invention will be explained below.

Method for Judging the Pharmaceutical Effect Using Cells a) Reagent

Fetal calf serum (FCS) was purchased from Moregate Biotech, and DMEM medium was purchased from Invitrogen Corp. WST-8 was purchased from Kishida Chemical Co., Ltd.

b) Cells

Human cervical cancer cells (HeLa S3) were obtained from the American Type Culture Collection (ATCC).

c) Method of Judging the Effect

Cells were suspended in a DMEM medium containing 10% FCS, and the cell suspension was dispensed to a 96-well plastic plate at a rate of 750 cells/100 microliters per well. The plate was incubated overnight in 5% $CO_2$-95% air at 37° C. A drug was subjected to graded dilution in dimethylsulfoxide and further diluted with a DMEM medium containing 10% FCS. Then, the dilution was dispensed to the plate on which cells had been disseminated, at a rate of 100 microliters per well. The plate was incubated for further three days in 5%

$CO_2$-95% air at 37° C. Cell growth after incubation was measured by the WST-8 method (H. Tominaga, et al., *Anal. Commun.*, 36, 47-50 (1999)). Here, the WST-8 method refers to a method in which 20 microliters of a WST-8 reagent solution is added to each well, incubation is conducted at 37° C. for 45 minutes, the plate is stirred, and the amount of formazan produced is measured by a calorimetric method to determine the inhibitory rate of the drug. The concentration for 50% growth inhibition ($EC_{50}$, μM) of the compound was determined.

incubation is conducted at 37° C. for 45 minutes, the plate is stirred, and the amount of formazan produced is measured by a colorimetric method to determine the inhibitory rate of the drug. The growth inhibitory effects of paclitaxel and of the compound according to the invention were determined, with the value obtained in sole treatment of DMSO being defined as 0%.

The compound according to the invention exhibits excellent cell growth inhibitory effect as well as a synergistic action with paclitaxel against human-derived cancer cells (HeLa S3), as shown in Table 3.

TABLE 3

| Example | Cell growth inhibitory effect by sole administration of paclitaxel (1 nM) (%) | Conc. of the compound of Example (μM) | Cell growth inhibitory effect by sole administration of the compound of Example (%) | Cell growth inhibitory effect by combined administration of paclitaxel and the compound of Example (%) |
|---|---|---|---|---|
| Example 1 | 51.4 | 1.0 | 14.3 | 83.0 |
| Example 6 | 47.2 | 1.0 | 1.7 | 71.7 |
| Example 9 | 47.2 | 1.0 | 12.4 | 79.5 |
| Example 10 | 47.1 | 1.0 | 8.9 | 84.8 |
| Example 21 | 51.4 | 0.1 | 14.9 | 81.3 |

The compound according to the invention exhibits excellent cell growth inhibitory effect against human-derived cancer cells (HeLa S3), as shown in Table 2.

TABLE 2

| Example | Cell growth inhibitory effect (IC50, uM) |
|---|---|
| Example 1 | 5.08 |
| Example 6 | 9.75 |
| Example 10 | 4.60 |
| Example 21 | 0.67 |

Method for Judging the Effect by Combined Use of Drugs in Cells a) Reagent

Fetal calf serum (FCS) was purchased from Moregate Biotech, DMEM medium from Invitrogen Corp., paclitaxel (tradename: Taxol) from Sigma-Aldrich, Inc., and WST-8 from Kishida Chemical Co., Ltd.

b) Cells

Human cervical cancer cells (HeLa S3) were obtained from the American Type Culture Collection (ATCC).

c) Method of Judging the Effect

Cells were suspended in a DMEM medium containing 10% FCS, and the cell suspension was dispensed to two 96-well plastic plates at a rate of 750 cells/100 microliters per well. The plates were incubated overnight in 5% $CO_2$-95% air at 37° C. A drug was subjected to graded dilution in dimethylsulfoxide and further diluted with DMSO or with a DMEM medium containing 10% FCS and also containing 2 nM paclitaxel. Then, the dilutions were each dispensed to one of the plates on which cells had been disseminated, at a rate of 100 microliters per well. The final concentration of paclitaxel at this stage was 1 nM. Also, the concentrations in the case of sole administration of the compound according to the invention were 0.03, 0.1, 0.3, 1 and 3 μM. The plates were incubated for further three days in 5% $CO_2$-95% air at 37° C. Cell growth after incubation was measured by the WST-8 method (H. Tominaga, et al., *Anal. Commun.*, 36, 47-50 (1999)). Here, the WST-8 method refers to a method in which 20 microliters of a WST-8 reagent solution is added to each well, From the above, the compound according to the invention is believed to be useful as an antitumor agent since it exhibits not only excellent cell growth inhibitory action based on Aurora A selective inhibitory activity, but also a synergistic action in combined use with other antitumor agent. Thus, it is believed that a pharmaceutical composition or Aurora A selective inhibitor containing the novel aminopyridine derivative according to the invention or a pharmaceutically acceptable salt or ester thereof, or an antitumor agent containing the compound according to the invention or a pharmaceutically acceptable salt or ester thereof is effective in the treatment of cancer patients.

The above-mentioned pharmaceutical composition and inhibitor, and the above-mentioned antitumor agent may contain a pharmaceutically acceptable carrier or diluent. Here, the "pharmaceutically acceptable carrier or diluent" refers to excipients [e.g., fats, beeswax, semi-solid and liquid polyols, natural or hydrogenated oils, etc.]; water (e.g., distilled water, particularly distilled water for injection, etc.), physiological saline, alcohol (e.g., ethanol), glycerol, polyols, aqueous glucose solution, mannitol, plant oils, etc.); additives [e.g., extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant], and the like.

A suitable tumor for which the therapeutic effect of the compound according to the invention is expected may be exemplified by human solid cancer. Examples of human solid cancer include brain cancer, head and neck cancer, esophageal cancer, thyroid cancer, small cell carcinoma, non-small cell carcinoma, breast cancer, stomach cancer, gallbladder and bile duct cancer, liver cancer, pancreas cancer, colon cancer, rectal cancer, ovarian cancer, chorioepithelioma, uterine cancer, cervical cancer, renal pelvic and ureteral cancer, bladder cancer, prostate cancer, penile cancer, testicular cancer, embryonal cancer, Wilms' tumor, skin cancer, malignant melanoma, neuroblastoma, osteosarcoma, Ewing's tumor, soft tissue sarcoma, and the like.

Next, the above-described "pharmaceutically acceptable salt or ester" will be explained below.

When the compound according to the invention is used as an antitumor agent or the like, it may be also used in a form of pharmaceutically acceptable salt. Typical examples of the pharmaceutically acceptable salt include a salt with an alkali metal such as sodium and potassium; a salt with an inorganic acid, such as hydrochloride, sulfate, nitrate, phosphate, carbonate, hydrogen carbonate, and perchlorate; a salt with an organic acid, such as acetate, propionate, lactate, maleate, fumarate, tartrate, malate, citrate, and ascorbate; a salt with sulfonic acid, such as methanesulfonate, isethionate, benzenesulfonate, and toluenesulfonate; a salt with acidic amino acid, such as aspartate and glutamate; and the like. A pharmaceutically acceptable salt of the Compound (I) is preferably a salt with an inorganic acid, such as hydrochloride, sulfate, nitrate, phosphate, carbonate, hydrogen carbonate, and perchlorate; more preferably hydrochloride.

The process for preparation of a pharmaceutically acceptable salt of the compound according to the invention may be carried out by an appropriate combination of those methods that are conventionally used in the field of organic synthetic chemistry. A specific example thereof is a method in which a solution of the compound according to the invention in its free form is subjected to neutralization titration with an alkaline solution or an acidic solution.

Examples of the ester of the compound according to the invention include methyl ester and ethyl ester. Such esters can be prepared by esterification of a free carboxyl group according to a conventional method.

With regard to each preparation of the combined preparation according to the invention, various preparation forms can be selected, and examples thereof include oral preparations such as tablets, capsules, powders, granules or liquids, or sterilized liquid parenteral preparations such as solutions or suspensions, suppositories, ointments and the like.

Solid preparations can be prepared in the forms of tablet, capsule, granule and powder without any additives, or prepared using appropriate carriers (additives). Examples of such carriers (additives) may include saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

These solid preparations such as tablets, capsules, granules and powders may generally contain, for example, 0.1 to 100% by weight, and preferably 5 to 98% by weight, of the compound of the above Formula (I) as an active ingredient, based on the total weight of the preparation.

Liquid preparations are produced in the forms of suspension, syrup, injection and drip infusion (intravenous fluid) using appropriate additives that are conventionally used in liquid preparations, such as water, alcohol or a plant-derived oil such as soybean oil, peanut oil and sesame oil.

In particular, when the preparation is administered parenterally in a form of intramuscular injection, intravenous injection or subcutaneous injection, appropriate solvent or diluent may be exemplified by distilled water for injection, an aqueous solution of lidocaine hydrochloride (for intramuscular injection), physiological saline, aqueous glucose solution, ethanol, polyethylene glycol, propylene glycol, liquid for intravenous injection (e.g., an aqueous solution of citric acid, sodium citrate and the like) or an electrolytic solution (for intravenous drip infusion and intravenous injection), or a mixed solution thereof.

Such injection may be in a form of a preliminarily dissolved solution, or in a form of powder per se or powder associated with a suitable carrier (additive) which is dissolved at the time of use. The injection liquid may contain, for example, 0.1 to 10% by weight of an active ingredient based on the total weight of the preparation.

Liquid preparations such as suspension or syrup for oral administration may contain, for example, 0.1 to 10% by weight of an active ingredient based on the total weight of the preparation.

Each preparation of the combined preparation according to the invention can be prepared by a person having ordinary skill in the art according to conventional methods or common techniques. For example, a preparation containing another antitumor agent that is used in combination with the compound represented by the above General Formula (I), can be prepared, if the preparation is an oral preparation, for example, by mixing an appropriate amount of the antitumor agent with an appropriate amount of lactose and filling this mixture into hard gelatin capsules which are suitable for oral administration. On the other hand, preparation can be carried out, if the preparation containing the antitumor agent is an injection, for example, by mixing an appropriate amount of the antitumor agent with an appropriate amount of 0.9% physiological saline and filling this mixture in vials for injection.

Also, in the case of a combination preparation containing the compound represented by the above General Formula (I) according to the invention and another antitumor agent, a person having ordinary skill in the art can easily prepare the preparation according to conventional methods or common techniques.

In the process according to the invention, preferred therapeutic unit may vary in accordance with, for example, the administration route of the compound represented by the General Formula (I), the type of the compound represented by the General Formula (I) used, and the dosage form of the compound represented by the General Formula (I) used; the type, administration route and dosage form of the other antitumor agent used in combination; and the type of cells to be treated, the condition of patient, and the like. The optimal treatment under the given conditions can be determined by a person skilled in the art, based on the set conventional therapeutic unit and/or based on the content of the present specification.

In the process according to the invention, the therapeutic unit for the compound represented by the above General Formula (I) may vary in accordance with, specifically, the type of compound used, the type of compounded composition, application frequency and the specific site to be treated, seriousness of the disease, age of the patient, doctor's diagnosis, the type of cancer, or the like. However, as an exemplary reference, the daily dose for an adult may be within a range of, for example, 1 to 1,000 mg in the case of oral administration. In the case of parenteral administration, preferably intravenous administration, and more preferably intravenous drip infusion, the daily dose may be within a range of, for example, 1 to 100 mg/m$^2$ (body surface area). Here, in the case of intravenous drip infusion, administration may be continuously carried out for, for example, 1 to 48 hours. Moreover, the administration frequency may vary depending on the administering method and symptoms, but it is, for example, once to five times a day. Alternatively, periodically intermittent administration such as administration every other day, administration every two days or the like may be employed as well in the administering method. The period of withdraw from medication in the case of parenteral administration is, for example, 1 to 6 weeks.

Although the therapeutic unit for the other antitumor agent used in combination with the compound represented by the General Formula (I) is not particularly limited, it can be determined, if needed, by those skilled in the art according to known literatures. Examples may be as follows.

The therapeutic unit of 5-fluorouracil (5-FU) is such that, in the case of oral administration, for example, 200 to 300 mg per day is administered in once to three times consecutively, and in the case of injection, for example, 5 to 15 mg/kg per day is administered once a day for the first 5 consecutive days by intravenous injection or intravenous drip infusion, and then 5 to 7.5 mg/kg is administered once a day every other day by intravenous injection or intravenous drip infusion (the dose may be appropriately increased or decreased).

The therapeutic unit of S-1 (Tegafur, Gimestat and Ostat potassium) is such that, for example, the initial dose (singe dose) is set to the following standard amount in accordance with the body surface area, and it is orally administered twice a day, after breakfast and after dinner, for 28 consecutive days, followed by withdrawal from medication for 14 days. This is set as one course of administration, which is repeated. The initial standard amount per unit body surface area (Tegafur equivalent) is 40 mg in one administration for an area less than 1.25 $m^2$; 50 mg in one administration for an area of 1.25 $m^2$ to less than 1.5 $m^2$; 60 mg in one administration for an area of 1.5 $m^2$ or more. This dose is appropriately increased or decreased depending on the condition of the patient.

The therapeutic unit for gemcitabine is, for example, 1 g as gemcitabine/$m^2$ in one administration, which is administered by intravenous drip infusion over a period of 30 minutes, and one administration per week is continued for 3 weeks, followed by withdrawal from medication on the fourth week. This is set as one course of administration, which is repeated. The dose is appropriately decreased in accordance with age, symptom or development of side-effects.

The therapeutic unit for doxorubicin (e.g., doxorubicin hydrochloride) is such that, for example, in the case of intravenous injection, 10 mg (0.2 mg/kg) (titer) is administered once a day by intravenous one-shot administration for 4 to 6 consecutive days, followed by withdrawal from medication for 7 to 10 days. This is set as one course of administration, which is repeated two or three times. Here, the total dose is preferably 500 mg (titer)/$m^2$ (body surface area) or less, and it may be appropriately increased or decreased within the range.

The therapeutic unit for etoposide is such that, for example, in the case of intravenous injection, 60 to 100 mg/$m^2$ (body surface area) per day is administered for 5 consecutive days, followed by withdrawal from medication for three weeks (the dose may be appropriately increased or decreased). This is set as one course of administration, which is repeated. Meanwhile, in the case of oral administration, for example, 175 to 200 mg per day is administered for 5 consecutive days, followed by withdrawal from medication for three weeks (the dose may be appropriately increased or decreased). This is set as one course of administration, which is repeated.

The therapeutic unit for docetaxel (docetaxel hydrate) is such that, for example, 60 mg as docetaxel/$m^2$ (body surface area) is administered once a day by intravenous drip infusion over a period of 1 hour or longer at an interval of 3 to 4 weeks (the dose may be appropriately increased or decreased).

The therapeutic unit of paclitaxel is such that, for example, 210 mg/$m^2$ (body surface area) is administered once a day by intravenous drip infusion over a period of 3 hours, followed by withdrawal from medication for at least 3 weeks. This is set as one course of administration, which is repeated. The dose may be appropriately increased or decreased.

The therapeutic unit for cisplatin is such that, for example, in the case of intravenous injection, 50 to 70 mg/$m^2$ (body surface area) is administered once a day, followed by withdrawal from medication for 3 weeks or longer (the dose may be appropriately increased or decreased). This is set as one course of administration, which is repeated.

The therapeutic unit for carboplatin is such that, for example, 300 to 400 mg/$m^2$ is administered once a day by intravenous drip infusion over a period of 30 minutes or longer, followed by withdrawal from medication for at least 4 weeks (the dose may be appropriately increased or decreased). This is set as one course of administration, which is repeated.

The therapeutic unit for oxaliplatin is such that 85 mg/$m^2$ is administered once a day by intravenous injection, followed by withdrawal from medication for two weeks. This is set as one course of administration, which is repeated.

The therapeutic unit for irinotecan (e.g., irinotecan hydrochloride) is such that, for example, 100 mg/$m^2$ is administered once a day by intravenous drip infusion for 3 or 4 times at an interval of one week, followed by withdrawal from medication for at least two weeks.

The therapeutic unit for topotecan is such that, for example, 1.5 mg/$m^2$ is administered once a day by intravenous drip infusion for 5 days, followed by withdrawal from medication for at least 3 weeks.

The therapeutic unit for cyclophosphamide is such that, for example, in the case of intravenous injection, 100 mg is administered once a day by intravenous injection for consecutive days. If the patient can tolerate, the daily dose may be increased to 200 mg. The total dose is 3,000 to 8,000 mg, which may be appropriately increased or decreased. If necessary, it may be injected or infused intramuscularly, intrathoracically or intratumorally.

On the other hand, in the case of oral administration, for example, 100 to 200 mg is administered a day.

The therapeutic unit for gefitinib is such that 250 mg is orally administered once a day.

The therapeutic unit for cetuximab is such that, for example, 400 mg/$m^2$ is administered on the first day by intravenous drip infusion, and then 250 mg/$m^2$ is administered every week by intravenous drip infusion.

The therapeutic unit for bevacizumab is such that, for example, 3 mg/kg is administered every week by intravenous drip infusion.

The therapeutic unit for trastuzumab is such that, for example, typically for an adult, once a day, 4 mg as trastuzumab/kg (body weight) is administered initially, followed by intravenous drip infusion of 2 mg/kg over a period of 90 minutes or longer every week from the second administration.

The therapeutic unit for exemestane is such that, for example, typically for an adult, 25 mg is orally administered once a day after meal.

The therapeutic unit for leuprorelin (e.g., leuprorelin acetate) is such that, for example, typically for an adult, 11.25 mg is subcutaneously administered once in 12 weeks.

The therapeutic unit for imatinib is such that, for example, typically for an adult in the chronic phase of chronic myelogenous leukemia, 400 mg is orally administered once a day after meal.

The therapeutic unit for a combination of 5-FU and leucovorin is such that, for example, 425 mg/m$^2$ of 5-FU and 200 mg/m$^2$ of leucovorin are administered from the first day to the fifth day by intravenous drip infusion, and this course is repeated at an interval of 4 weeks.

The therapeutic unit for sorafenib is such that, for example, 200 mg is orally administered twice a day (400 mg per day) at least 1 hour before or 2 hours after eating.

The therapeutic unit for sunitinib is such that, for example, 50 mg is orally administered once a day for four weeks, followed by 2 weeks off.

WORKING EXAMPLES

In a thin-layer chromatography of Examples and Referential Examples, Silica gel60F254 (Merck) was used as a plate and a UV detector was used in a detecting method. As silica gel for the column, Wakogel™ C-300 or C-200 (Wako Pure Chemical) or NH (FUJI SILYSIA CHEMICAL) was used. In a reversed phase preparative liquid chromatography, Combi-Prep Pro C18 (YMC) was used as a column and a 0.1% aqueous trifluoroacetic acid solution and a 0.1% solution of trifluoroacetic acid in acetonitrile were used in a mobile phase. MS spectra were measured using JMS-SX102A (JEOL) or QUATTROII (Micro Mass). NMR spectra were measured using a spectrometer in a type of Gemini-200 (200 MHz; Varian), Gemini-300 (300 MHz; Varian), VXR-300 (300 MHz; Varian), Mercury 400 (400 MHz; Varian) or Inova 400 (400 MHz; Varian) and all δ values are represented in ppm.

Meanings of abbreviations used in the NMR measurement are as follows.

s: singlet
d: doublet
dd: double doublet
t: triplet
dt: double triplet
q: quartet
qui: quintet
m: multiplet
br: broad
J: coupling constant
Hz: Hertz
DMSO-d$_6$: dimethylsulfoxide-d$_6$
TBS: tert-butyldimethylsilyl group
Ms: methanesulfonyl group
SEM: 2-(trimethylsilyl)ethoxymethyl group
MOM: methoxymethyl group
THP: tetrahydropyran-2-yl group
Boc: tert-butoxycarbonyl group Example 1

Synthesis of 2-(((1S,4S)-5-(3-chloro-2-fluorobenzoyl)-2,5-diazabicyclo[2.2.1]hept-2-yl)methyl)-6-methyl-N-1H-pyrazol-3-ylpyrimidine-4-amine (1) Synthesis of N-(1-tert-butyl-1H-pyrazol-5-yl)-2-chloro-6-methylpyrimidine-4-amine

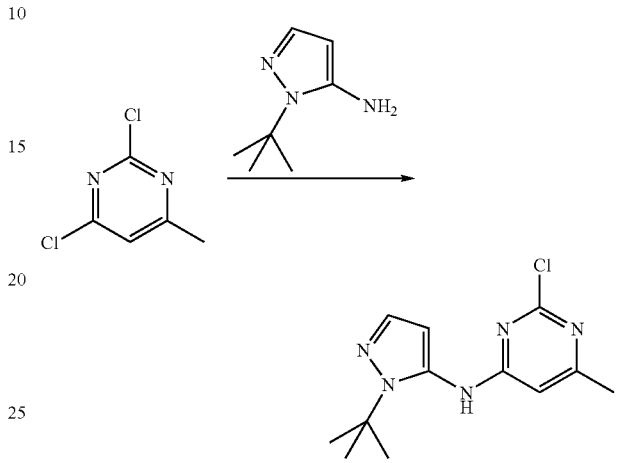

A mixture of 9.70 g of 2,4-dichloro-6-methyl-pyrimidine, 4.50 g of 1-tert-butyl-1H -pyrazol-5-amine obtained in Reference Example 1, 1.79 g of 9,9-dimethyl-4,5-bis(diphenylphosphino)xanthene, 1.60 g of tris(dibenzylideneacetone)dipalladium(0)-chloroform complex, 13.27 g of potassium phosphate, and 100 ml of 1,4-dioxane was stirred at 100° C. for 12 hours, cooled to room temperature, and then diluted with ethyl acetate. An insoluble matter was filtered off using Celite and the resulting ethyl acetate solution was washed with water and saturated brine. The organic layer was dried over anhydrous magnesium sulfate and filtered, and the filtrate was concentrated. The residue was purified by a silica gel column chromatography (eluent: hexane/ethyl acetate=9/1 to 1/1) to give the title compound.

(2) Synthesis of methyl 4-((1-tert-butyl-1H-pyrazol-5-yl)amino)-6-methylpyrimidine-2-carboxylate

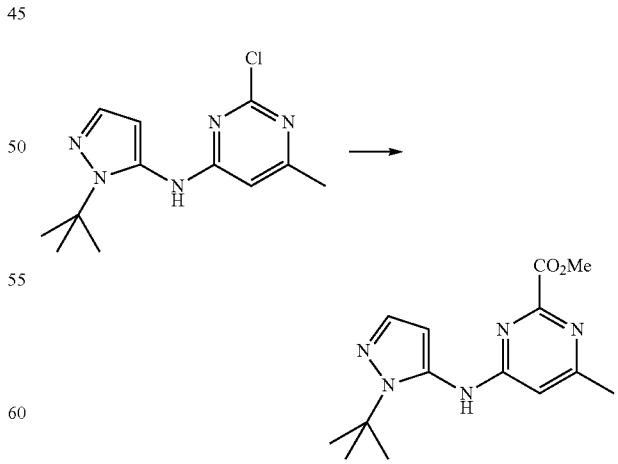

A mixture of 1.93 g of N-(1-tert-butyl-1H-pyrazol-5-yl)-2-chloro-6-methylpyrimidine -4-amine, 328 mg of palladium acetate, 804 mg of 1,1'-bisdiphenylphosphinoferrocene, 920 mg of sodium hydrogen carbonate, 20 ml of methanol and 20 ml of N,N-dimethylformamide was stirred at 100° C. for 16 hours under 3 atmospheric pressure of carbon monoxide, cooled to room temperature, and then diluted with ethyl acetate. An insoluble matter was filtered off using Celite and the resulting ethyl acetate solution was washed with water and saturated brine. The organic layer was dried over anhydrous magnesium sulfate and filtered, and the filtrate was concentrated. The residue was purified by a silica gel column chromatography (eluent: hexane/ethyl acetate=7/1 to 0/1) to give the title compound.

(3) Synthesis of 4-((1-tert-butyl-1H-pyrazol-5-yl)amino)-6-methylpyrimidine-2-yl)-methanol

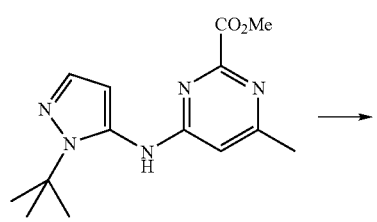

To a mixture of 1.3 g of methyl 4-((1-tert-butyl-1H-pyrazol-5-yl)amino)-6-methylpyrimidine-2-carboxylate and 13 ml of methanol was added 341 mg of sodium borohydride followed by stirring at room temperature for 24 hours. Water was added to the reaction mixture, and then the mixture was extracted with ethyl acetate. The resulting ethyl acetate solution was dried over anhydrous magnesium sulfate and filtered, and the filtrate was concentrated to give the title compound.

(4) Synthesis of N-(1-tert-butyl-1H-pyrazol-5-yl)-2-(((1S,4S)-5-(3-chloro-2-fluorobenzoyl) -2,5-diazabicyclo[2.2.1]hept-2-yl)methyl)-6-methylpyrimidine-4-amine

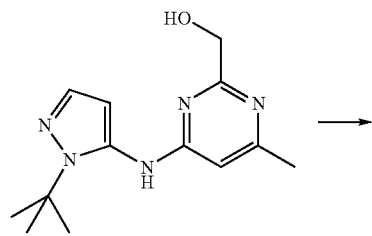

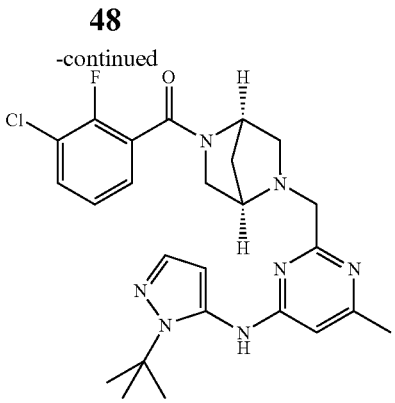

To a mixture of 56 mg of 4-((1-tert-butyl-1H-pyrazol-5-yl)amino)-6-methylpyrimidin -2-yl)-methanol, 112 μl of N,N-diisopropylethylamine and 1.5 ml of chloroform was added 22 μl of methanesulfonyl chloride at room temperature followed by stirring for 4 hour. To the reaction mixture was added 60 mg of (1S,4S)-5-(3-chloro-2-fluorobenzoyl)-2,5-diazabicyclo[2.2.1]heptane obtained in Reference Example 2 was added followed by stirring at 60° C. for 16 hours. The resulting reaction mixture was washed with aqueous sodium bicarbonate and saturated brine. The resulting organic layer was dried over anhydrous magnesium sulfate and filtered, and then the filtrate was concentrated in vacuo to obtain the title compound.

(5) Synthesis of 2-(((1S,4S)-5-(3-chloro-2-fluorobenzoyl)-2,5-diazabicyclo[2.2.1]hept-2-yl)methyl)-6-methyl-N-1H-pyrazol-3-ylpyrimidine-4-amine

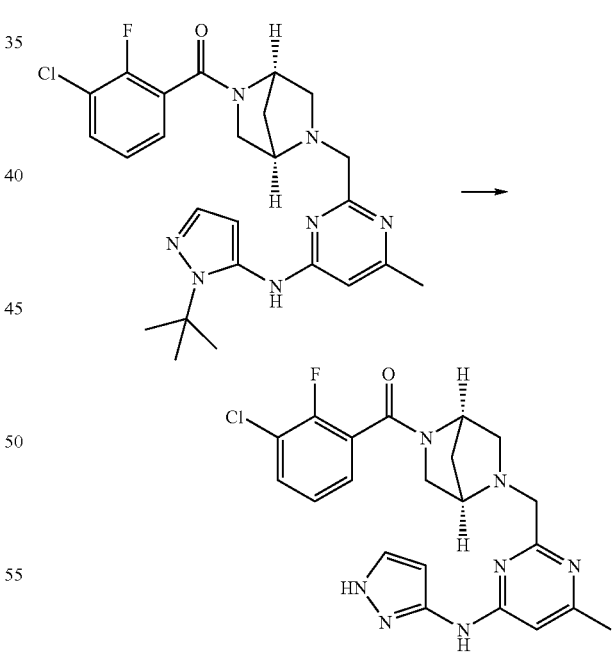

101 mg of N-(1-tert-butyl-1H-pyrazol-5-yl)-2-(((1S,4S)-5-(3-chloro-2-fluorobenzoyl) -2,5-diazabicyclo[2.2.1]hept-2-yl)methyl)-6-methylpyrimidine-4-amine was dissolved in 1 ml of formic acid followed by stirring at 100° C. for 3 hours. The reaction solution was concentrated in vacuo, diluted with ethyl acetate, and then washed with saturated sodium bicarbonate, water and saturated brine. The resulting organic layer was dried over magnesium sulfate and filtered, and the filtrate was concentrated. The resulting residue was purified by a reversed phase preparative liquid chromatography to give the title compound.

Spectral data of the title compound are as follows.

$^1$H-NMR (CD$_3$OD) δ: 7.76-7.55 (m, 2H), 7.54-7.45 (m, 1H), 7.34 (t, J=7.6 Hz, 1H), 7.14-6.82 (br, 1H), 6.39-6.22 (m, 1H), 5.09-4.40 (m, 4H), 4.05-3.48 (m, 4H), 2.50-2.46 (3H, m), 2.45-2.22 (m, 2H).

Mass: 442 (M+1)$^+$.

Examples 2 to 9 were synthesized in the same manner as in Example 1 as follows.

Example 2

Synthesis of 2-(((1S,4S)-5-(2-fluoro-3-(trifluoromethyl)benzoyl)-2,5-diazabicyclo[2.2.1]hept-2-yl)methyl)-6-methyl-N-1H-pyrazol-3-ylpyrimidine-4-amine $^1$H-NMR (CDCl$_3$) δ: 8.45-8.00 (br, 1H), 7.72-7.61 (m, 2H), 7.51 (dd, J=7.3, 2.4 Hz, 1H), 7.32 (t, J=8.0 Hz, 1H), 6.87 (s, 1H), 6.28 and 6.21 (each d, J=2.4 Hz, total 1H), 4.94-2.80 (m, 8H), 2.41-2.36 (m, 3H), 2.15-2.04 (m, 1H), 1.90-1.80 (m, 1H).

Mass: 476 (M+1)$^+$.

Example 3

Synthesis of 2-(((1S,4S)-5-(2,3-dichlorobenzoyl)-2,5-diazabicyclo[2.2.1]hept-2-yl)methyl)-6-methyl-N-1H-pyrazol-3-ylpyrimidine-4-amine Mass: 458 (M+1)$^+$.

Example 4

Synthesis of 2-(((1S,4S)-5-(3-bromo-2-fluorobenzoyl)-2,5-diazabicyclo[2.2.1]hept-2-yl)methyl)-6-methyl-N-1H-pyrazol-3-ylpyrimidine-4-amine Mass: 486, 488 (M+1)$^+$.

Example 5

Synthesis of 2-(((1R,4R)-5-(2-fluoro-3-(trifluoromethyl)benzoyl)-2,5-diazabicyclo[2.2.1]hept-2-yl)methyl)-6-methyl-N-1H-pyrazol-3-ylpyrimidine-4-amine Mass: 476 (M+1)$^+$.

Example 6

Synthesis of 2-(((1S,4S)-5-(2-fluoro-3-(trifluoromethyl)benzoyl)-2,5-diazabicyclo[2.2.1]hept-2-yl)methyl)-N-1H-pyrazol-3-ylpyrimidine-4-amine $^1$H-NMR (CDCl$_3$) δ: 8.31 (dd, J=10.7, 5.9 Hz, 1H), 8.40-7.95 (br, 1H), 7.80-7.60 (m, 2H), 7.52 (d, J=5.4 Hz, 1H), 7.35-7.28 (m, 1H), 7.00 (s, 1H), 6.24 (d, J=13.7 Hz, 1H), 4.94-1.95 (m, 8H), 1.90-1.51 (m, 2H).

Mass: 462 (M+1)$^+$.

Example 7

Synthesis of 2-(((1S,4S)-5-(3-chloro-2-fluorobenzoyl)-2,5-diazabicyclo[2.2.1]hept-2-yl)methyl)-6-methyl-N-(5-methyl-1H-pyrazol-3-yl)pyrimidine-4-amine $^1$H-NMR (CDCl$_3$) δ: 7.62-7.40 (m, 2H), 7.40-7.22 (m, 1H), 7.15 (t, J=7.8 Hz, 1H), 7.02-6.88 (m, 1H), 5.99 and 5.92 (each s, total 1H), 4.93-3.73 (m, 5H), 3.62-3.50 (m, 1H), 3.29-2.80 (m, 2H), 2.45-2.28 (m, 6H), 2.20-1.90 (m, 1H), 1.85 (d, J=10.7 Hz, 1H).

Mass: 456 (M+1)$^+$.

Example 8

Synthesis of 2-(((1S,4S)-5-(2-fluoro-3-(trifluoromethyl)benzoyl)-2,5-diazabicyclo[2.2.1]hept-2-yl)methyl)-6-methyl-N-(5-methyl-1H-pyrazol-3-yl)pyrimidine-4-amine $^1$H-NMR (CDCl$_3$) δ: 7.80-7.50 (m, 3H), 7.32 (t, J=7.8 Hz, 1H), 6.98-6.88 (br, 1H), 5.98 and 5.92 (each s, total 1H), 4.94-3.74 (m, 5H), 3.62-3.50 (m, 1H), 3.31-2.76 (m, 2H), 2.43-2.28 (m, 6H), 2.17-2.04 (m, 1H), 1.85 (d, J=9.3 Hz, 1H).

Mass: 490 (M+1)$^+$.

Example 9

Synthesis of 2-(((1S,4S)-5-(3-chloro-2-fluorobenzoyl)-2,5-diazabicyclo[2.2.1]hept-2-yl)methyl)-N-(5-methyl-1H-pyrazol-3-yl)pyrimidine-4-amine $^1$H-NMR (CDCl$_3$) δ: 8.30 (t, J=7.1 Hz, 1H), 8.10-7.50 (br, 1H), 7.48-7.43 (m, 1H), 7.32 (t, J=6.8 Hz, 1H), 7.15 (t, J=7.8 Hz, 1H), 7.02 (s, 1H), 6.10 and 5.95 (each s, total 1H), 4.92-2.72 (m, 8H), 2.38-2.25 (m, 3H), 2.18-2.07 (m, 1H), 1.88-1.70 (m, 1H).

Mass: 442 (M+1)$^+$.

Example 10

Synthesis of 6-(((1S,4S)-5-(2,3-dichlorobenzoyl)-2,5-diazabicyclo[2.2.1]hept-2-yl)methyl)-N-1H-pyrazol-3-ylpyrazine-2-amine trifluoroacetate (1) Synthesis of 6-chloro-N-(1-((2-(trimethylsilyl)ethoxy)methyl)-1H-pyrazol-3-yl)pyrazin-2-amine

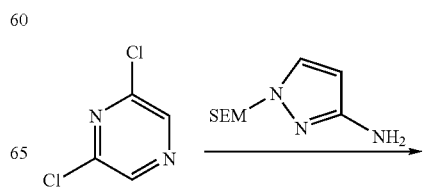

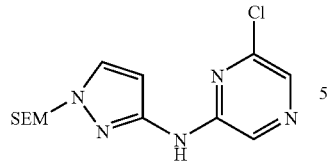

A mixture of 1.78 g of 2,6-dichloropyrazine, 2.84 g of 1-((2-(trimethylsilyl)ethoxy)methyl)-1H-pyrazol-3-amine obtained in Reference Example 3, 690 mg of 9,9-dimethyl-4,5-bis(diphenylphosphino)xanthene, 620 mg of tris(dibenzylideneacetone)dipalladium(0)-chloroform complex, 5.07 g of potassium phosphate, and 25 ml of 1,4-dioxane was stirred at 100° C. for 2 hours, cooled to room temperature, and then diluted with ethyl acetate. An insoluble matter was filtered off using Celite and the resulting ethyl acetate solution was washed with water and brine. The organic layer was dried over anhydrous magnesium sulfate and filtered, and the filtrate was concentrated. The residue was purified by a silica gel column chromatography (eluent: hexane/ethyl acetate=10/1 to 1/1) to give the title compound.

(2) Synthesis of methyl 6-((1-((2-(trimethylsilyl)ethoxy)methyl)-1H-pyrazol-3-yl)amino)pyrazine-2-carboxylate

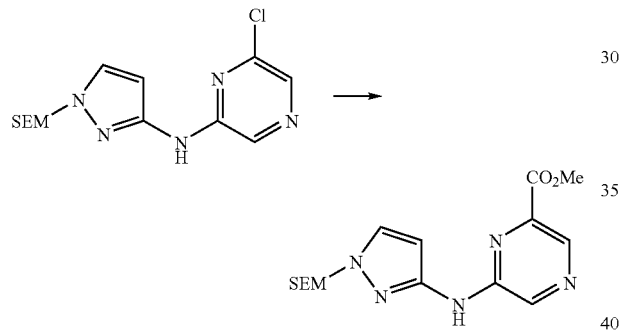

A mixture of 2.41 g of 6-chloro-N-(1-((2-(trimethylsilyl)ethoxy)methyl)-1H-pyrazol-3-yl)pyrazin-2-amine, 320 mg of palladium acetate, 790 mg of 1,1'-bisdiphenylphosphinoferrocene, 890 mg of sodium hydrogen carbonate, 10 ml of methanol and 10 ml of N,N-dimethylformamide was stirred at 100° C. for 15 hours under 3 atmospheric pressure of carbon monoxide, cooled to room temperature, and then diluted with ethyl acetate. An insoluble matter was filtered off using Celite and the resulting ethyl acetate solution was washed with water and brine. The organic layer was dried over anhydrous magnesium sulfate and filtered, and the filtrate was concentrated. The residue was purified by a silica gel column chromatography (eluent: hexane/ethyl acetate=10/1 to 1/1) to give the title compound.

(3) Synthesis of 6-((1-((2-(trimethylsilyl)ethoxy)methyl)-1H-pyrazol-3-yl)amino)pyrazine-2-carboxylic Acid

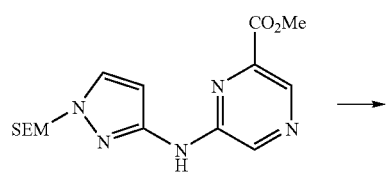

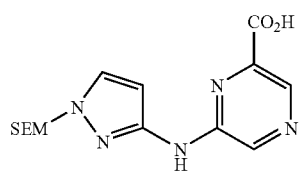

To a mixture of 52 mg of methyl 6-((1-((2-(trimethylsilyl)ethoxy)methyl)-1H-pyrazol -3-yl)amino)pyrazine-2-carboxylate, 0.5 ml of tetrahydrofuran and 1 ml of methanol was added an aqueous sodium hydroxide solution (1.0 M, 0.5 ml), followed by stirring at room temperature for 15 hours. The obtained reaction solution was diluted with ethyl acetate, and then washed with aqueous ammonium chloride and brine. The organic layer was dried over anhydrous magnesium sulfate and filtered, and filtrate was concentrated to give the title compound.

(4) Synthesis of (6-((1-((2-(trimethylsilyl)ethoxy)methyl)-1H-pyrazol-3-yl)amino)pyrazin-2-yl)methanol

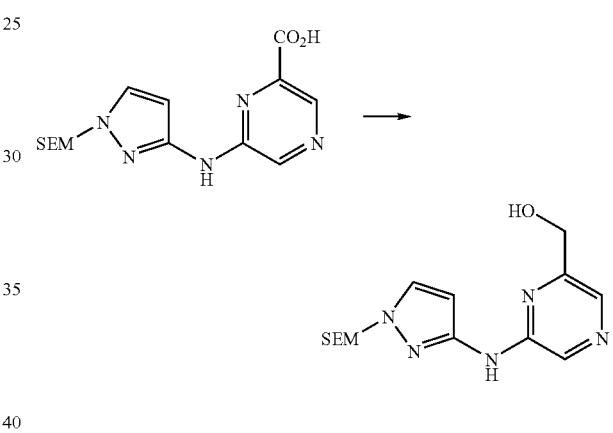

To a mixture of 28 mg of 6-((1-((2-(trimethylsilyl)ethoxy)methyl)-1H-pyrazol-3-yl)amino)pyrazine-2-carboxylic acid and 1 ml of N,N-dimethylformamide was added 84 mg of N,N'-carbonyldiimidazole, followed by stirring at room temperature for 15 hours. Then, 200 μl of an aqueous solution of 20 mg of sodium borohydride was added thereto and the resulting mixture was stirred. Water was added to the reaction mixture, and then the mixture was extracted with ethyl acetate. The resulting ethyl acetate solution was dried over anhydrous magnesium sulfate and filtered, and the filtrate was concentrated. The residue was purified by a silica gel column chromatography (eluent: chloroform to chloroform/methanol=10/1) to give the title compound.

(5) Synthesis of 6-(((1S,4S)-5-(2,3-dichlorobenzoyl)-2,5-diazabicyclo[2.2.1]hept-2-yl)methyl)-N-(1-((2-(trimethylsilyl)ethoxy)methyl)-1H-pyrazol-3-yl)pyrazine-2-amine

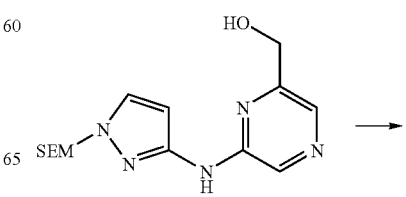

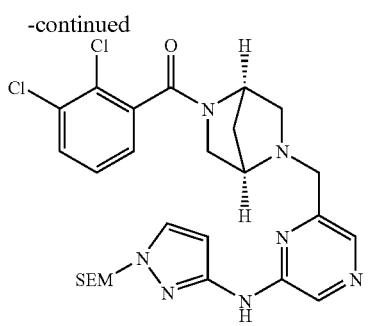

To a mixture of 16 mg of (6-(((1-((2-(trimethylsilyl)ethoxy)methyl)-1H-pyrazol-3-yl)amino)pyrazin-2-yl)methanol, 42 µl of N,N-diisopropylethylamine and 1 ml of chloroform was added 11 µl of methanesulfonyl chloride at room temperature followed by stirring for 3 hour. To the reaction mixture was added 42 µl of N,N-diisopropylethylamine, and then 62 mg of (1S,4S)-2-(2,3-dichlorobenzoyl)-2,5-diazabicyclo[2.2.1]heptane hydrochloride obtained in Reference Example 2 was added thereto followed by stirring at 50° C. for 16 hours. The resulting reaction mixture was washed with aqueous sodium bicarbonate and brine. The resulting organic layer was dried over anhydrous magnesium sulfate and filtered, and then the filtrate was concentrated in vacuo. The resulting residue was purified by a silica gel column chromatography (eluent: chloroform to chloroform/methanol=20/1) to obtain the title compound.
(6) Synthesis of 6-(((1S,4S)-5-(2,3-dichlorobenzoyl)-2,5-diazabicyclo[2.2.1]hept-2-yl)methyl)-N-1H-pyrazol-3-ylpyrazine-2-amine Trifluoroacetate

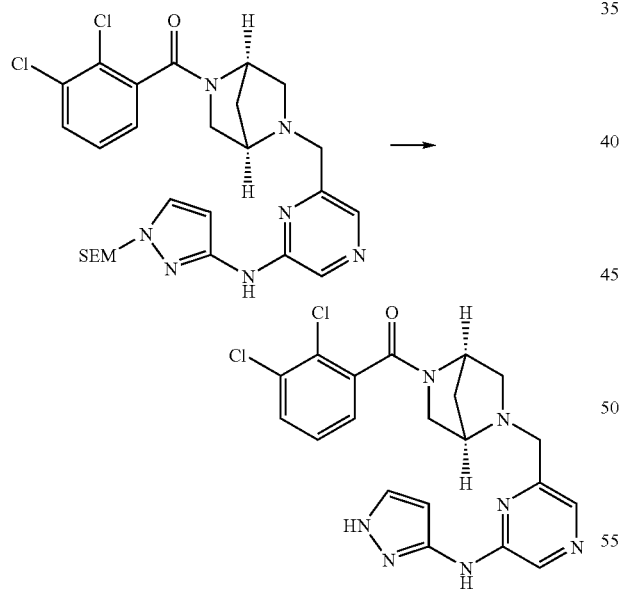

19 mg of 6-(((1S,4S)-5-(2,3-dichlorobenzoyl)-2,5-diazabicyclo[2.2.1]hept-2-yl)methyl)-N-(1-((2-(trimethylsilyl)ethoxy)methyl)-1H-pyrazol-3-yl)pyrazine-2-amine was dissolved in 1 ml of trifluoroacetic acid and 0.1 ml of water followed by stirring at room temperature for 15 hours. The reaction solution was concentrated in vacuo, diluted with ethyl acetate, and then washed with saturated sodium bicarbonate, water and brine. The resulting organic layer was dried over magnesium sulfate and filtered, and the filtrate was concentrated. The resulting residue was purified by a silica gel column chromatography (eluent: chloroform to chloroform/methanol=5/1) to give the title compound.
Spectral data of the title compound are as follows.
$^1$H-NMR (CDCl$_3$) δ: 8.52-8.47 (m, 1H), 8.14 (s, 1H), 7.76-7.69 (m, 1H), 7.57-7.49 (m, 4H), 6.35-6.27 (m, 1H), 5.38-3.13 (m, 8H), 2.38-1.70 (m, 2H).
Mass: 444 (M+1)$^+$.
Examples 11 to 20 were synthesized in the same manner as in Example 10 as follows.

Example 11

Synthesis of 6-(((1R,4R)-5-(2,3-dichlorobenzoyl)-2,5-diazabicyclo[2.2.1]hept-2-yl)methyl)-N-1H-pyrazol-3-yl)pyrazine-2-amine Mass: 444 (M+1)$^+$.

Example 12

Synthesis of 6-(((1R,4R)-5-(2-chloro-3-(trifluoromethyl)benzoyl)-2,5-diazabicyclo[2.2.1]hept-2-yl)methyl)-N-1H pyrazol-3-yl)pyrazine-2-amine Mass: 478 (M+1)$^+$.

Example 13

Synthesis of 6-(((1R,4R)-5-(3-bromo-2-fluorobenzoyl)-2,5-diazabicyclo[2.2.1]hept-2-yl)methyl)-N-1H-pyrazol-3-yl)pyrazine-2-amine Mass: 472, 474 (M+1)$^+$.

Example 14

Synthesis of 6-(((1R,4R)-5-(2-cyano-3-(trifluoromethyl)benzoyl)-2,5-diazabicyclo[2.2.1]hept-2-yl)methyl)-N-1H-pyrazol-3-yl)pyrazine-2-amine Mass: 469 (M+1)$^+$.

Example 15

Synthesis of 6-(((1S,4S)-5-(3-bromo-2-fluorobenzoyl)-2,5-diazabicyclo[2.2.1]hept-2-yl)methyl)-N-(5-methyl-1H-pyrazol-3-yl)pyrazine-2-amine Mass: 486, 488 (M+1)$^+$.

Example 16

Synthesis of 6-(((1S,4S)-5-(2-chloro-3-(trifluoromethyl)benzoyl)-2,5-diazabicyclo[2.2.1]hept-2-yl)methyl)-N-(5-methyl-1H-pyrazol-3-yl)pyrazine-2-amine Mass: 492 (M+1)$^+$.

Example 17

Synthesis of 6-(((1S,4S)-5-(3-chloro-2-cyanobenzoyl)-2,5-diazabicyclo[2.2.1]hept-2-yl)methyl)-N-(5-methyl-1H-pyrazol-3-yl)pyrazine-2-amine Mass: 449 (M+1)$^+$.

Example 18

Synthesis of 6-(((1S,4S)-5-(2-cyano-3-(trifluoromethyl)benzoyl)-2,5-diazabicyclo[2.2.1]hept-2-yl)methyl)-N-(5-methyl-1H-pyrazol-3-yl)pyrazine-2-amine Mass: 483 (M+1)$^+$.

Example 19

Synthesis of 6-(((1R,4R)-5-(3-bromo-2-fluorobenzoyl)-2,5-diazabicyclo[2.2.1]hept 2-yl)methyl)-N-(5-methyl-1H-pyrazol-3-yl)pyrazine-2-amine Mass: 486, 488 (M+1)$^+$.

Example 20

Synthesis of 6-(((1R,4R)-5-(2,3-dichlorobenzoyl)-2,5-diazabicyclo[2.2.1]hept-2-yl)methyl)-N-(5-methyl-1H-pyrazol-3-yl)pyrazine-2-amine Mass: 458 (M+1)$^+$.

Example 21

Synthesis of 2-(((1S,4S)-5-(3-chloro-2-fluorobenzoyl)-2,5-diazabicyclo[2.2.1]hept-2-yl)methyl)-N,N-dimethyl-6-(1,3-thiazol-2-ylamino)isonicotinamide (1) Synthesis of dimethyl 4-bromopyridine-2,6-dicarboxylate

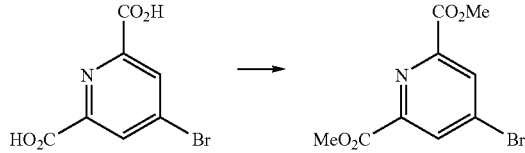

A mixture of 7.38 g of 4-bromopyridine-2,6-dicarboxylic acid synthesized in the method of Tetrahedron lett., 42 (29), 4849 (2001), 10 ml of a hydrochloric acid-methanol reagent and 100 ml of methanol was stirred at room temperature for 15 hours, and the reaction mixture was concentrated in vacuo. Ethyl acetate was added to the residue and the mixture was washed three times with a mixed solution of brine-saturated sodium bicarbonate (1:1). The organic layer was dried over anhydrous magnesium sulfate and was filtered. The filtrate was then concentrated in vacuo to give the title compound.

(2) Synthesis of 4-bromo-6-(methoxycarbonyl)pyridine-2-carboxylic Acid

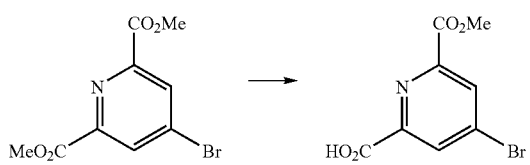

A mixture of 6.09 g of dimethyl 4-bromopyridine-2,6-dicarboxylate, 1.08 g of potassium hydroxide, 200 ml of methanol and 20 ml of methylene chloride was stirred at room temperature for 3 hours, and 200 ml of diethylether was added thereto. The resulting white solid was filtered, and then washed with ether. The obtained white solid was dissolved in water, and then 12 ml of hydrochloric acid (2 M) was added thereto. The resulting mixture was extracted with chloroform. The organic layer was dried over anhydrous magnesium sulfate and filtered, and the filtrate was concentrated in vacuo to give the title compound.

(3) Synthesis of methyl 4-bromo-6-tert-butoxycarbonylaminopyridine-2-carboxylate

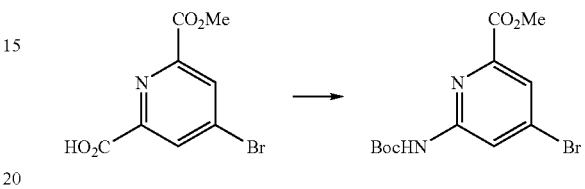

To a mixture of 4.62 g of 4-bromo-6-(methoxycarbonyl)pyridine-2-carboxylic acid, 2.97 ml of triethylamine, 25 ml of t-butanol and 70 ml of 1,4-dioxane was added 4.59 ml of diphenylphosphoryl azide at room temperature. The reaction mixture was heated under reflux for 3 hours and cooled to room temperature. Water was added thereto and the resulting mixture was extracted with ethyl acetate. The obtained ethyl acetate solution was washed with water and brine, dried over anhydrous sodium sulfate and filtered. The filtrate was concentrated in vacuo to give the title compound.

(4) Synthesis of methyl 6-amino-4-bromopyridine-2-carboxylate

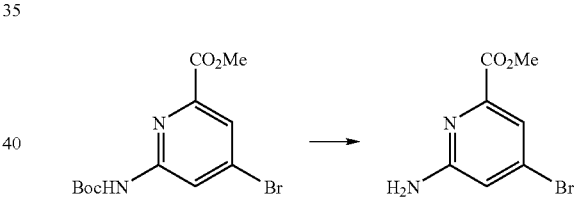

7.23 g of methyl 4-bromo-6-t-butoxycarbonylamino-pyridine-2-carboxylate was dissolved in 30 ml of chloroform, and then 15 ml of trifluoroacetic acid was added thereto, followed by stirring at room temperature for 1 hour. After concentrating the reaction mixture, the residue was dissolved in ethyl acetate and washed with saturated sodium bicarbonate and brine. The organic layer was dried over anhydrous magnesium sulfate, filtered, and then concentrated in vacuo. The residue was purified by a silica gel column chromatography (eluent: chloroform to chloroform/methanol=20/1) to give the title compound.

(5) Synthesis of methyl 6-(3-benzoylthioureido)-4-bromopyridine-2-carboxylate

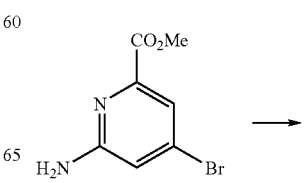

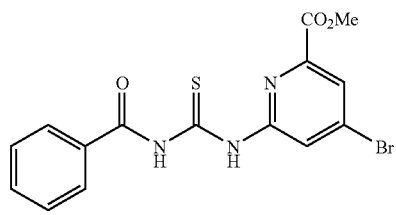

2.74 g of methyl 6-amino-4-bromopyridine-2-carboxylate was dissolved in 15 ml of tetrahydrofuran and 1.63 ml of benzoyl isothiocyanate was added thereto, followed by stirring at room temperature for 13 hours. To the reaction mixture was added 40 ml of hexane. The resulting solid was filtered and washed with hexane. The obtained solid was dried in vacuo to give the title compound.

(6) Synthesis of methyl 4-bromo-6-(1,3-thiazol-2-ylamino)pyridine-2-carboxylate

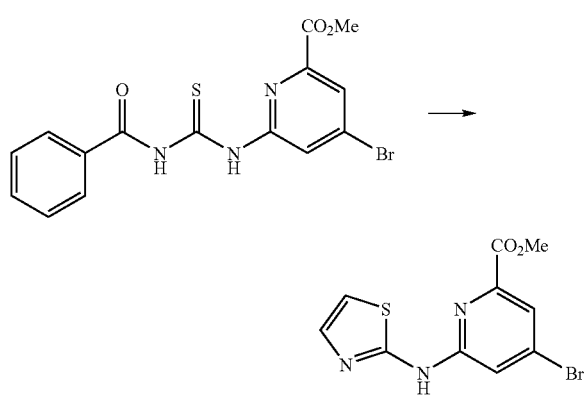

To a mixture of 2.37 g of methyl 6-(3-benzoylthioureido)-4-bromopyridine-2-carboxylate, 20 ml of tetrahydrofuran and 40 ml of methanol was added 673 mg of potassium hydroxide. The reaction mixture was stirred at room temperature for 1.5 hours, and acidified with a hydrochloric acid-methanol solution. The solvents were concentrated in vacuo. The resulting residue was dissolved in 60 ml of 1,4-dioxane and 3.53 ml of a 40% chloroacetaldehyde aqueous solution was added thereto. After the reaction mixture was heated under reflux for 1 hour, 40 ml of a hydrochloric acid-methanol solution and 60 ml of methanol were added thereto at room temperature, and the resulting mixture was stirred overnight. The reaction mixture was concentrated in vacuo and the residue was recrystallized from methanol-diethyl ether to give the title compound.

(7) Synthesis of methyl 4-bromo-6-((methoxymethyl)(1,3-thiazol-2-yl)amino)pyridine-2-carboxylate

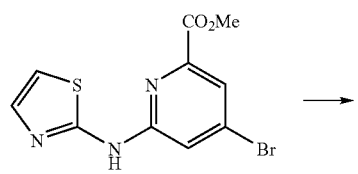

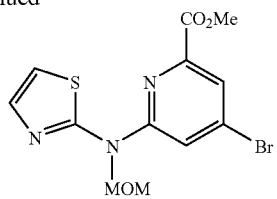

To a mixture of 34.3 g of methyl 4-bromo-6-(1,3-thiazol-2-ylamino)pyridine-2-carboxylate and 440 ml of N,N-diisopropylethylamine was added 5.29 g of sodium hydride (60%, in oil) under an ice bath followed by stirring at the ambient temperature for 30 minutes. To the reaction mixture was added 9.9 ml of chloromethylmethyl ether followed by stirring at the ambient temperature for 4 hours. To the reaction mixture was added 4.52 g of sodium hydride (60%, in oil) and 8.3 ml of chloromethylmethyl ether, followed by further stirring for three hours. After warming to room temperature, to the reaction mixture was added saturated aqueous sodium bicarbonate. The precipitate was filtered off and washed with water. The filtrate was extracted with ethyl acetate and then the organic layer was washed with water and saturated brine. The resulting organic layer was dried over anhydrous sodium sulfate, filtered and the filtrate was concentrated in vacuo. The resulting residue was purified by a silica gel column chromatography (eluent: hexane/ethyl acetate=9/1 to 3/1) to give the title compound as a pale yellow solid.

(8) Synthesis of 4-bromo-6-((methoxymethyl)(1,3-thiazol-2-yl)amino)pyridin-2-yl)-methanol

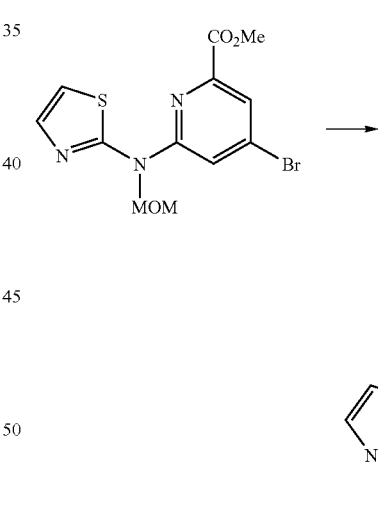

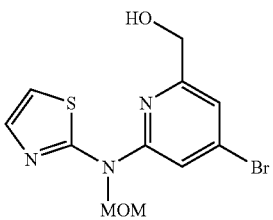

20.4 g of methyl 4-bromo-6-((methoxymethyl)(1,3-thiazol-2-yl)amino)pyridin-2-carboxylate was dissolved in 290 ml of tetrahydrofuran, 290 ml of lithium borohydride in THF (2 mol/l) was added thereto and the mixture was stirred at 50° C. for 2 hours. To the reaction mixture was added saturated aqueous ammonium hydrochloride under an ice bath and the resulting solution was evaporated in vacuo. The residue was extracted with chloroform and the organic layer was washed with saturated aqueous ammonium hydrochloride. The resulting organic layer was dried over anhydrous sodium sulfate and filtered, and the filtrate was concentrated in vacuo to give the title compound.

(9) Synthesis of 4-bromo-6-(((tert-butyl(dimethyl)silyl)oxy)methyl)-N-(methoxymethyl) -N-1,3-thiazol-2-ylpyridine-2-amine

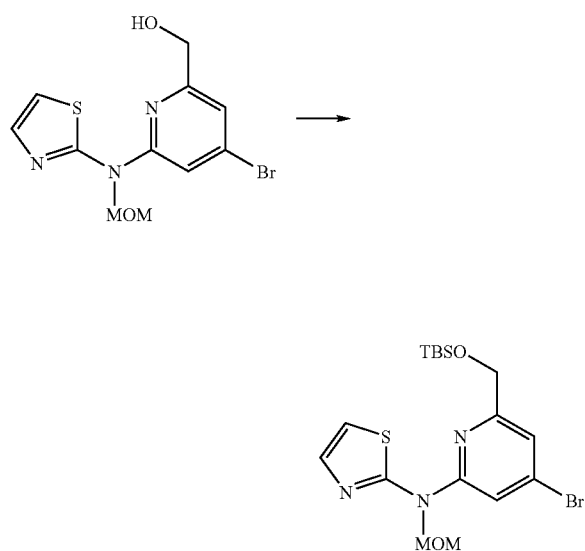

18.5 g of (4-bromo-6-((methoxymethyl)(1,3-thiazol-2-yl)amino)pyridin-2-yl)-methanol was dissolved in 110 mL of dimethylformamide and 9.64 g of imidazole was added thereto. Under cooling with an ice bath, 10.2 g of tert-butyldimethylsilyl chloride was added thereto followed by stirring at room temperature for 3 hours. The reaction solution was diluted with ethyl acetate and washed with water and brine. The resulting organic layer was dried over magnesium sulfate and filtered, and the filtrate was concentrated. The resulting residue was purified by a silica gel column chromatography (eluent: hexane/ethyl acetate=9/1 to 4/1) to give the title compound.

(10) Synthesis of methyl 2-(((tert-butyl(dimethyl)silyl)oxy)methyl)-6-((methoxymethyl)(1,3-thiazol-2-yl)amino)isonicotinic Acid

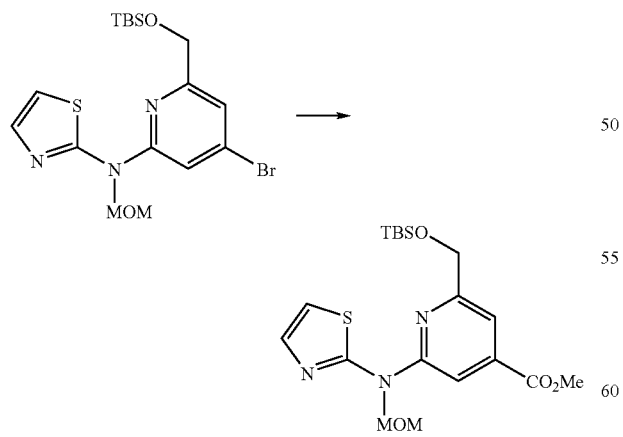

In the same manner as in Example 1-(2), the title compound was obtained using 4-bromo-6-((((tert-butyl(dimethyl)silyl)oxy)methyl)-N-(methoxymethyl)-N-1,3-thiazol-2-ylpyridine-2-amine

(11) Synthesis of methyl 2-(hydroxymethyl)-6-((methoxymethyl)(1,3-thiazol-2-yl)amino)isonicotinic Acid

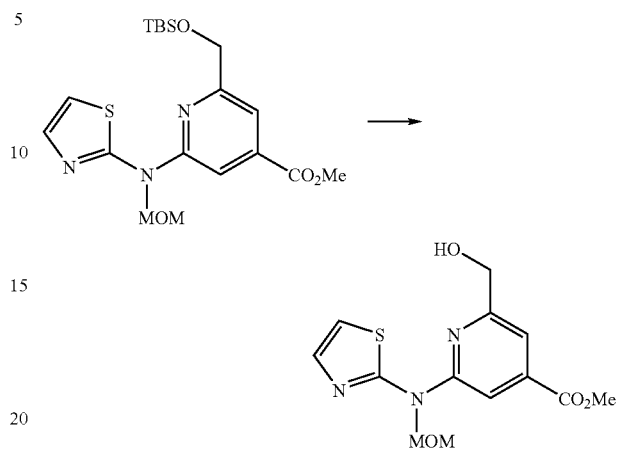

To the mixture of 201 mg of methyl 2-((((tert-butyl(dimethyl)silyl)oxy)methyl)-6-((methoxymethyl)(1,3-thiazol-2-yl)amino)isonicotinic acid, 3.2 ml of chloroform and 3.2 ml of methanol was added 3.2 ml of trifluoroacetic acid under cooling with an ice bath. After stirring at room temperature for 2 hours, the reaction mixture was concentrated. The resulting residue was diluted with ethyl acetate and then the resulting solution was washed with aqueous sodium hydrogen carbonate and saturated brine. The organic layer was dried over anhydrous magnesium sulfate and filtered, and the filtrate was concentrated to give the title compound.

(12) Synthesis of methyl 2-(((1S,4S)-5-(3-chloro-2-fluorobenzoyl)-2,5-diazabicyclo[2.2.1]hept-2-yl)methyl)-6-((methoxymethyl)(1,3-thiazol-2-yl)amino)isonicotinic acid

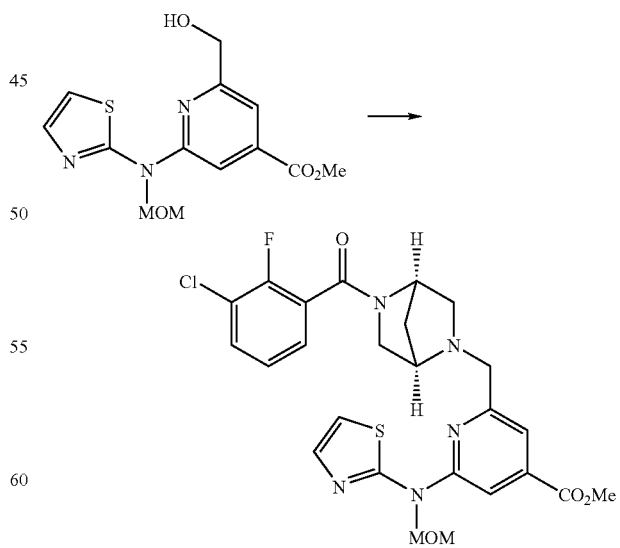

In the same manner as in Example 1-(5), the title compound was obtained using methyl 2-(hydroxymethyl)-6-((methoxymethyl)(1,3-thiazol-2-yl)amino)isonicotinic acid

(13) Synthesis of 2-(((1S,4S)-5-(3-chloro-2-fluorobenzoyl)-2,5-diazabicyclo[2.2.1]hept-2-yl)methyl)-6-((methoxymethyl)(1,3-thiazol-2-yl)amino)isonicotinic acid

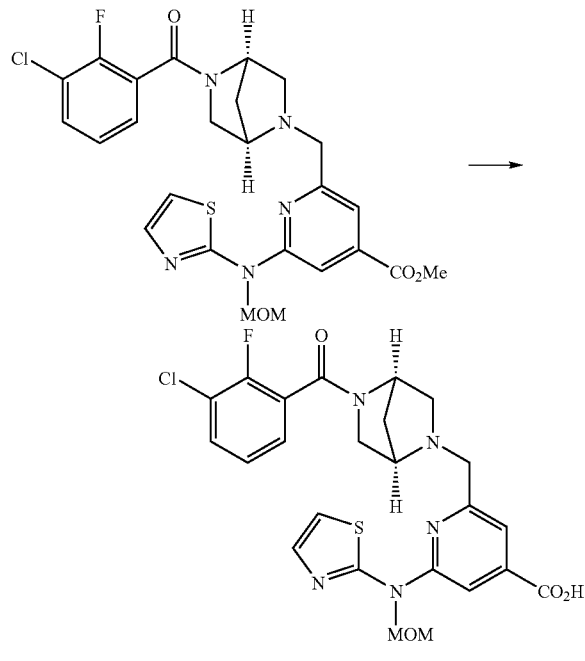

In the same manner as in Example 10-(3), the title compound was obtained using methyl 2-(((1S,4S)-5-(3-chloro-2-fluorobenzoyl)-2,5-diazabicyclo[2.2.1]hept-2-yl)methyl)-6-((methoxymethyl)(1,3-thiazol-2-yl)amino)isonicotinic acid

(14) Synthesis of 2-(((1S,4S)-5-(3-chloro-2-fluorobenzoyl)-2,5-diazabicyclo[2.2.1]hept-2-yl)methyl)-6-(1,3-thiazol-2-ylamino)isonicotinic acid 33 mg of 2-(((1S,4S)-5-(3-chloro-2-fluorobenzoyl)-2,5-diazabicyclo[2.2.1]hept-2-yl)methyl)-6-((methoxymethyl)(1,3-thiazol-2-yl)amino)isonicotinic acid was dissolved in 0.9 ml of trifluoroacetic acid and 0.1 ml of water followed by stirring 2 hours at 75° C. The reaction mixture was concentrated in vacuo to give the title compound.

(15) Synthesis of 2-(((1S,4S)-5-(3-chloro-2-fluorobenzoyl)-2,5-diazabicyclo[2.2.1]hept-2-yl)methyl)-N,N-dimethyl-6-(1,3-thiazol-2-ylamino)isonicotinamide trifluoroacetate

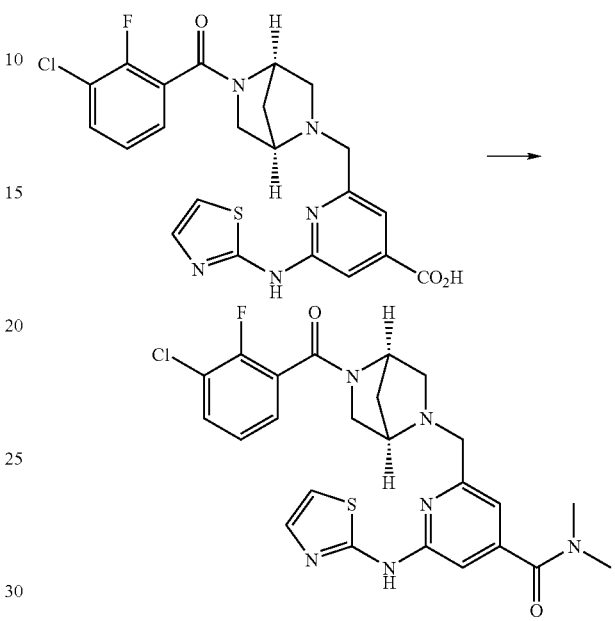

To a mixture of 62 mg of 2-(((1S,4S)-5-(3-chloro-2-fluorobenzoyl)-2,5-diazabicyclo[2.2.1]hept-2-yl)methyl)-6-(1,3-thiazol-2-ylamino)isonicotinic acid, 24 mg of dimethylamine hydrochloride, 0.096 ml of N,N-diisopropylethylamine, 0.55 ml of dimethylsulfoxide and 1.1 ml of chloroform were successively added 28 mg of 1-hydroxybenzotriazole monohydrate and 32 mg of 1-(3-dimethyl-aminopropyl)-3-ethylcarbodiimide hydrochloride, after stirring at room temperature for 24 hours, the reaction mixture was extracted with chloroform. The organic layer was washed with water and brine. The resulting mixture was dried over magnesium sulfate and filtered, the filtrate was concentrated in vacuo. The resulting residue was purified by a reversed phase preparative liquid chromatography to give the title compound as a pale yellow solid.

Spectral data of the title compound are as follows.

$^1$H-NMR (CDCl$_3$) δ: 7.51-7.43 (m, 2H), 7.37-7.30 (m, 1H), 7.21-7.15 (m, 1H), 7.03 and 7.01 (each s, total 1H), 6.90-6.82 (m, 1H), 6.80 and 6.79 (each s, total 1H), 4.93-3.19 (m, 6H), 3.16-2.60 (m, 8H), 2.07-1.95 (m, 1H), 1.83 (brd, J=9.6 Hz, 1H).

Mass: 515, 517 (M+1)$^+$.

Examples 22 to 24 were synthesized in the same manner as in Example 21 as follows.

Example 22

Synthesis of 2-(((1S,4S)-5-(2-fluoro-3-(trifluoromethyl)benzoyl)-2,5-diazabicyclo[2.2.1]hept-2-yl)methyl)-N,N-dimethyl-6-(1,3-thiazol-2-ylamino)isonicotinamide trifluoroacetate $^1$H-NMR (CDCl$_3$) δ: 7.93-7.84 (m, 1H), 7.80 (brt, J=6.8 Hi, 1H), 7.55-7.46 (m, 2H), 7:28-7.20 (m, 2H), 7.18-7.09 (m, 1H), 5.16 and 4.85 (each s, total 1H), 4.78-4.48 (m, 3H), 4.06-3.66 (m, 4H), 3.13 and 3.11 (each s, total 3H), 3.01 and 2.99 (each s, total 3H), 2.58-2.32 (m, 2H).

Mass: 549 (M+1)$^+$.

Example 23

Synthesis of 2-(((1S,4S)-5-(3-chloro-2-cyanobenzoyl)-2,5-diazabicyclo[2.2.1]hept-2-yl)methyl)-N,N-dimethyl-6-(1,3-thiazol-2-ylamino)isonicotinamide trifluoroacetate $^1$H-NMR (CDCl$_3$) δ: 7.84-7.72 (m, 2H), 7.65-7.54 (m, 1H), 7.46-7.38 (m, 1H), 7.22 (s, 1H), 7.12 (s, 1H), 7.10-7.01 (m, 1H), 5.20-4.51 (m, 4H), 4.05-3.61 (m, 4H), 3.12 and 3.11 (each s, total 3H), 3.01 and 3.00 (each s, total 3H), 2.53-2.36 (m, 2H).

Mass: 522, 524 (M+1)$^+$.

Example 24

Synthesis of 2-(((1S,4S)-5-(2-cyano-3-(trifluoromethyl)benzoyl)-2,5-diazabicyclo[2.2.1]hept-2-yl)methyl)-N,N-dimethyl-6-(1,3-thiazol-2-ylamino)isonicotinamide $^1$H-NMR (CDCl$_3$) δ: 7.89-7.76 (m, 2H), 7.71 (brt, J=7.6 Hz, 1H), 7.49-7.43 (m, 1H), 7.03 (d, J=7.6 Hz, 1H), 6.89-6.78 (m, 2H), 5.03-3.76 (m, 3H), 3.62 (dd, J=12.0, 2.0 Hz, 1H), 3.51-2.74 (m, 10H), 2.11-1.85 (m, 2H)

Mass: 556 (M+1)$^+$

Reference Examples

Reference Example 1

Synthesis of 1-tert-butyl-1H-pyrazol-3-amine

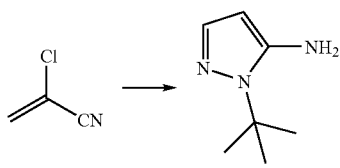

To a 600 ml of ethanol were added 59.94 g of tert-butylhydrazine hydrochloride, 79.3 g of sodium acetate and 2-chloroacrylonitrile followed by stirring at 80° C. for 12 hours. After removal of the solvent, water was added and then was neutralized with sodium hydrogen carbonate followed by extracting with ethyl acetate. The resulting organic layer was washed with saturated brine, and then dried over magnesium sulfate. The organic layer was filtered and concentrated in vacuo. The resulting residue was purified by a silica gel column chromatography (eluent: hexane/ethyl acetate=2/1 to 1/2) to give the title compound.

Reference Example 2

Synthesis of (1S,4S)-2-(2,3-dichlorobenzoyl)-2,5-diazabicyclo[2.2.1]heptane Hydrochlorate (1) Synthesis of tert-butyl (1S,4S)-5-(2,3-dichlorobenzoyl)-2,5-diazabicyclo[2.2.1]heptane-2-carboxylate

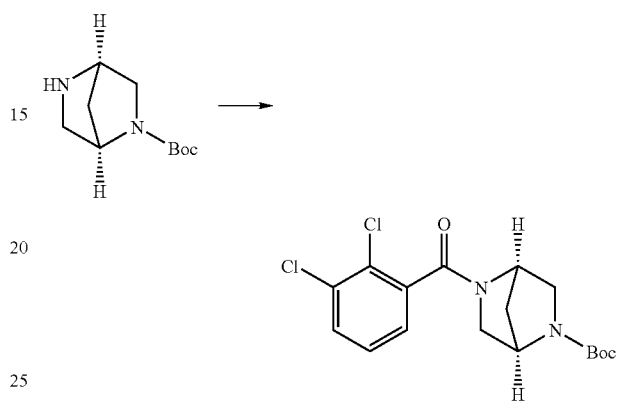

To a mixture of 3.0 g of tert-butyl (1S,4S)-2,5-diazabicyclo[2.2.1]heptane-2-carboxylate, 3.2 g of 1-(3-dimethyl-aminopropyl)-3-ethylcarbodiimide hydrochloride, 2.6 g of 1-hydroxybenzotriazole, 2.9 g of 2,3-dichlorobenzoic acid and 60 ml of chloroform was stirred at room temperature for 17 hours and then diluted with chloroform. An insoluble matter was filtered off using Celite and the resulting mixture was washed with water with saturated brine. The resulting organic layer was dried over magnesium sulfate and filtered, the filtrate was concentrated in vacuo and the resulting residue was purified by a silica gel column chromatography (eluent: hexane/ethyl acetate=9/1 to 1/1) to give the title compound.

(2) Synthesis of (1S,4S)-2-(2,3-dichlorobenzoyl)-2,5-diazabicyclo[2.2.1]heptane Hydrochlorate

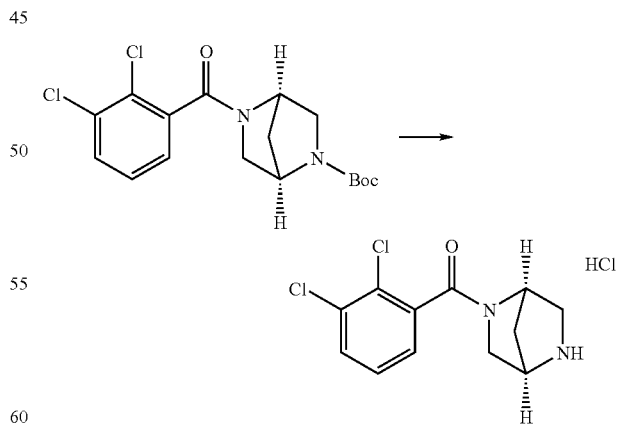

To a mixture of 5.5 g of tert-butyl (1S,4S)-5-(2,3-dichlorobenzoyl)-2,5-diazabicyclo[2.2.1]heptane-2-carboxylate and 10 ml of methanol was added hydrochloride in 1,4-dioxane solution (4 mol/l, 20 ml) followed by stirring for 1.5 hour at room temperature. The reaction mixture was concentrated in vacuo and then the resulting residue was suspended with diethylether. The precipitate was filtered and dried to give a crystal of the title compound.

Reference Example 3

Synthesis of 1-((2-(trimethylsilyl)ethoxy)methyl)-1H-pyrazol-3-amine

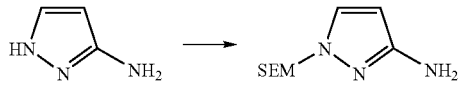

To a solution of 10 g of 1H-pyrazol-3-amine in 100 ml of N,N-dimethylformamide was added 9.6 g of sodium hydride (60%, in oil) under cooling with ice. The reaction mixture was stirred for 30 minutes, and then 21.3 ml of 2-(trimethylsilyl) ethoxymethyl chloride was added thereto. After stirring the resulting mixture at room temperature for 1 hour, aqueous ammonium chloride was added thereto, and the mixture was extracted with chloroform. The resulting organic layer was washed with water and brine, and then dried over magnesium sulfate. The organic layer was filtered and concentrated in vacuo. The resulting residue was purified by a silica gel column chromatography (eluent: hexane/ethyl acetate=4/1 to 1/2) to give the title compound.

Reference Example 4

Synthesis of 5-methyl-1-((2-(trimethylsilyl)ethoxy) methyl)-1H-pyrazol-3-amine

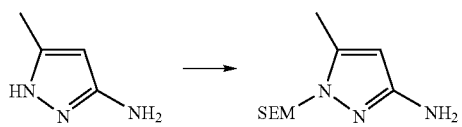

In accordance with the manner of Reference Example 3, the title compound was obtained from 5-methyl-1H-pyrazol-3-amine.

Reference Example 5

Synthesis of 3-chloro-2-cyanobenzoic Acid

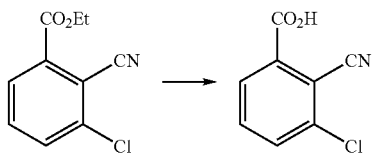

The mixture of 430 mg of methyl 3-chloro-2-cyanobenzoic acid obtained by the same manner as in U.S. Pat. No. 4,900,739, 22 ml of methanol and 2.5 ml of aqueous sodium hydroxide (1 mol/l) was stirring at room temperature for 2 hours. To the reaction mixture was added hydrochloride (5 mol/l) and was extracted with chloroform. The organic layer was washed with water and saturated brine, and then dried over magnesium sulfate. The organic layer was filtered and concentrated in vacuo to give the title compound.

Reference Example 6

Synthesis of 2-cyano-3-(trifluoromethyl)benzoic Acid

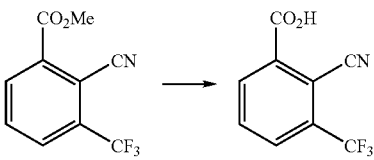

In accordance with the manner of Reference Example 5, the title compound was obtained from 248 mg of methyl 2-cyano-3-(trifluoromethyl)benzoic acid.

Industrial Applicability

The compound of the invention is characterized in that it has cell growth inhibitory action as well as synergistic action with other antitumor agents, based on excellent Aurora A selective inhibitory action, and thus it is expected as a useful antitumor agent in the field of pharmaceuticals.

The invention claimed is;
1. A compound of general formula I:

(I)

[chemical structure]

wherein:
$n_1$ is 0 or 1;
$n_2$ is 0 or 1;
R is aryl, heteroaryl, or cycloalkyl any of which may be substituted;
$R_e$ is hydrogen atom or lower alkyl which may be substituted;
with regard to $R_{a1}$, $R_{a1}'$, $R_{a2}$, $R_{a2}'$, $R_{b1}$, $R_{b1}'$, $R_{b2}$ and $R_{b2}'$, two groups selected from four groups consisting of (i) either one of $R_{a1}$ and $R_{a1}'$, (ii) either one of $R_{a2}$ and $R_{a2}'$, (iii) either one of $R_{b1}$ and $R_{b1}'$, and (iv) either one of $R_{b2}$ and $R_{b2}'$, are combined to form —$(CH_2)_n$— where n is 1, 2 or 3; and among $R_{a1}$, $R_{a1}'$, $R_{a2}$, $R_{a2}'$, $R_{b1}$, $R_{b1}'$, $R_{b2}$ and $R_{b2}'$, the groups which do not form —$(CH_2)_n$— are each independently hydrogen atom or lower alkyl which may be substituted;
$X_1$ is N;
$X_2$ is CH;
$X_3$ is CH;
$X_4$ is N;
$Y_1$, $Y_2$, and $Y_3$ are each independently CH or N; however, if $Y_1$ is CH and $R_e$ is hydrogen atom, then the two hydrogen atoms may be substituted with oxo;
W is the following residue:

[chemical structure]

wherein:
$W_1$ is CH;
$W_2$ is CH; and
$W_3$ is N;
or a pharmaceutically acceptable salt or ester thereof.

2. A compound of general formula $I_0$:

($I_0$)

[chemical structure]

wherein:
$n_1$ is 0 or 1;
$n_2$ is 0 or 1;
R is aryl, heteroaryl, or cycloalkyl any of which may be substituted;
$R_e$ is hydrogen atom or lower alkyl;
$X_1$ is N;
$X_2$ is CH;
$X_3$ is CH;
$X_4$ is N;
$Y_1$, $Y_2$, and $Y_3$ are each independently CH or N; however, if $Y_1$ is CH and $R_e$ is hydrogen atom, then the two hydrogen atoms may be substituted with oxo;
W is the following residue:

[chemical structure]

wherein:
$W_1$ is CH;
$W_2$ is CH; and
$W_3$ is N;
or a pharmaceutically acceptable salt or ester thereof.

3. The compound according to claim 2 or a pharmaceutically acceptable salt or ester thereof, wherein:
$n_1$ is 0;
$n_2$ is 0; and
R is phenyl or a 5- or 6- membered aromatic heterocyclic group which contains at least one atom selected from N, O, and S, wherein the phenyl or aromatic heterocyclic group may be substituted with one or more of the same or different substituents selected from the following:
1) lower alkyl;
2) a substituent selected from <substituent group $A_2$>; and
3) lower alkyl which is substituted with one or more of the same or different substituents selected from <substituent group $A_2$>, wherein:
<substituent group $A_2$> is halogen atom, cyano, hydroxyl, amino, lower alkyl amino, di-lower alkyl amino, lower alkanoyl, lower alkanoylamino, carbamoyl, lower alkyl carbamoyl, and lower alkyl sulfonyl.

4. The compound according to claim 3 or a pharmaceutically acceptable salt or ester thereof, wherein $Y_1$ is CH and $R_e$ is hydrogen atom.

5. The compound according to claim 4 or a pharmaceutically acceptable salt or ester thereof, wherein:
R is phenyl of which $2^{nd}$ and $3^{rd}$ positions are substituted with two substituents, which are the same or different, selected from halogen atom, methyl that may be substituted with one to three halogen atoms, and cyano.

6. A compound which is:
(a) 2-(((1S,4S)-5-(2-fluoro-3-(trifluoromethyl)benzoyl)-2,5-diazabicyclo[2.2.1]hept-2-yl)methyl)-N-1H-pyrazol-3-ylpyrimidine-4-amine;
(b) 2-(((1S,4S)-5-(3-chloro-2-fluorobenzoyl)-2,5-diazabicyclo[2.2.1]hept-2-yl)methyl)-N-(5-methyl-1H-pyrazol-3-yl)pyrimidine-4-amine; or
(c) 2-(((1S,4S)-5-(3-chloro-2-fluorobenzoyl)-2,5-diazabicyclo[2.2.1]hept-2-yl)methyl) -6-methyl-N-1H-pyrazol-3-ylpyrimidine-4-amine;
or a pharmaceutically acceptable salt or ester thereof.

7. A pharmaceutical composition comprising, together with pharmaceutically acceptable carrier or diluent, at least one compound according to claim 1 as active ingredient.

* * * * *